(12) United States Patent
Lehmuth et al.

(10) Patent No.: US 11,361,381 B1
(45) Date of Patent: Jun. 14, 2022

(54) DATA INTEGRATION AND PREDICTION FOR FRAUD, WASTE AND ABUSE

(71) Applicant: Express Scripts Strategic Development, Inc., St. Louis, MO (US)

(72) Inventors: Christopher G. Lehmuth, St. Louis, MO (US); Robert Monzyk, St. Louis, MO (US); Stanislav Samarin, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 196 days.

(21) Appl. No.: 15/999,135

(22) Filed: Aug. 17, 2018

Related U.S. Application Data

(60) Provisional application No. 62/546,783, filed on Aug. 17, 2017.

(51) Int. Cl.
*G06Q 40/08* (2012.01)
*G16H 20/10* (2018.01)
(Continued)

(52) U.S. Cl.
CPC .......... *G06Q 40/08* (2013.01); *G06F 16/212* (2019.01); *G06F 16/254* (2019.01); *G06N 5/00* (2013.01); *G16H 20/10* (2018.01)

(58) Field of Classification Search
CPC ...... G06Q 40/08; G16H 20/10; G06F 16/212; G06F 16/254; G06N 5/00
(Continued)

(56) References Cited

U.S. PATENT DOCUMENTS 6,859,780 B1 2/2005 Cunningham
7,630,908 B1 12/2009 Amrien et al.
(Continued)

FOREIGN PATENT DOCUMENTS

EP 2911079 A2 * 8/2015 ............. G16H 40/20

OTHER PUBLICATIONS

Oliva, E. M., Bowe, T., Tavakoli, S., Martins, S., Lewis, E. T., Paik, M., . . . & Medhanie, A. (Feb. 2017). Development and applications of the Veterans Health Administration's Stratification Tool for Opioid Risk Mitigation (STORM) to improve opioid safety and prevent overdose and suicide. (Year: 2017).*
(Continued)

*Primary Examiner* — Joshua B Blanchette
*Assistant Examiner* — Winston Furtado
(74) *Attorney, Agent, or Firm* — Schwegman Lundberg & Woessner

(57) ABSTRACT

Data threat evaluation systems and methods are described. A data model structure includes a data subset from the plurality of data types that predate a known threat; this third data subset includes data types from both a first data subset and a second data subset. A model schema extracts, from the data subset, data types of the first subset that predicate and indicate the threat, the model schema to produce at least an individualized data threat regression model, a script originator regression model, and a script filler data threat regression model using the extracted data types. The system may use the models back on the data set to identify potential threats. The system can operate to integrate data to predict fraud, waste or abuse.

23 Claims, 27 Drawing Sheets

(51) Int. Cl.
*G06N 5/00* (2006.01)
*G06F 16/21* (2019.01)
*G06F 16/25* (2019.01)

(58) Field of Classification Search
USPC .......................................................... 705/2
See application file for complete search history.

(56) References Cited

U.S. PATENT DOCUMENTS

| | | | |
|---|---|---|---|
| 8,099,339 | B1 | 1/2012 | Pinsonneault et al. |
| 8,738,399 | B1 | 5/2014 | Abou Nader et al. |
| 9,779,129 | B1 | 10/2017 | Lequeux |
| 2006/0053294 | A1 | 3/2006 | Akenine |
| 2007/0129969 | A1 | 6/2007 | Burdick et al. |
| 2008/0249820 | A1* | 10/2008 | Pathria .................. G06Q 10/10 705/2 |
| 2009/0076850 | A1 | 3/2009 | Hansell et al. |
| 2012/0185264 | A1 | 7/2012 | Demogenes et al. |
| 2013/0090947 | A1 | 4/2013 | Nockley |
| 2013/0238642 | A1 | 9/2013 | Clayton et al. |
| 2014/0149130 | A1* | 5/2014 | Getchius .............. G06Q 10/067 705/2 |
| 2014/0297306 | A1* | 10/2014 | Whiddon ................ G16Z 99/00 705/2 |
| 2015/0046181 | A1* | 2/2015 | Adjaoute ................ G06N 5/04 705/2 |
| 2016/0086185 | A1* | 3/2016 | Adjaoute ........... G06Q 20/4016 705/44 |

OTHER PUBLICATIONS

Oliva, E. M., Bowe, T., Tavakoli, S., Martins, S., Lewis, E. T., Paik, M., . . . & Trafton, J. A. (Feb. 2017). Development and applications of the Veterans Health Administration's Stratification Tool for Opioid Risk Mitigation (STORM) to improve opioid safety and prevent overdose and suicide. (Year: 2017).*

Rudman, W. J., Eberhardt, J. S., Pierce, W., & Hart-Hester, S. (2009). Healthcare fraud and abuse. Perspectives in Health Information Management/AHIMA, American Health Information Management Association, 6(Fall). (Year: 2009).*

Jesse C. Vivian, R. (Jun. 20, 2012). Pharmacy fraud, waste, and abuse. Retrieved Mar. 4, 2021, from https://www.uspharmacist.com/article/pharmacy-fraud-waste-and-abuse (Year: 2012).*

Kelley, R. (2009). Where can $700 billion in waste be cut annually from the US healthcare system. Ann Arbor, MI: Thomson Reuters, 24. (Year: 2009).*

Liu, J., Bier, E., Wilson, A., Guerra-Gomez, J. A., Honda, T., Sricharan, K., . . . & Davies, D. (2016). Graph analysis for detecting fraud, waste, and abuse in healthcare data. AI Magazine, 37(2), 33-46. (Year: 2016).*

* cited by examiner

2300 ↘

| BACK TO DASHBOARD | MAP | | LOG OUT | | SEARCHES | FILTERS | ANALYTICS | REPORTS | DRUG WASTE |
|---|---|---|---|---|---|---|---|---|---|

| ADD ALL | EDIT | SAVE | LOAD | NETWORK | APPLY LIST | COUNT : 0 | CLEAR |
|---|---|---|---|---|---|---|---|

CARRIER ID(s): CARRIER XYZ WITH RISK LEVEL (PERCENTILE): 90
PRESCRIBER COUNT: 7267

MINIMUM [ ] RESET FILTER
MAXIMUM [ ] APPLY FILTER

| PRESCRIBER NPI # | PRESCRIBER NAME | ADDRESS | CITY | STATE | ZIP | PHONE | RISK LEVEL FLAG | NUMBER OF CLAIMS | TOTAL BILLED ▽ | |
|---|---|---|---|---|---|---|---|---|---|---|
| 1XX1 | DOE, J. MD | ADDRESS 1 | | CA | 91780 | PHONE1 | 90 | 722 | $2,806,358 | CHART |
| 1XX2 | DOE, J2. MD | ADDRESS 2 | | CA | 90033 | PHONE2 | 90 | 663 | $1,763,266 | CHART |
| . | | | | | | | 90 | 1,220 | $1,324,779 | CHART |
| . | | | | | | | 90 | 550 | $1,267,729 | CHART |
| . | | | | | | | 90 | 118 | $922,933 | CHART |
| | | | | | | | 90 | 25 | $830,103 | CHART |
| | | | | | | | 90 | 113 | $732,428 | CHART |
| | | | | | | | 90 | 970 | $707,936 | CHART |
| | | | | | | | 90 | 9,158 | $691,284 | CHART |
| | | | | | | | 90 | 220 | $681,292 | CHART |
| | | | | | | | 90 | 570 | $668,696 | CHART |
| | | | | | | | 90 | 110 | $612,249 | CHART |
| | | | | | | | 90 | 256 | $607,139 | CHART |
| | | | | | | | 90 | 438 | $603,407 | CHART |
| | | | | | | | 90 | 1,030 | $594,322 | CHART |
| | | | | | | | 90 | 335 | $557,163 | CHART |
| 1XXN | DOE, JN. MD | ADDRESS N | | CA | 92118 | PHONEN | 90 | 134 | $554,588 | CHART |

FIG. 23

DATA INTEGRATION AND PREDICTION FOR FRAUD, WASTE AND ABUSE

CROSS REFERENCE TO RELATED APPLICATION

This application claims benefit of the U.S. Provisional Patent Application titled "PHARMACEUTICAL FRAUD, WASTE AND ABUSE INTEGRATION," Ser. No. 62/546,783, filed 17 Aug. 2018, the entire contents of the application is hereby incorporated by reference.

FIELD

The field relates to the technical fields related to integration of prediction or detection of nefarious acts related to data in a database, and more specifically, to providing a clearinghouse for the integration.

BACKGROUND

A tremendous amount of transaction and interaction data is collected by a number of different entities. Often, the data is overwhelming to intake, process, analyze. That is, the amount of data (medical or pharmacy) was too large to derive meaningful information to adequately detect fraud, waste or abuse in medical services or pharmaceutical services. Nonetheless, the data in the field of healthcare should be analyzed to check for potential fraud, waste or abuse.

BRIEF DESCRIPTION OF THE DRAWINGS

FIG. 23 is a graphical user interface for FWA risk score report, according to an example embodiment;

DETAILED DESCRIPTION

Figure 1A:
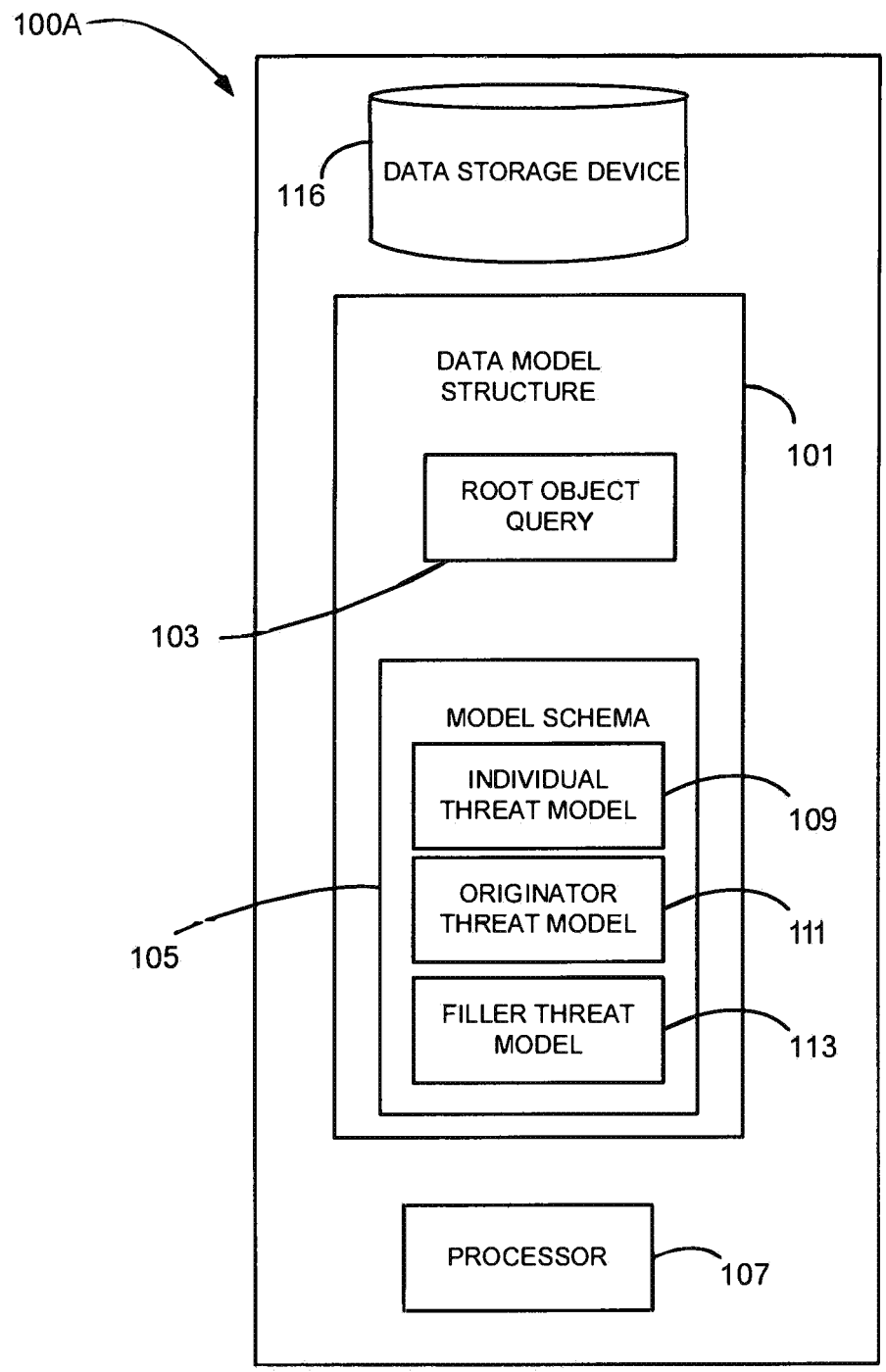
FIG. 1A is a block diagram of a data threat evaluation system, according to an example embodiment.

Example systems and methods for determining and using variable threat values, e.g., risk scores for identifying likelihood of threats based on data. The threats can include, but are not limited to fraud, waste or abuse occurring in healthcare or pharmaceutical care. The variable threat value can be determined using the data related to processing prescriptions, including adjudication or delivery of prescriptions. Processing prescriptions occurs through specialized network machines that execute dedicated instructions. Models are developed that allow the variable threat value to be computed. The threat models may be run on a data set or a subset of data that correlate to fraud, waste or abuse. The variable threat value can provide a quantified value that represents a likelihood a threat for various basis using different features selected from a same database with a global set of data types. The variable threat value can be compared to other variable threat value or threat thresholds to focus efforts in investigating potential threats, e.g., fraud, waste and abuse.

The data threat regression models use features that are identified as types of data in the database, e.g., prescription data or healthcare data that indicate or influence the likelihood of fraud, waste or abuse. The features are identified as those that are indicative of possible FWA in an example. The features can be identified from a known threat, e.g., a known incidence of FWA. Various statistical analysis can be performed to determine the data types in the database that are indicative of a potential threat. These data types can be used as features. The features are fewer than the total number of data types in the global database. That is, the system reduces the data types and only includes those that indicate a threat as features in the predictive threat model(s). The model(s) is then used to calculate a variable threat value.

When the variable threat value(s) are determined, then the variable threat value or changes in variable threat values over time may be used to trigger a flag, which may be sent to remote computer. The flag is an indicator that a potential threat, based on the underlying data is more likely than other scenarios. In an example, the present system may trigger a flag without intervention by a person. An investigation of FWA can be started when the flag is accepted.

The threat models can be provided on a graphical display, e.g., an interactive graphical user interface on a display device. The threat model and the data used by the treat model can be selected in the graphical display. The graphical display can change to output a calculated threat value as a subset of the data. The threat values can also be used to show a threat value over time to either show the basis for the flag that triggers an investigation or, in the alternative, the basis for not triggering the flag. The graphical display can include a first portion that remains the same and a second portion that changes when a type of threat or range of data to compute a threat value is selected.

Examples of the present system can also store medically sensitive health data behind a secure wall at a server, which is remote from client terminal. However, the client terminal can control operation of the server to calculate the threat value or FWA value, which is then shared with the client device. That is, the medical and prescription data is stored securely remote from the client device, which triggers the model to determine a threat value to be provided from a remote server to the client device.

In the following description, for purposes of explanation, numerous specific details are set forth in order to provide a thorough understanding of example embodiments. It will be evident, however, to one of ordinary skill in the art that embodiments of the invention may be practiced without these specific details.

The methods and systems may be used to maintain records or other data on certain persons and entities to use the data to determine potential for a threat, e.g., a fraud, waste or abuse threat. The potential can be identified as a variable threat value. In an example, the potential is a risk score. The variable threat value can be associated with a pharmacy, a patient, a prescriber (e.g., a doctor, a physician's assist, a nurse, a pharmacist and the like), or combinations thereof. In the context of healthcare, and prescription drugs more specifically, master records may be maintained on prescribers, pharmacies, and patients. The master records can be securely stored apart from a client device. These records contain certain information about these healthcare participants including name, address, phone number, and the like, and claim adjudication data associated with filling the prescription. The data can be selected and filtered to use a subset of the data that indicates possible threats, e.g., fraud, waste or abuse (FWA). The subset data is used to compute the variable threat value. The variable threat value can be used to determine if the threat has exceeded a threat threshold. In an example embodiment, a threat alert can be created and sent to client computer.

In addition to maintaining the master records, the development of the master records enable insights into what would otherwise be disparate information and thereby enable accurate viewing and other utilizations of relevant threats or risk, relevant prescription drug claims, medical claims, and the like. The master record can be used to compute variable threat values, e.g., risk scores based on an individual (e.g., a patient), a script filler (e.g., a pharmacy) or a script originator (e.g., a prescriber, doctor, nurse, pharmacist and anyone licensed to write a script).

In some embodiments, the methods and systems enable integration of provider information, prescription claims, patient information and medical claims to identify risk, develop risk scores, links and relationships between individual providers, provider organizations, health plans and accountable care organizations (ACOs), provider networks, and patients, any of which may be used to further refine a risk score or identify additional risks of fraud, waste or abuse of the prescription drug system. Risk scores can also include profiling and benchmarking of pharmacies, patients and doctors using various factors, including therapeutic class, patient demographics, brand and generic drugs, specialty drugs and compounds, and mail versus retail channel, may be performed. Utilization and cost may be identified, thereby enabling optimization of provider networks and ACOS, Medicare and Medicaid opportunities, and fraud, waste, and abuse detection. The risk scores can be determined by predictive models that use only subsets of the data types available with the data set, e.g., prescription claims data, medical services data and the like.

The present disclosure provides an improvement in data integrity and data security. When the present system and methods operate on personal data, e.g., health care data and/or prescription drug data, such data must be secured against nefarious actors who may try to access the information. The present system can secure the data in a central computer that includes various security measures. The central computer can also implement novel and unconventional rules to process the data to provide usable output that is produced by application of the rules to the sensitive data and only the calculated results are sent outside to remote electrical machine. The present system when operating on the specific rules as described herein to calculate FWA output is a unique machine that is unconventional. It is not a routine task in the pharmaceutical arts to develop models from known fraud, waste and/or abuse that then can be applied to the same or ongoing pharmacy data, medical data or other data to predict fraud, waste or abuse and provide a flag to prompt and intervention, e.g., restricting approval through a claim adjudication system or providing a graphical user interface that shows potential fraud, waste or abuse to start an intervention, e.g., pre law enforcement or trigger law enforcement. The central computer implements the rules that output FWA results with the sensitive information being hidden behind the processed results.

The present system and methods also provide for a remote device to request the results without being able to access the sensitive data. The rules being applied to the data are not accessible to certain terminals. Some select terminals may be authorized to change the rules but some terminals are not allowed to change the rules. The terminals that can change the rules can be remote from the central computer but are trusted terminals that can alter the rules in an example embodiment. An application summary of some of the overall processes can be provided at a specific terminal and only those processes can be reached directly from the menu shown on that specific terminal.

With certain terminals only having certain levels of access to the data or rules, various limited functionalities are assigned to various terminals respectively. Thus, only a specific terminal may have limited access to all of the capabilities or programs in the central computer in an example embodiment.

FIG. 1A is a schematic view of a data threat evaluation system 100A that includes a data storage device 116 in communication with a data model structure 101. The data model structure 101 can include a root object query 103 to develop a FWA model. The data storage device 116 includes circuitry to store a plurality of data types that can be broken down into subgroupings of data types, e.g., a first data subset that relate to a threat and a second data subset that do not relate to the threat. The data model structure 101 is configured to interact with the database in the data storage device 116 to develop models from the database 116, which could not be developed by people due to the complexity and quantity of data types and data. The data model structure 101 includes a root object query 103 that, when executed, returns a third data subset from the plurality of data types that predate a known threat, the third data subset including data types in both the first data subset and the second data subset. The root query may be a first query segment in data object query directed at data in the data storage device 116. The query can contain a reference to a top level or "root" data object from which the actual transformed query can be derived. The data model structure includes a model schema 105 to extract, from the third data subset identified by the root object query 103, data types of the first subset that predicate and indicate the threat. The model schema 105 produces at least an individualized data threat regression model 109, a script originator regression model 111, and a script filler data threat regression model 113 using the extracted data types. The data types selected by the model schema 105 act as features that can be used to indicate a possible threat, e.g., by computing a variable threat value. The model schema 105 may operate to identify types of data in the third data subset that indicate at least one of fraud, waste, abuse, or a combination thereof by a patient, wherein the types of data indicate at least one of fraud, waste, abuse, or a combination thereof are fewer than all types of data.

The data storage device 116 may store a plurality of data threat regression models including an individualized data threat regression model 109, a script originator regression model 111, and a script filler data threat regression model 113. These models 109, 111, 113 can be derived from statistically significant script data types working backward from known threats as indicated in the data model structure 101.

A processor 107, which includes electronic circuitry, can load one of the individualized data threat regression model 109, the script originator regression model 111, and the script filler data threat regression model 113. The models can be stored in a separate model storage, e.g., a database separate from the data storage system 116 or in the model schema 105. The processor 107 accesses the data model structure 101 to receive or to apply at least one of the individualized data threat regression model, the script originator regression model and the script filler data threat regression model to data in the data storage device to identify potential threats by calculating a variable value produced by at least one of the individualized data threat regression model, the script originator regression model and the script filler data threat regression model. The processor 107 may be configured to generate an individualized data threat variable value over a first-time segment using the individualized data threat regression model and claims data in the data storage device 116. The processor 107 may be configured to generate a script originator data threat variable value over a second-time segment using the script originator regression model and the claims data in the data storage device 116. The processor 107 may be configured to generate a script filler data threat variable value over a third-time segment using the script filler data threat regression model and the claims data in the data storage device 116. The processor 107 may be configured to determine violation of a data threat threshold by at least one of the patient data threat variable value, the prescriber data threat variable value, and the pharmacy data threat variable value. The data threat threshold can be a value relative to other values generated by a same model or a set value that when exceeded or met indicates a likelihood of a data threat, fraud waste or abuse in a prescription drug system.

The model schema 105 may operate on the first data subset to identify data types that indicate opioid threats, e.g., fraud, waste or abuse of opioids or like drugs. In an example, the model schema 105 identifies the threat regression models as opioid models for the individual, the script originator and/or the script filler. The model schema 105 may identify as features for models. Examples of features that are extracted from the database by the model schema include, in an example embodiment, at least one of a benzodiazepine consumption feature, a number of unique prescriber and pharmacy combinations per therapy feature, a morphine equivalent dose feature, an opioid claims per pharmacy feature, a refill too soon reject transactions feature, a paid claim amount feature, a sleep claims per pharmacy feature, a number of days between earliest opioid fill and most recent opioid fill feature, a distance traveled for opioids feature, a duplicate therapy claims feature, a number of unique prescribers for control substances feature, a concomitant opioid and suboxone consumption feature, a brand claims, feature a chain pharmacy usage feature, a control substances feature, an emergency room prescriber usage feature, a night claims feature, a claims where the pharmacy and doctor are not in the same state feature, a number of submitted and then reversed transactions feature, or combinations thereof. There are certain data types that are not indicative of a threat. These data types may include an age data type, a prior authorizations data type, a specialty drug claims data type, a maintenance utilization data type, a gender data type, a line of business data type, a name data type, as features. The model schema can use select ones of the data that are predictive of threats.

In an example embodiment, the processor 107 can load one of the plurality of data threat regression models and accessing a script source database to select an individualized data threat regression model 109, a script originator regression model 111 and a script filler data threat regression model 113 from the plurality of data threat regression models based on a type of data threat processing evaluation being determined. The processor 107 can reduce the statistically significant script data types stored in the script source database by including only the statistically significant data script types that indicate threats and generate variable values indicative of a threat. The processor 107 can determine an individualized data threat variable value over a first-time segment using the individualized data threat regression model 109 and claims data in the script source database, which can be part of data storage device 116. The processor 107 can generate a script originator data threat variable value over a second-time segment using the script originator regression model 111 and the claims data. The processor 107 can generate a script filler data threat variable value over a third-time segment using the script filler data threat regression model 113 and the claims data. The processor 107 can determine violation of a data threat threshold by at least one of the patient data threat variable value, the prescriber data threat variable value, and the pharmacy data threat variable value.

The data threat evaluation system 100 can further output a notifier that indicates a variable value has exceeded a threshold for any individual variable value that is calculated using, at least in part, the models. The processor 107 can send a risk flag to a client device when a risk threshold violation by at least one of the individualized data threat variable value, the script originator data threat variable value, and the script filler data threat variable value is determined. The processor 107 wirelessly transmits the risk flag to the client device. The processor 107 is to receive a reply from the client device to trigger a threat investigation. The processor 107 is to determine a violation of a data threat threshold by determining if a rate of change of a data threat variable value from at least one of the individualized data threat variable value, the script originator data threat variable value, and the script filler data threat variable value over a fourth-time period exceed a rate threshold. The processor 107 can also determine the violation of a data threat variable value from at least one of the individualized data threat variable value, the script originator data threat variable value, and the script filler data threat variable value and audit discrepancies both increase at a first rate and a second rate, respectively. The processor 107 can determine a data threat variable value from at least one of the individualized data threat variable value, the script originator data threat variable value, and the script filler data threat variable value after a pharmacy benefit manager intervention with an increasing amount of billings after a pharmacy benefit manager intervention. The processor 170 can determine a violation of a risk threshold includes an increasing threat variable value from at least one of the individualized data threat variable value, the script originator data threat variable value, and the script filler data threat variable value and an increasing number of prescription drug claims.

The data threat evaluation system 100A can trigger a viewer to load an application to a client device. The viewer application can be stored in a database, e.g., the database devices 114, 116 or the like, and sent over a communication network, e.g., network 104, to a device, e.g., devices 102, 106, 108, 110. The viewer application is configured to provide a graphical user interface to show a threat notification, e.g., a risk score flag and/or a data threat variable value from at least one of the individualized data threat variable value, the script originator data threat variable value, and the script filler data threat variable value, or combinations thereof. The viewer application is further configured to receive an input to trigger an investigation and send the trigger to a pharmacy benefits manager device. This trigger can be a signal sent from the device running the viewer application over the network back to the database device 114, 116 or another operational device.

The model schema 105 is to select data types as features for a threat model that indicate or influence a possible threat and are fewer than the total number of data types in the database being investigated for threats. In an example, embodiment, the individualized data threat regression model includes features from statistically significant script data types to calculate the variable value with a number of the features being less than one-third of types of data in the data storage device. The individualized data threat regression model includes individualized model features that are fewer than a number of data types in the data storage device. The script originator regression model includes script model features that are fewer than the number of data types in the data storage device. The script filler data threat regression model includes script filler model features that are fewer than the number of data types in the data storage device. The model schema 105 is to extract the individualized model features, the script model features, the script filler model features from a database in the data storage device. The individualized model features indicate a threat by an individual. The script model features indicate a threat by a prescriber. The script filler model features indicate a threat by a pharmacy.

Figure 1B:
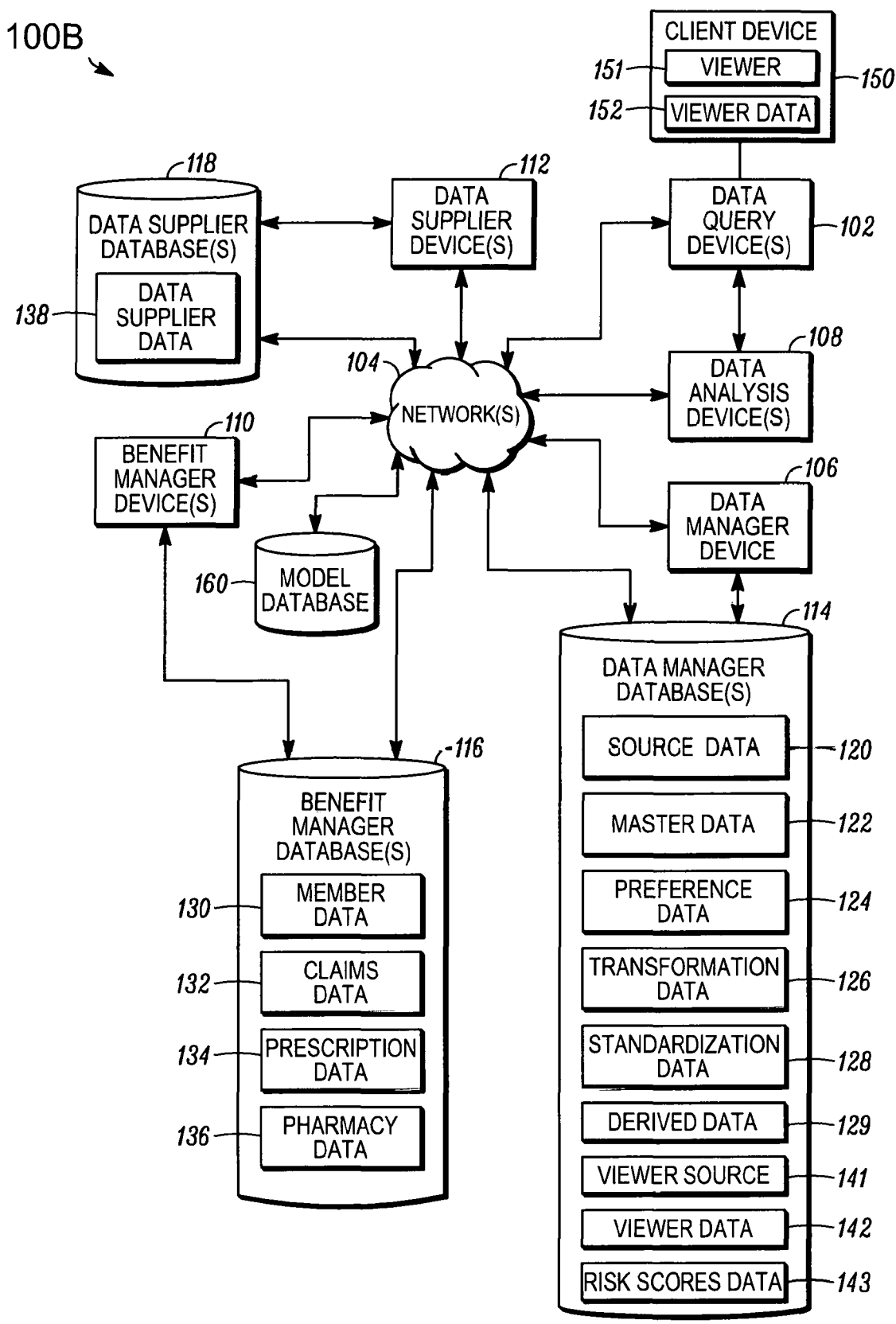
FIG. 1B is a block diagram of an example system for data thread evaluation for model determination and calculation of risk scores using the models, according to an example embodiment.

FIG. 1B is a block diagram of an example system 100B, according to an example embodiment. The system 100B is an example embodiment in which data integration may be performed and used to identify a fraud, waste and abuse variable value, which can be a risk score. The system 100B includes a data query device 102 in communication with a data manager device 106 over a network 104. The system 100B may also include a data analysis device 108, a benefit manager device 110, and a data supplier device 112. The system 100B further includes a client device 150 that can be loaded with a viewer and can have viewer data that indicates at least of one the variable value, statistical analysis of the variable values (e.g., over time, trends, thresholds, violations of thresholds, billing amounts and the like) and fraud, waste, or abuse status, which may be based on the output from any one of the devices 102, 108, or 110. The viewer on the client device 150 provides a graphical user interface that can have a first output that provides an overview of types of selections and a second output that is a result of a selection on the first output. The first output can provide an overview of the different types of threat analysis and threat models, when these are selected, then the second output is generated. The second output is specific graphic that relates to the selected analysis and threat model. The second output is different than the first output. The second output can be a change in a region of the first output. The second output can be a new graphic that replaces the first output.

The data query device 102 runs a data query, or multiple data queries, on raw data or cleaned data to obtain information of interest (e.g., to a query operator of the data query device 102), e.g., a risk score or identification of types of data that influence a risk score as possible FWA. The query operator may be a person that is performing the data query analysis utilizing the data query device 102 for himself or herself, on behalf of an organization with whom the person is employed or otherwise engaged, on behalf of an organization for whom the data query is being provided, pursuant to a device request, or otherwise. The data query device 102 can run statistical analysis of the prescription or medical data in the database to determine a threat model or a risk model, e.g., identifying features or parameters that indicate possible FWA. The features are combined using weights and impact values to compute a risk score. The data query device 102 can determine features that indicate a possible threat, e.g., FWA, from the total of the types of data in the database. The data query device 102 may start at a point in the data at which a known threat, e.g., a known FWA event, has occurred. The preceding data (i.e., a reduced data set) is analyzed to determine the features that indicate the known threat, e.g., a FWA event. The features being a further subset of the database (a reduced subset from the reduced data set that predates the known threat) will allow the ability to analyze the voluminous data that relate to prescription claims or to medical data outside of the reduced data subset. Absent using only the feature set for a specific threat calculation, the variable value representing the threat, e.g., a risk score, cannot be efficiently calculated from the data.

The data query device 102 can automatically run instructions to determine a threat variable value, e.g., a fraud, waste and abuse risk score. The data query device 102 can run a threat analysis on a rolling basis, e.g., every first-time period (two weeks or a month) on data spanning a second-time period (e.g., a year or more) using models including the features as determined herein. In some embodiments, the query operator may utilize the data query device 102 to communicate with an analysis operator (e.g., through the data analysis device 108). In some embodiments, the data query device 102 may operate automatically (e.g., pursuant to a script, pursuant to a learning algorithm, or otherwise). In an embodiment, the data query device 102 may query the data to determine a threat variable value, e.g., a FWA risk score, at set time periods, e.g., every month or every two weeks. The data query device 102 can also operate on a daily basis or upon instruction at any point in time.

Examples of the devices 102, 106, 108, 110, 112, which can be modified to be dedicated to the present system, include dedicated devices that include a processor and memory to store instructions that are loaded into the processor to form a dedicated machine for determining models for threats or using the models to calculate variable threat values. In an example, the devices are mobile. The devices 102,106,108,110, 112 may also include other computing devices, such as desktop computing devices, notebook computing devices, netbook computing devices, gaming devices, and the like, which are loaded with specific instructions to develop risk scores as described herein. Other types of dedicated electronic devices may also be used.

The network 104 by which one or more than one of the devices 102, 106, 108, 110,112 may communicate, may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may also include optical communications. Other conventional and/or later developed wired and wireless networks may also be used. In some embodiments, the network 104 may include proprietary network communication technologies such as secure socket layers (SSL) technology, technology found in a prescribing network (e.g., the electronic prescribing network operated by Surescripts of Arlington, Va.), and the like. The network 104 can be used to link multiple devices to databases and forward threat variable values, risk scores or flags of potential FWA to a remote device, e.g., a mobile device over a wireless network.

The data manager device 106 manages data that is ultimately queried by the data query device 102. As part of its operations, the data manager device 106 may clean the data that it manages (e.g., see FIG. 13 and related description below). In some embodiments, the data manager device 106 may be responsible for advance generation of information (e.g., related to threat risk) provided in response to a query. For example, certain profiles or portions of profiles of prescribers, pharmacies, and patients may be created in advance of a query, which can be part of a FWA risk score query.

The data analysis device 108 is a device that analyzes the data received by the data query device 102. For example, fraud, waste, and abuse analysis may be performed utilizing the data analysis device 108 based on the data received (e.g., from the data query device 102). In some embodiments, the fraud, waste, and abuse analysis may include determining fraudulent submission and/or of adjudication of prescription claims by a pharmacy benefit manager (PBM). The fraud, waste, and abuse may be based on improper provider behavior, member/patient behavior, pharmacy behavior, drug supplier behavior, or the like.

In an example embodiment, the data analysis device 108 may receive the results of a query conducted by the query device 102, in which the results may include cleaned data. The data analysis device 108 may analyze the query results including the cleaned data to provide a threat value, e.g., a FWA risk score and other associated data to determine potential FWA.

The benefit manager device 110 and/or the data supplier device 112 may provide data to the data manager 106 for cleaning and, when applicable, for querying, e.g., to determine the FWA threat value and other associated data to determine potential FWA.

The benefit manager device 110 is a device operated by an entity at least partially responsible for the management of a drug and/or medical benefit program. While the entity operating the benefit manager device 110 is typically a pharmacy benefits manager (PBM), other entities may operate the benefit manager device 110 either on behalf of themselves, the PBM, or another entity. In some embodiments, the benefit manager that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like.

Some of the operations of the PBM that operates the benefit manager device 110 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location. The prescription drug may otherwise be received through a different delivery channel such as a prescription drug kiosk station. All of this data may be stored and related to the patient, the prescriber and the pharmacy.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member and/or a prescription/health/medical benefit plan may directly or indirectly fund or reimburse the member or an account of the member for the co-pay. In an example, the participation in a FSA may be a factor used to calculate the risk score.

The amount of the co-pay paid by the member may vary by the benefit plan of the client with the PBM. The member's co-pay may be based on be a flat co-pay (e.g., $10), coinsurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. In an example, the amount of co-pay that a patient pays to fill a prescription may be used as a factor in calculating the threat variable value, e.g., a risk score. For example, if the patient is willing to fill a prescription at a pharmacy location that requires higher co-pay than a lesser amount at another pharmacy location, this may be a factor used in calculating the threat variable value, e.g., a risk score.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary to determine appropriate co-pay, coinsurance, and deductible for the prescription drug, and performing a drug utilization review (DUR) on the member. The PBM then provides a response to the pharmacy following performance of the aforementioned operations. As part of the adjudication, the client (or the PBM on behalf of the client) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as part of the adjudication process. The data associated with adjudication may be used to determine a threat variable value. In some cases, there may be, for example, over fifty or one hundred distinct data types that are associated with the adjudication. In some cases, there may be, for example, over three hundred data types, including derived data that can be associated with the adjudication. The results from an adjudication operation, including but not limited to any of the distinct data and the derived data, can be used in determining the FWA threat variable value, e.g., for each patient, pharmacy and prescriber. The data sets as a whole may include data that are not indicative or correlated to potential FWA. The data sets can be reduced to only the top five or top ten data types (i.e., a subset) that correlate to potential FWA.

The data supplier device 112 is device that has and/or may provide data regarding a single data category, or multiple data categories, of interest to the data manager device 106. For example, the data supplier device 112 may have data regarding prescribers, pharmaceutical manufacturers, prescription drugs, prescription drug average wholesale price (AWP), co-pays, PBM clients, and the like. In some embodiments, the data may be developed through analysis performed by the data supplier device 112 or by a person or organization that operates the data supplier device 112. In some embodiments, the data may be developed by a single organization, or multiple organizations, and provided to the data supplier device 112. The data developed or obtained by the data supplier device 112 need not be related to prescription drugs, but may be from one, or more than one, data categories of interest to the data manager device 106. In some embodiments, the data supplier operating the data supplier device 112 is a client of the PBM operating the benefit manager device 110 and/or a client of the data manager operating the data manager device 106. In some embodiments, the data supplier operating the data supplier device 112 is a governmental organization. The data supplier may also provide geographic information related to all patients, pharmacies and prescribers.

The system 100 may include a single database, or multiple databases, maintained by respective devices operated by or on behalf one or a number of different persons and/or organizations. The communication may occur directly (e.g., through local storage) and/or through the network 104 (e.g., in a cloud configuration or software-as-a-service) with a device that stores a respective database.

FIG. 1 represents an example deployment of the databases 114, 116, 118 with respective devices 106, 110, 112 respectively. However, the system 100 is not limited to this configuration. The databases 114, 116, 118 may be deployed on the data manager device 106, the data query device 102, the data analysis device 108, the benefit manager device 110, or the data supplier device 112, on more than one of the devices 102, 106, 108, 110, 112, partially on more than one of the devices 102, 106, 108, 110, 112, or may otherwise be deployed. The deployment may occur on local storage, remote storage, removable storage, and/or a different type of storage associated with the devices 102, 106, 108, 110, 112. Additionally, while a single database is depicted for each of the respective databases 114, 116, 118 is shown, multiple databases may be implemented. In the case of multiple databases, the different databases may be deployed on different systems, including the devices 102, 106, 108, 110, 112 and/or a third-party device or network.

The data manager database 114 may store source data 120, master data 122 (as part of a mater record), reference data 124, transformation data 126, standardization data 128, and/or derived data 129. Other data may also be stored within the data manager database 114. This data relates to claims data, adjudication data and other data for determining threat variable value, e.g., FWA risk score(s).

The source data 120 may generally include data to be cleaned and then used as master data 122 in performing claims data processing or FWA processing. The source data 120 may be received from the benefit manager device 110 and/or the data supplier device 112. Thus, the source data 120 may include member data 130 and/or the claims data 132 stored within the benefit manager database 116, and/or the data supplier data 138 stored within the data supplier database 118. Any of this data may be used to determine a threat variable value, e.g., FWA risk scores.

In some embodiments, in addition to including the raw unverified and/or correct data (e.g., healthcare professional information, prescription information, member information, pharmacy information, drug information, or the like), the source data 120 may also include the transformation data 126.

In some embodiments, the source data 120 includes the claims data 132. In some embodiments, the source data 120 links to the claim data 132 (e.g., by linking to the claims data 132 as stored in the database 116). This data can be used to determine threat variable values, e.g., FWA risk scores.

By way of example, the master data 122 may include data attributes for many healthcare providers (such as healthcare provider name, healthcare provider address, healthcare provider professional affiliations, healthcare provider NPI number, or the like), members (such as member name, member address, member date of birth, member healthcare plan identification number, or the like), drugs (such as drug name, drug NDC, brand name, generic name, therapy class, prescription drug average wholesale price (AWP), or the like), and pharmacies (such as pharmacy name, pharmacy address, pharmacy NPI number, or the like). The information included in the master data 122 may have been verified, or cross-checked, as being correct and accurate. For example, healthcare provider information in the master data 122 may be verified based on comparisons to information obtained from CMS NPI directories, DEA identification updates, PBM provider databases, practitioner state licenses and sanctions databases, previously submitted pharmacy claims, postal service addresses and geocodes, and the like. The information utilized to verify the master data 122 may be received from, for example, the benefit manager database 116, the data supplier database 118, and/or another source. Similarly, pharmacy information in the master data 122 may be verified based on comparisons to information obtained from CMS NPI directories, DEA identification updates, PBM pharmacy databases, practitioner state licenses and sanctions databases, previously submitted pharmacy claims, postal service addresses and geocodes, pharmacy ownership records, and the like. Drug information in the master data 122 may be verified based on comparisons to information obtained from drug product tables, DEA provided information, previously submitted pharmacy claims, and the like. As such, based on the verifications, the information included in the master data 122 may be considered correct and accurate. Accordingly, the information within the master data 122 may be considered clean. The master data 122 may further include dates that are associated with each data record. The time that data is generated or a prescription adjudicated may be used in determining threat variable values, e.g., the FWA risk score. Any of the data may be used to determine threat variable values, such as an FWA risk score.

In some embodiments, the master data 122 is in the form of master records. In general, a master record is a collection of data associated with a particular person or entity (e.g., a portion of the master data 122). A master record need not be a specific type of file format, record format, or limiting type of data structure as such, but may refer to the related data for the particular person or entity among a collection of data.

The source data 120 may include as-is data with the same data elements as the master data 122, the master data 122 itself, and all verification data including current and historical verified and edited data. Any of these data types may be used to determine threat variable values, an FWA risk score.

The reference data 124 may be data associated with master data 122 but that is deemed less significant or valuable. For example, the reference data 124 may include an address that is incorrect or no longer current, while the master data 122 includes an address that is deemed correct and current. The reference data 124 may include erroneous data, data that is out of date, data from a less reliable source relative to the master data 122, or the like.

The transformation data 126 includes data reflecting how to transform or correct the source data 120. The transformation data 126 may be general, data source specific, or otherwise. The transformational data 126 may be included within the source data 120 and/or the master data 122, separately stored in the database 114, or stored as part of a separate data collection, or otherwise. The transformation data 126 can be used to determine threat variable values, e.g., FWA risk scores.

For example, the transformation data 126 may define a transformation for correcting the differences between the received data attribute of the source data 120 and the data attribute included within the master data 122. The degree and/or nature of the defined transformation may vary depending upon preferences and/or rules. For example, the transformation may include a substitution of the last name included in the received source data 120 with the last name included in the master data 122. Alternatively, the transformation may include a substitution of the "0" in the last name included in the source data 120 with an "i" in the last name included within the master data 122.

The transformation data 126 may include information regarding various transformations that have been made to raw data included within the source data 120 as part of verifying the data and/or correcting the data so that it can be included within the master data 122. In some embodiments, the transformation data 126 may include transformations that may have been defined as generally described above. For example, the transformation data 126 may include particular transformations that were made to raw data attributes to achieved corrected data attributes that may be included within the master data 122.

The transformation data 126 may identify one, or more than one, transformations that may have been made to previously received data attributes that were different than the data attributed included within the master data 122. For example, previously received data (e.g., which may also be stored in the source data 120) may have included a misspellings of the prescribing healthcare professional's last name as "Smuth," "Snith," "Smoth," "Smurh," etc. Corresponding transformation data 126 may include transformations in which the incorrect letter is substituted with the correct letter. Other similar transformation data 126 may be included.

The standardization data 128 includes data reflecting standardized formats including a standardized spelling format, a standardized capitalization format, a wording appearance format, a numbering appearance format, and the like.

The derived data 129 is data created using the master data 122 directly or as an index (e.g., in to the claims data 132) that provides analysis of potential interest. For example, the derived data may include analytical comparative profiles calculated for various healthcare participants. The derived data 129 can be threat variable values, such as FWA risk scores, over time or other computed data that can be used to alert the system 100 to potential fraud, waste or abuse. Examples of derived data include, but are not limited to, score thresholds, number of audit discrepancies, and increase in activity of dollars billed or adjudicated, numbers of claims adjudicated, drug wholesaler data per pharmacy, and the like.

In some embodiments, the database 114 may include drug data. The drug data may include drug name (e.g., technical name and/or common name), other names by which the drug is known by, active ingredients, an image of the drug (e.g., in pill form), and the like. The drug data may include information associated with a single medication or multiple medications. In some embodiments, the drug data may be stored as a portion of the source data 120. The drug data may be used to determine threat variable values, e.g., FWA risk scores. The drug data may also include flags that indicate that a particular drug may be more prone to fraud, waste or abuse than another drug. Examples of drug classes that may be more prone to FWA include, but are not limited to narcotics, opioids and benzodiazepines.

In some embodiments, the database 114 may include provider data. The provider data may include information regarding prescribers and/or providers of healthcare services. The provider data may include, by way of example, provider name, national provider identifier (NPI) information associated with the providers, location data regarding the location of the providers, information data regarding the provider hours and/or telephone number, provider network association data defining the provider network associations of which the providers are associated, business relations with other providers, services provided by the provider (e.g., prescriptions issued by the provider, treatment services administered by the provider, testing services administered by the provider, etc.), and the like. The providers may be at a physician's office, a hospital, a testing laboratory, a pharmacy, a location associated with a PBM, or the like. In some embodiments, the provider data may be stored as a portion of the source data 120. The provider data may be used to determine threat variable values, e.g., FWA risk scores.

In some embodiments, the drug data and/or the provider data may be received from a device (e.g., the benefit manager device 110 from the benefit manager database 116). In some embodiments, the drug data and/or the provider data may be derived from the source data 120. In some embodiments, the drug data and/or provider data are a portion of the master data 122.

The benefit manager device 110 may provide certain member data 130, claims data 132, prescription data 134, and/or pharmacy data 136 from the database 116 for storage in the database 114 as part of the source data 120. The member data 130 may include information regarding members of a pharmacy benefit plan and/or patients of one, or more than one, pharmacy. The member population may be for a single pharmacy benefit plan (e.g., offered on behalf of a single company), or may be for multiple pharmacy benefit plans. In general, the member data 130 may include member name, member contact information (e.g., address, telephone number, email address, and the like), and a client identifier that identifies the client associated with the member and/or a member identifier that identifies the member to the client. The member data 130 may be used to determine threat variable values, e.g., FWA risk scores.

The claims data 132 includes information regarding pharmacy claims adjudicated by the PBM under a drug benefit program provided by the PBM for one, or more than one, clients. In general, the claims data 132 may include client data (e.g., including an identification of the client that sponsors the drug benefit program under which the claim is made, company name, company address, contact name, contact telephone number, contact email address, and the like), an identification of the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. The claims data 132 may also include claims adjudicated for healthcare related services other than prescriptions filled under a drug benefit program. Examples of other healthcare related services may include medical services (such as treatment, screening services, laboratory services, et al.), dental related services, and vision care related services. Additional information may be included in the various claims of the claims data 132. The claims data 132 may be used to determine threat variable values, e.g., FWA risk scores.

The prescription data 134 may include information regarding prescriptions that may be issued by providers on behalf of patients, who may be members of the drug benefit plan, for example to be filled by a pharmacy. Examples of the prescription data 134 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.). The prescription data 134 may be used to determine threat variable value, e.g., FWA risk scores.

The pharmacy data 136 may include information regarding pharmacies. The pharmacy data may include, by way of example, national provider identifier information associated with the pharmacies, location data regarding the location of the pharmacies, information data regarding the pharmacy hours and/or telephone number, pharmacy network association data defining the pharmacy network associations of which the pharmacies are associated, and the like. The pharmacy data 136 may be used to determine threat variable values, e.g., FWA risk scores.

The data supplier data 138 as may be stored in the database 118 may include the member data 130, the claims data 132, clinical data, provider data, drug data, the prescription data 134, and/or the pharmacy data 136. The member data 130 and the claims data 132 may be for a same member population as maintained by the benefit manager operating the benefit manager device 110, or for a different population. In some embodiments, the source data 120 is stored separately from the member data 130, claims data 132, and/or data supplier data 138. The data supplier data 130 may be used to determine threat variable values, e.g., FWA risk scores.

The clinical data may include clinical records regarding member diagnosis and/or therapy. The clinical data may be obtained from hospitals, medical insurance companies, drug trials, medical laboratories in the form of clinical records and/or the member via online questionnaires, for example. In some embodiments, the clinical data includes medical claims and/or lab data. In some embodiments, the clinical data includes medication data (e.g., for a claim made under the medical benefit instead of the prescription drug benefit). The clinical data may be used to determine threat variable values, e.g., FWA risk scores.

By way of example, a member of a healthcare benefit program, such as a drug benefit program, may request a drug prescription be filled by a pharmacy, such as a retail pharmacy or a mail order pharmacy. When the member requests that the drug prescription be filled by the pharmacy, the pharmacy may submit a drug prescription claim, to the benefit manager of the healthcare benefit program (such as the drug benefit program as operated by a PBM). The prescription drug claim may be submitted to the PBM for adjudication to determine eligibility of the member for coverage of the prescription under the drug benefit program, a required co-pay to be paid by the member, a reimbursement to the pharmacy, etc. The data associated with the prescription drug claim may be stored in one, or more than one, of the member data 130, and the claims data 132. In some embodiments, receiving the data may include accessing the member data 130 and/or the claims data 132 stored within benefit manager database 116.

By way of example, a prescription drug claim may, for example, identify the member requesting the fill of the drug prescription, the pharmacy at which the request to fill the drug was made, a drug benefit plan identifier, an identification of the drug to be filled, and an identification of the prescribing healthcare provider, such as a doctor or other prescriber. The member may be identified by one or more of a member name, member identification (e.g., an identification number use to identify the member with respect to the drug benefit program), a member address, a date of birth, as well as other information. Similarly, the pharmacy may be identified by a pharmacy name, an address, a national provider identifier (NPI) number, etc. The drug to be filled (or that has been filled) may be identified by one or more of a drug name, a brand name, a generic name, a therapy class, a national drug code, a dosage, a form of the drug, or other information. The prescribing healthcare professional may be identified by, for example, name, addresses, professional affiliation (e.g., a healthcare provider organization, such as a medical practice), an NPI number, DEA number, or other identifying information. Each piece of information (e.g., member name, member date of birth, pharmacy NPI number, pharmacy address, drug name, drug NDC, prescriber NPI number, prescriber name, etc.) may each be an attribute of the claims data 132 for a particular prescription drug claim. This claim data may be used in adjudication of the claim and in determination of threat variable values, e.g., FWA risk scores.

As generally described above, a device operator of the data query device 102 may utilize the data query device 102 to run a data query, or multiple data queries, on the cleaned master data 122 to obtain information of interest (e.g., to the device operator of the query device 102 or to another individual or device). Further, a device operator of the data analysis device 108 may perform a data analysis of the query results of the query run on the data query device 102, which includes cleaned master data 122. The query run may be determined by a risk model. The query results may include threat variable values, e.g., risk scores. The threat variable values can be, e.g., risk scores, computed variable values for individuals (e.g., patients), script originators (e.g., prescribers) and script fillers (e.g., pharmacies). The device operator of the data analysis device 108 may perform the data analysis for himself, on behalf of an organization with which the device operator is employed, or on behalf of an organization for whom the data analysis is being provided. In some embodiments, the device operator of the data query device 102 and the device operator of the data analysis device 108 may be the same person, or may be different people.

Further, in some embodiments, the device operator of the data query device 102 and the device operator of the data analysis device 108 may be employed by the same organization and/or may act on behalf of the same person or the same organization. In an example, the device 102 is at a client, e.g., a business providing a pharmacy benefit or a governmental organization, e.g., the Department of Defense. The device 102 may query the databases through an interface similar to that described in U.S. patent application Ser. No. 14/484,176, titled SYSTEMS AND METHODS FOR INTEGRATING DATA, assigned to the present assignee, which is hereby incorporated by reference for any purpose. However, if the disclosure being incorporated by reference conflicts with the present written disclosure, the present written disclosure controls interpretation.

Various different types of data analysis may be performed by the data analysis device 108 on cleaned master data 122 received by the data query device 102. For example, fraud, waste, and abuse analysis, cost verification, member verification, provider investigation, drug utilization and the like may be performed utilizing the data analysis device 108 based on the cleaned data received by the data analysis device 108.

While the systems 100A or 100B are shown to include single devices 102, 106, 108, 110, 112, multiple devices may be used. The devices 102, 106, 108, 110, 112 may be the same type of device or may be different device types. When multiple devices are present, the multiple devices may be of the same device type or may be a different device types. Functionality of some or all of the devices 102, 106, 108, 110, 112 may be combined into a lesser number of devices, or may be spread among a greater number of devices. For example, the functionality of devices 102, 106, 108, 110, 112 may be combined into a single device.

Moreover, system 100 shows a single network 104, however, multiple networks can be used. The multiple networks may communicate in series with each other to link the devices 102, 106, 108, 110, 112 or in parallel to link the devices 102, 106, 108, 110, 112.

The devices 102, 106, 108, 110, 112 may be in a client-server relationship with one another, a peer-to-peer relationship with one another, in a different type of relationship with one another, or in a combination of different types of relationships with one another.

The person(s) and/or organization(s) operating the devices 102, 106, 108, 110, 112 may be the same person or organization, or may be operated by different persons or organizations.

By way of example, a pharmacy benefit manager operating the benefit manager device 110 may operate the data manager device 106. A licensee of the benefit manager may utilize the data query device 102 to perform data queries against the master data 122 maintained in the data manager database 114 by the data manager device 106. The licensee may use the results of the query in its operation of the data analysis device 108.

The data manager database 114 may include a viewer source 141 and viewer data 142. The viewer source 141 may include an application that can be used to display viewer data 142 on a remote device (e.g., client device 150) that is in communication with the devices 102, 106, 108, 110, 112. The data manager database 114 may store the risk scores 143. The viewer data 142 may include data derived for display on a viewer. The viewer data 142 may also include permissions and the types of data that a viewer may access from the database. The data manager database 114 may store the risk scores 143. The risk scores data 143 may include three types of data related to risk scoring —risk score models, risk score features, and actual computed risk scores. The risk score models are learned models, which can include statistical analysis, machine learning, and the like, from the data in the data manager database 114 that include subsets of types of data, e.g., features, that can be used to calculate a likelihood of FWA. The computed risk scores are outputs from the risk score models using the features on the prescription or medical data to produce a FWA risk score. The FWA risk score can be one of three categories of risk scores, e.g., a patient risk score, a prescriber risk score, and/or a pharmacy risk score. The risk scores can be threat variable values as described herein.

The data query device 102 may determine a likelihood of FWA as described herein and transmit a potential FWA warning to a client device 150. The client device 150 may be at a client computing system. The FWA warning can be based on the computed risk score from the derived risk score models The client device 150 may receive an input requesting that the PBM investigate the potential FWA that was flagged and transmit the investigation command back to the PBM through the device 102 and the network 104. The client device 150 may further include a viewer 151 that can act on viewer data 152 received over the network 104 to display a flag for potential FWA and a FWA score or scores. The viewer data 152 may be reformatted data from the data manager database 114. The FWA risk scores can be threat variable values The model database 160 stores various models that are used to determine threat variable values, e.g., risk scores. The models 160 can be derived to refined based on historical data. The devices 102, 106, 108, 110, 112 can load the models and, using the models, determine threat variable values, e.g., risk scores. The threat variable values can then be stored in the risk scores data on database 114.

The model database can include models from the data in the databases 114, 116 that can produce predictive FWA risk scores. In an example embodiment, the data query device 102 can request the application of a risk score model to apply to the data in the databases 114, 116. The data analysis device 108 can apply the model in some examples. The device 108 can obtain comparison data relevant to prescription drug claims, medical claims, or both the prescription drug claims and the medical claims provided by the plurality of various data sources, as described herein. The plurality of various data sources can include at least one of a benefit manager database, a data supplier database, a data manager database, and a pharmacy database. and the plurality of various data sources deployed on respective devices, the data manager database configured for storing source data received from at least one of a plurality of various data sources, a master record, and reference data record. The reference data record includes a plurality of data attributes that are associated with the plurality of verified data attributes of the master record. The plurality of data attributes of the references data record are not deemed most significant or valuable. In response to a determination that there is a difference and that the relative level of source priority of the data source of the comparison data is equal to or greater than the data source of the current state version of the master record, storing the current state version of the master record in the reference data recorder and in response to a determination that there is a difference and that the source significance of the data source of the comparison data is less than the data source of the current state version of the priority of the data source of the comparison data is equal to or greater than the data source of the master record, storing the comparison data in the reference data record. The present risk score model can be derived from the master record. The risk score models can be applied to the master record data to compute a risk score.

The model database 160 stores various models that are used to determine risk scores. The models 160 can be derived from or refined based on historical data. The devices 102, 106, 108, 110, 112 can load the models and, using the models determine risk scores. The risk scores can then be stored in the risk scores data on database 114.

Figure 2:
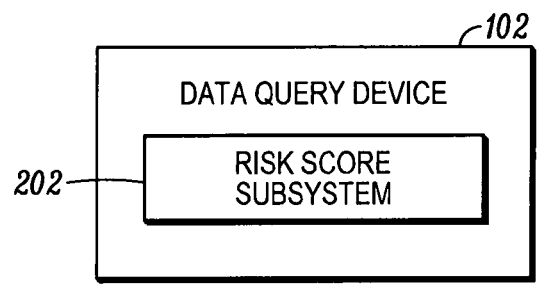
FIG. 2 is a block diagram of an example data query device that may be deployed within the system of FIG. 1, according to an example embodiment.

FIG. 2 illustrates the data query device 102, according to an example embodiment. The data query device 102 may include a risk score subsystem 202. The risk score subsystem 202 may access a particular risk score model. The risk score subsystem may use a risk score model that uses features identified as related to FWA activities in the prescription drug system or medical care system. The FWA activity can be by the patient, the prescriber, the pharmacy, or combinations thereof. The risk score subsystem 202 can be directed to one of the patient risk score, the prescriber risk score, or the pharmacy risk score. The risk score subsystem 202 may determine of FWA risk using the data stored in the databases, e.g., claim adjudication data and related data in the PBM system using the model. The data query device 102 may be deployed in the system 100, or may otherwise be used.

Figure 3:
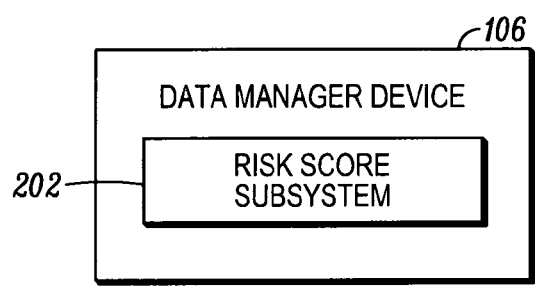
FIG. 3 is a block diagram of an example data manager device that may be deployed within the system of FIG. 1, according to an example embodiment.

FIG. 3 illustrates the data manager device 106, according to an example embodiment. The data manager device 106 may include a risk score subsystem 202. The risk score subsystem 202 may access a particular risk score model. The risk score subsystem may use a risk score model that uses features identified as related to FWA activities in the prescription drug system or medical care system. The FWA activity can be by the patient, the prescriber, the pharmacy, or combinations thereof. The risk score subsystem 202 can be directed to one of the patient risk score, the prescriber risk score, or the pharmacy risk score. The risk score subsystem 202 may determine of FWA risk using the data stored in the databases, e.g., claim adjudication data and related data in the PBM system. The data manager device 106 may be deployed in the system 100, or may otherwise be used.

By way of example, the risk score subsystem 202 may be deployed in the data query device 102, the data manager device 106, or both the data query device 102 and the data manager device 106. In some embodiments, the risk score subsystem 202 may provide server-side functionality for the data query device 102. The data query device 102 may then perform some of the functionality while other functionality is performed by the data manager device 106. The risk score subsystem 202, in an example embodiment, is a dedicated processor loaded with instructions to apply the one of the patient risk score model, the prescriber risk score model or the pharmacy risk score model that is of interest. The risk score subsystem uses the features in the model to access, weight and combine the weighted values into a score, e.g., a single numerical value of FWA risk. The numerical score may be provided as a raw number that a system uses to flag potential FWA or provided as a raw number for comparison to other FWA score results. The risk score can also be normalized, e.g., in a range, percent or the like, so that the risk score output to a viewer is easily compared to current risk score calculations, e.g., at a viewer 151.

Figure 4:
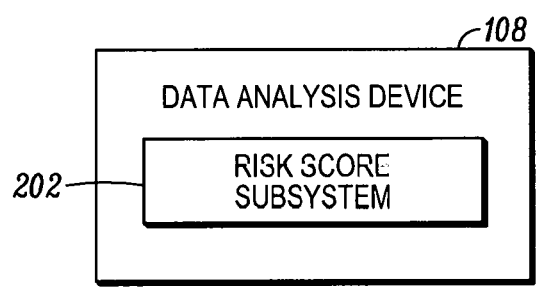
FIG. 4 is a block diagram of an example data analysis device that may be deployed within the system of FIG. 1, according to an example embodiment.

FIG. 4 illustrates the data analysis device 108, according to an example embodiment. The data analysis device 108 may be used by a device operator to enable risk score analysis. The data analysis device 108 may be deployed in the system 100, or may otherwise be used. The data analysis device 108 may include the risk score subsystem 202, which can access and apply the risk score models to data, e.g., adjudication data. The risk score subsystem 202 may include the features as described herein with relation to other figures.

Figure 5:
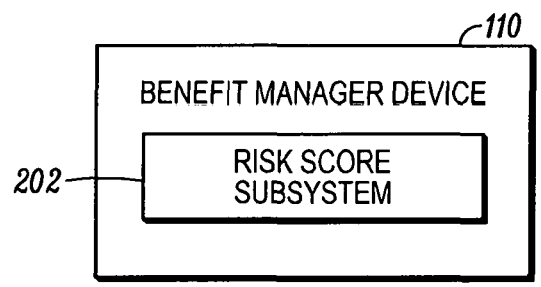
FIG. 5 is a block diagram of an example benefit manager device that may be deployed within the system of FIG. 1, according to an example embodiment.

FIG. 5 illustrates the benefit manager device 110, according to an example embodiment. The benefit manager device 110 may be used by a device operator to enable risk score analysis. The benefit manager device 110 may be deployed in the system 100, or may otherwise be used. The benefit manager device 110 may include the risk score analysis subsystem 202, which can access and apply the risk score models to data, e.g., adjudication data. The risk score subsystem 202 may include the features as described herein with relation to other figures.

Figure 6:
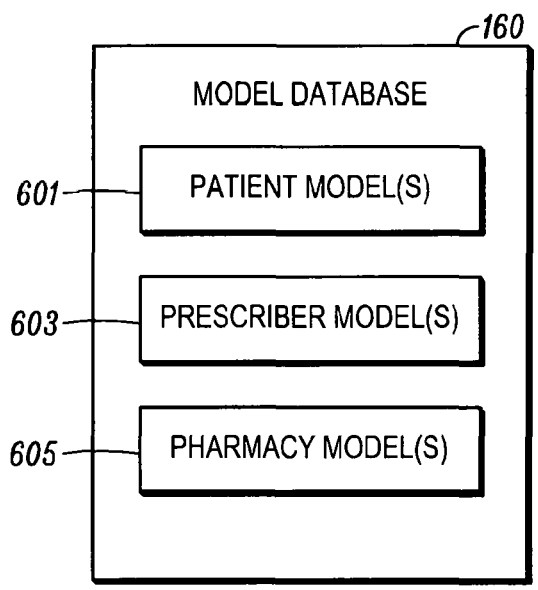
FIG. 6 is a block diagram of an example the model database that may be deployed within the system of FIGS. 1A and 1B, according to an example embodiment.

FIG. 6 illustrates the model database 160, which can include a plurality of different models that can be used to determine FWA risk scores. The model database 160 includes at least one patient model 601 that can be used to determine a patient risk score for individual patients that are part of the database, e.g., each patient that has an adjudicated claim in the database. There may be tens of millions of patient risk scores, e.g., greater than sixty million patients. The model database 160 includes at least one prescriber model 603 that can be used to determine a prescriber risk score for individual prescribers that are part of the database, e.g., each prescriber that is associated with at least one adjudicated claim in the database. There may be over one million prescriber risk scores. The model database 160 includes at least one pharmacy model 605 that can be used to determine a pharmacy risk score for an individual pharmacy that are part of the database, e.g., each pharmacy that is associated with an adjudicated claim in the database. There may be tens of thousands of pharmacy risk scores, e.g., greater than twenty thousand pharmacy risk scores. The models 601, 603, 605 include features that are indicative of and can be used to compute a likelihood of FWA. The models 601, 603, 605 can have some of the same features and may have different features. The features can be individually weighted and used as influencing the risk score to a different level. The models are also not entirely dependent on actual claims adjudicated data. The models can use derived features from the database. The models can also be use ancillary data. Ancillary data is data that is not actual claims adjudication data but is stored in the database and can be related to a likelihood of FWA. Examples of ancillary data can include the number of times that a particular pharmacy has pinged the adjudication system, the number of times that a particular pharmacy has pinged the adjudication system for a known drug that has an increased likelihood for FWA. Opioids and other narcotics can be considered as drugs that have a greater likelihood for FWA. Other ancillary data can include a patient receiving or attempting to refill prescriptions at multiple pharmacies or receiving prescriptions from multiple doctors. The models are derived from known cases of FWA and working backwards in time in the database, the features (e.g., types in the database) that indicate possible FWA are determined. These features are a reduced subset of the types of data in the database. The model database 160 stores specific predictive models that are developed from the data stored in the databases. These predictive models operate to reduce the data types, and, hence, the total data, which is reviewed to produce a risk score for possible fraud, waste or abuse. The reduction of the data types that are involved in the model makes the computing device applying the model operate more efficiently by focusing the computer on a reduced number of data types and a reduced amount of data. The predictive risk model references only those data types that a predictive of possible fraud, waste and abuse.

Figure 7:
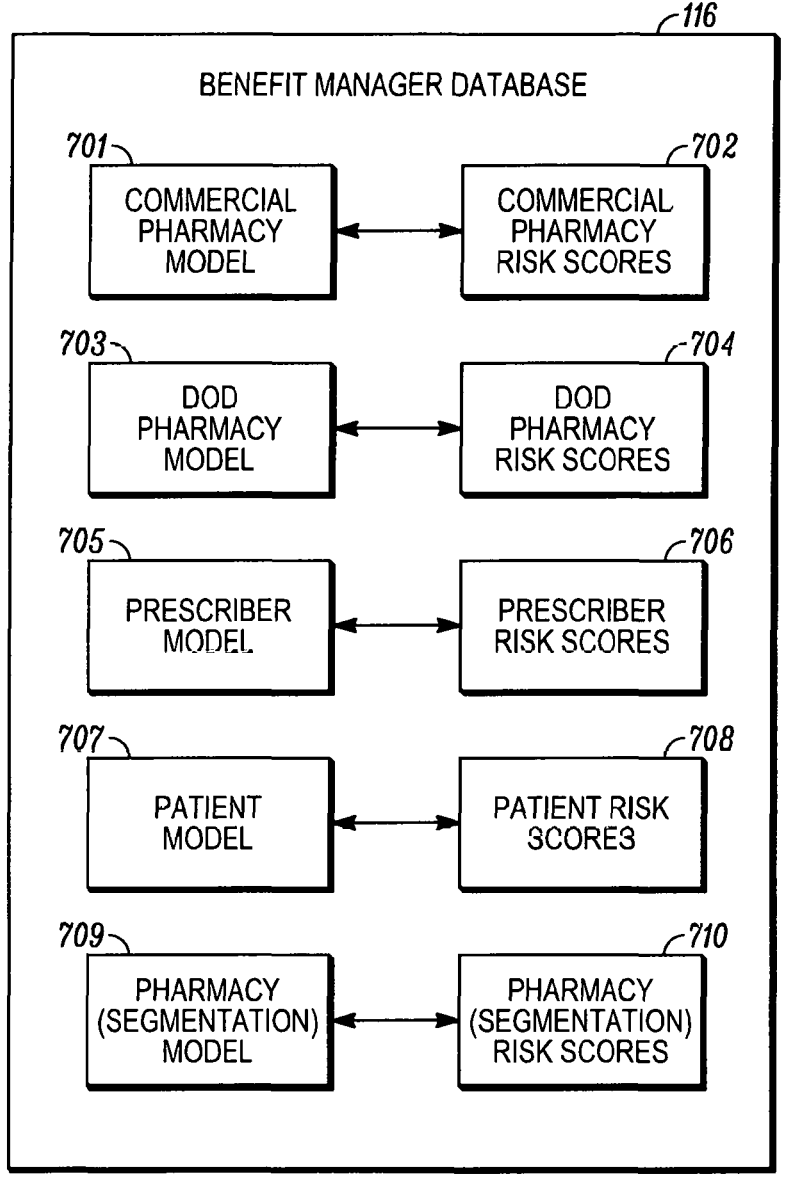
FIG. 7 is a block diagram of models and risk score types that may be deployed within a system as described herein, according to an example embodiment.
Figure 8:
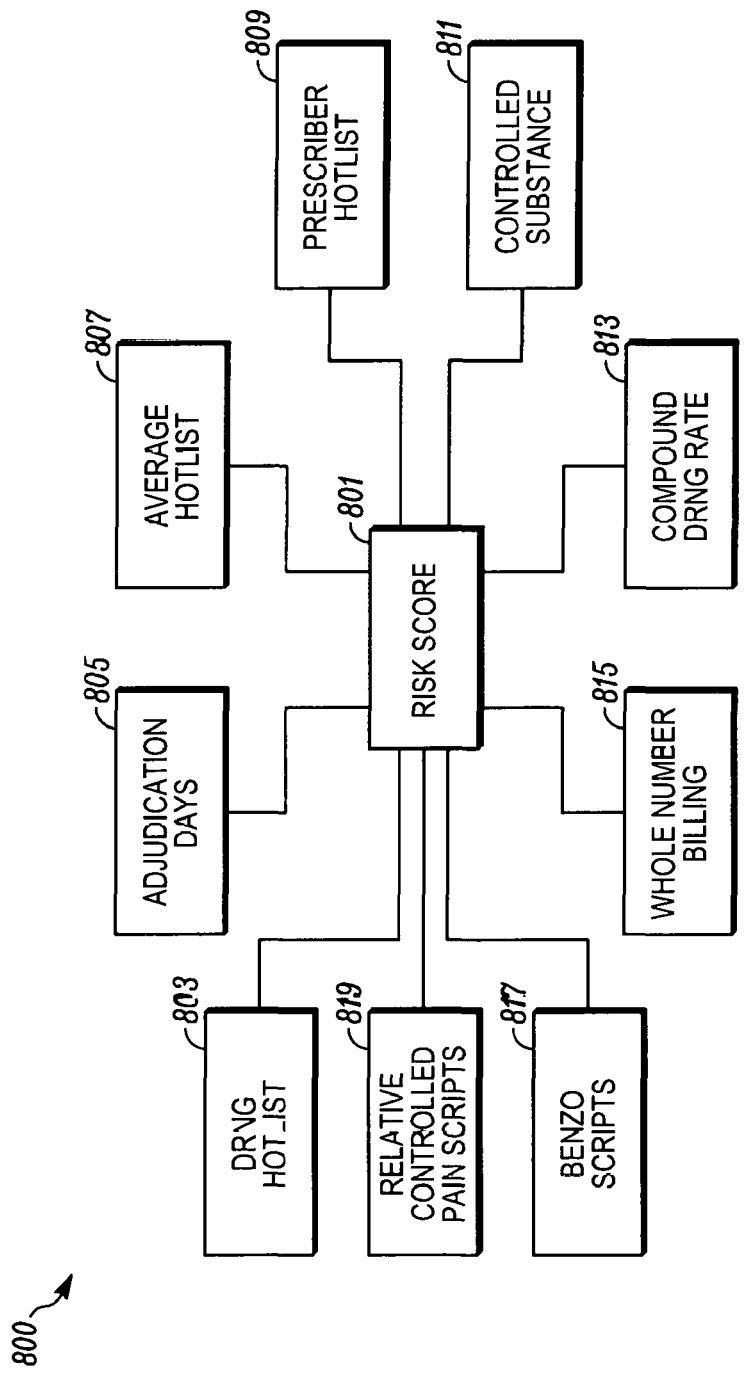
FIG. 8 is a block diagram of factors that can be input into the present systems and methods to determine a risk score, according to an example embodiment.

FIG. 7 illustrates examples of models that can be used in the devices described herein to calculate risk scores that can be used to identify various forms of fraud, waste or abuse (FWA). These models and risk scores can be stored in the benefit manager database 116. The commercial pharmacy model 701 uses the adjudication data to produce a commercial pharmacy risk score 702 for each commercial pharmacy that has an adjudication of a pharmacy claim in the database. The commercial pharmacy risk score 702 represents the likelihood that any particular pharmacy is committing FWA. The Department of Defense model 703 uses the adjudication data to produce a Department of Defense pharmacy risk score(s) 704 for each pharmacy that fills prescription in the Department of Defense health program. Other government programs may use the Department of Defense model to determine FWA risk score(s). The Department of Defense risk score 704 represents the likelihood that any particular pharmacy fulfilling prescriptions for the Department of Defense is committing FWA. The prescriber model 705 uses the adjudication data to produce a prescriber risk score 706. The prescriber risk score 706 represents the likelihood that any particular prescriber is committing FWA. The patient model 707 uses the adjudication data to produce a patient risk score 708. The patient risk score 708 represents the likelihood that any particular patient is committing FWA. The pharmacy segmentation model 709 uses the adjudication data to produce a pharmacy segmentation model risk score 710. The pharmacy segmentation risk score 710 represents the likelihood that any particular pharmacy in a pharmacy segment is committing FWA. A pharmacy segment can be based on any relatable factor that is the same in at least two pharmacies, e.g., a chain pharmacy, a compounding pharmacy, independent pharmacy, location, population size served by the pharmacy and the like. The pharmacy segmentation model 709 uses the adjudication data to produce a pharmacy segmentation score 710. The pharmacy segmentation score 710 represents the behavioral business segment into which any particular pharmacy falls. Segments were developed via unsupervised learning in the devices described herein and clustering procedures. The segments can represent how a pharmacy behaves in their prescription dispensing as opposed to how they contract with the pharmacy benefit manager. A pharmacy segment can be based on any relatable factor that is the same in at least two or more pharmacies, e.g., a chain pharmacy, a compounding pharmacy, independent pharmacy, location, population size served by the pharmacy and the like FIG. 8 illustrates a schematic view 800 of methodology to determine a risk score 801. The risk score 801 can be formed of various components, which can be stored in the databases described herein and determined using the devices described herein. The components can also be fed into a statistical analyzer (e.g., a risk model) in the devices. The statistical analyzer may include a logistic regression module to compute the risk score. The risk score can be generated from other supervised, classification model. The output of a risk score can be a one or true for the entity classifies as a fraud or a zero or false for the entity that classifies as a non-fraud. A drug hotlist component 803 is a list of drugs that are more likely to be involved in FWA. The drug hotlist component 803 could be a proprietary list of drugs that are commonly, falsely billed based on past false billings as determined by the system described herein. An example of a drug hotlist component 803 can include, but is not limited to, opioids and benzodiazepines. The drug hotlist component 803 will list drugs by their generic names and brand names and drug identification numbers.

An adjudication days component 805 can include the average number of days to adjudicate a prescription claim. This component can be the calculation of the number of days between the service date, e.g., the date the drug is sold or the date of sale and when the drug claim is processed through the billing system at the PBM correctly. The longer the adjudication day component, the more likely the pharmacy may be involved in FWA.

An average hotlist component 807 can include the number of prescriptions on the hotlist per member that are greater than a days-supplied threshold and greater than a number of claims. In an example, the days supplied threshold is twenty-five days. In an example, the number of claims is also twenty-five.

A prescriber hotlist component 809 can include a percentage of hotlists over a prescriber at a particular pharmacy. This component can indicate possible FWA when a particular prescriber prescribes a high number of hot listed drugs compared to other prescriptions that particular prescriber has at an individual pharmacy.

A controlled substance component 811 can include a rate at which a pharmacy fills certain controlled substances in its prescriptions or when a patient receives prescriptions for certain controlled substances at a pharmacy.

A compound drug rate 813 can include a percentage of dollars that come from compounded drugs relative to non-compounded drugs. The dollar amount related to compounded drugs or the number of compounded drugs, then there is a higher risk of FWA.

A whole number billing component 815 can include the number of times a particular pharmacy bills in a whole numbers, e.g., no cents, such as $9.00, $20.00 or $40.00. The higher the number of whole number billings, then there is an increased FWA risk.

A benzo script component 817 can include the number of benzodiazepines prescriptions being filled at a particular pharmacy or by a particular patient. The benzo script component 817 can be an average number of benzo scripts per member at that pharmacy. The higher the number, then it is more likely that there is FWA.

A related controlled pain prescription component 819 can include a pharmacy's number of pain control prescriptions versus other pharmacies in a similar geographic area. In an example, in a pharmacy's zip code, and the present system calculates how many controlled pain prescriptions are being filled at the pharmacy relative to other pharmacies in the area, e.g., same zip code, within a certain distance and the like. In an example, the component 819 is a percent calculated by dividing many controlled pain prescriptions are being filled at the pharmacy by the total number in the zip code. The related controlled pain prescription component 819 can be a percent of the number of controlled substances in the zip code on the pharmacy level for a particular pharmacy.

The components 803-819 represent a reduced number of data types that are being used to predict possible FWA. The components 803-819 can represent less than half, less than a third, or less than a tenth of the possible components (or data types) available in the database of prescription data or medical data. The models use these components as they have been proven to be causally linked to possible FWA. Any one of the components may not indicate FWA, but the combination of the components results in a more accurate computed risk score that is an accurate indicator of FWA.

The components 803-819 can be combined to provide the risk score 801, which may be a likelihood of FWA for a particular pharmacy. This can be computed on a rolling basis over a set period of time, e.g., one year's worth of claims data and computed on a weekly basis using a risk score model. The data used in the components 803-819 can be adjudication data stored in the databases of the PBM.

Other components may be used to determine a risk score for potential FWA. A specialty compound component may be used to determine a risk score. A mail order versus retail component may be used to determine a risk score. Therapeutic categories may be used to determine a risk score.

Not all of the components described herein are required for calculating each of the variable values that can be part of a threat risk score. These components can be used as features for calculating risk scores. Patient risk score calculation may use different components than those used to calculate a prescriber risk score. Prescriber risk score calculation may use different components than those used to calculate a pharmacy risk score. Pharmacy risk score calculation may use different components than those used to calculate a patient risk score calculation may use. However, there may be some overlap in the components between the different risk score types. In various examples, the patient risk score calculation may use different components than the components that the prescriber risk score calculation. The models on which the pharmacy risk score, the patient risk score and the prescriber risk score can be independent of one another in score calculation but can be used in combination to find situations of collusion among one or more entities from the patient, prescriber and pharmacy involved in prescriptions.

Figure 9:
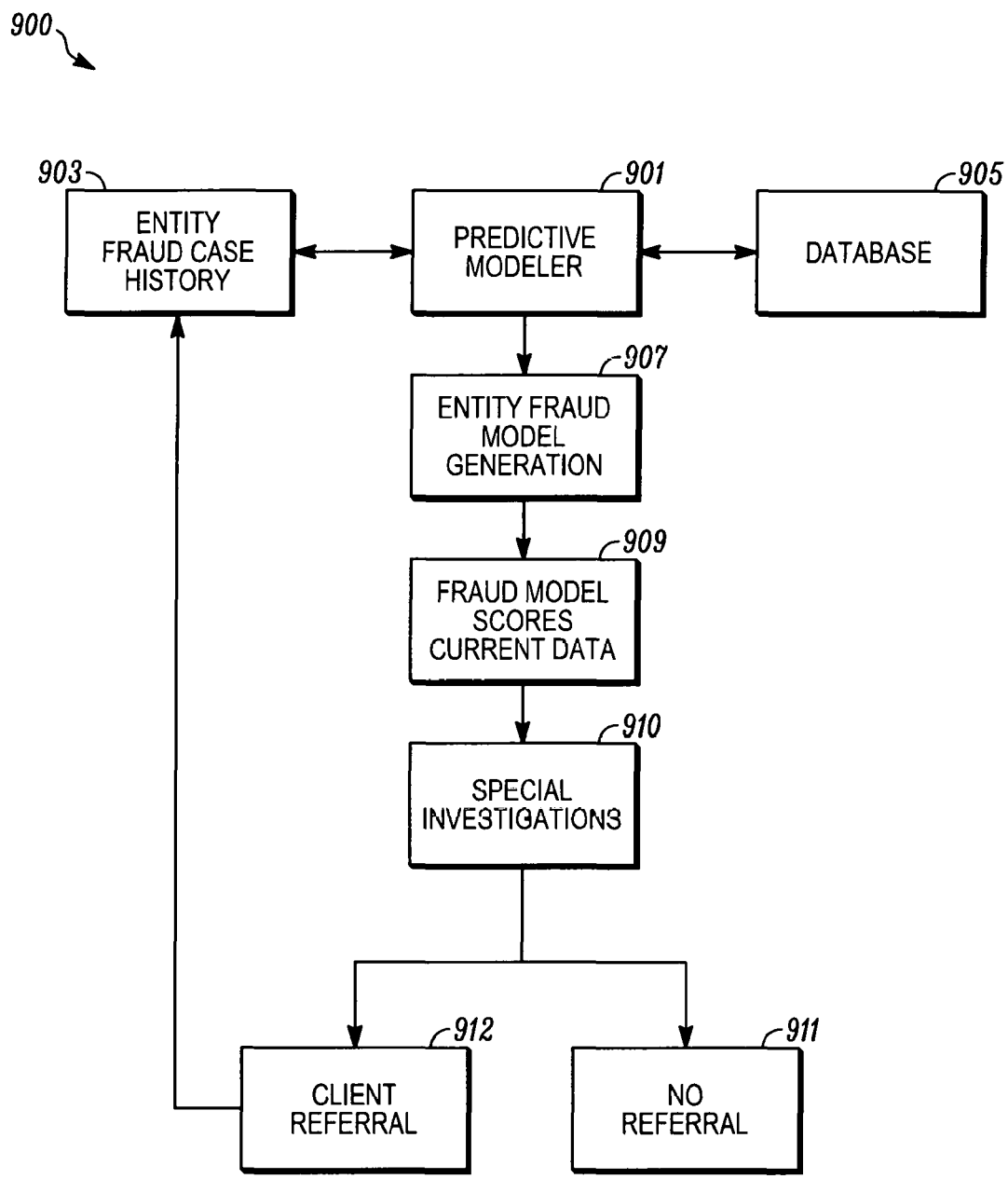
FIG. 9 is an example system for determining a fraud, waste or abuse score, according to an example embodiment.

FIG. 9 shows a schematic view of a system 900 for determining a fraud, waste or abuse risk score. As used herein, a fraud score may reflect fraud, waste or abuse related to a prescription drug, e.g., based on data related to filling or adjudicating the prescription claim. A predictive modeler 901 interacts with an entity fraud case history 903 and a claims database 905 to produce the FWA model that is generated at 907. The entity fraud model generation 907 uses component sets for each entity type, respectively. The entity types may include a pharmacy, a prescriber and a patient. The generation of the model can start a case of known FWA and work backwards in time on all of the data in the prescription or medical database to determine the types of data that indicate a likelihood of FWA. These types of data are features used in generating the model. The model is composed of features that can be weighted so that some features have a greater influence on any resulting risk score. The model also determines how the features, before or after weighting, are combined. In an example, the features are given a numerical value, then multiplied by a weighting factor, and then combined to output a risk score for the model.

At 909, the fraud model scores the current data, which can be the past year of data on a rolling basis. The risk scores are produced as provided to a special investigations unit at 910, which can be a device that filters the results to make a determination for no referral 911 or a client referral 912. The client referral 912 results from an indication that FWA is likely based on the results from the predictive model.

The predictive modeler 901 can use a logistic regression model that can be self-learning to generate an FWA model. Other statistical techniques can be used to produce the model. In an example, the predictive modeler can be a neural network. The predictive modeler 901 can use logistical regression to determine the data types to use as features in the model. The model build and verification is performed to determine what variables available in the database (e.g., data types) were actually significant in predicting FWA. The model generation can be fed known FWA entities and some non-FWA entities to train the model. FWA entities are those that are known to have committed FWA at appoint in time. The modeler looks backwards in time, e.g., a year, at all the data to determine which data types are indicative of FWA. The data can be related to the prescription that were filled by a known instance of FWA by a pharmacy, a prescriber, or a patient. The data types that are indicative of FWA are used as features in the model. In an example, the rate of FWA is generally known and data is fed to the model at a rate equal to the known rate across all of the entities. Once the model is trained and verified with the known data, the model can operate on the entire dataset of claims for the time period, e.g., a past month, past quarter, past year or multiple years. In an example, with a trained and verified model, the model can be applied to a new, current, or continuously streaming dataset of prescription claims over a given time period to predict future FWA. The model can be trained and verified with the known data that includes some FWA and some data that is not involved in FWA. The generation of a known working model is necessary to achieve reasonable results as the claims database can includes more than 70,000 pharmacies, 1.6 million prescribers, and about 65 million patients. The model FWA model scores all entities, e.g., the pharmacies, the prescribers, and the patients, to provide a baseline that allows the risk trends to be monitored.

Figure 10A:
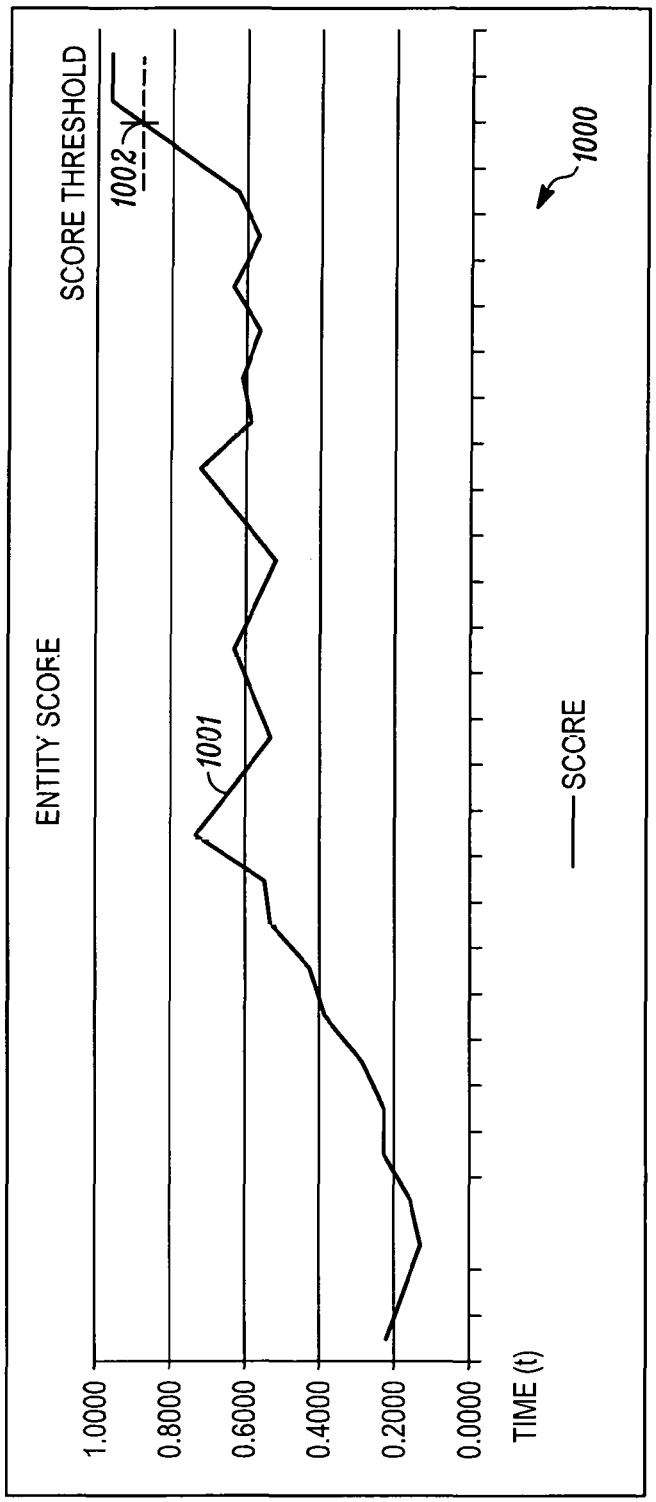
FIGS. 10A-10E show various fraud, waste or abuse risk score of a prescription drug, according to an example embodiment.

FIG. 10A illustrates schematic view of a predictive fraud model 1000 that can provide an alert within the system of potential fraud. The risk score 1001 for an entity, e.g., a pharmacy, a prescriber, or a patient, (ordinate) is tracked over a time period (abscissa). A threshold 1002 is set. When the risk score meets or exceeds the threshold, the system triggers a review by flagging this entity in the system and transmitting this information to a further device for review.

Figure 10B:
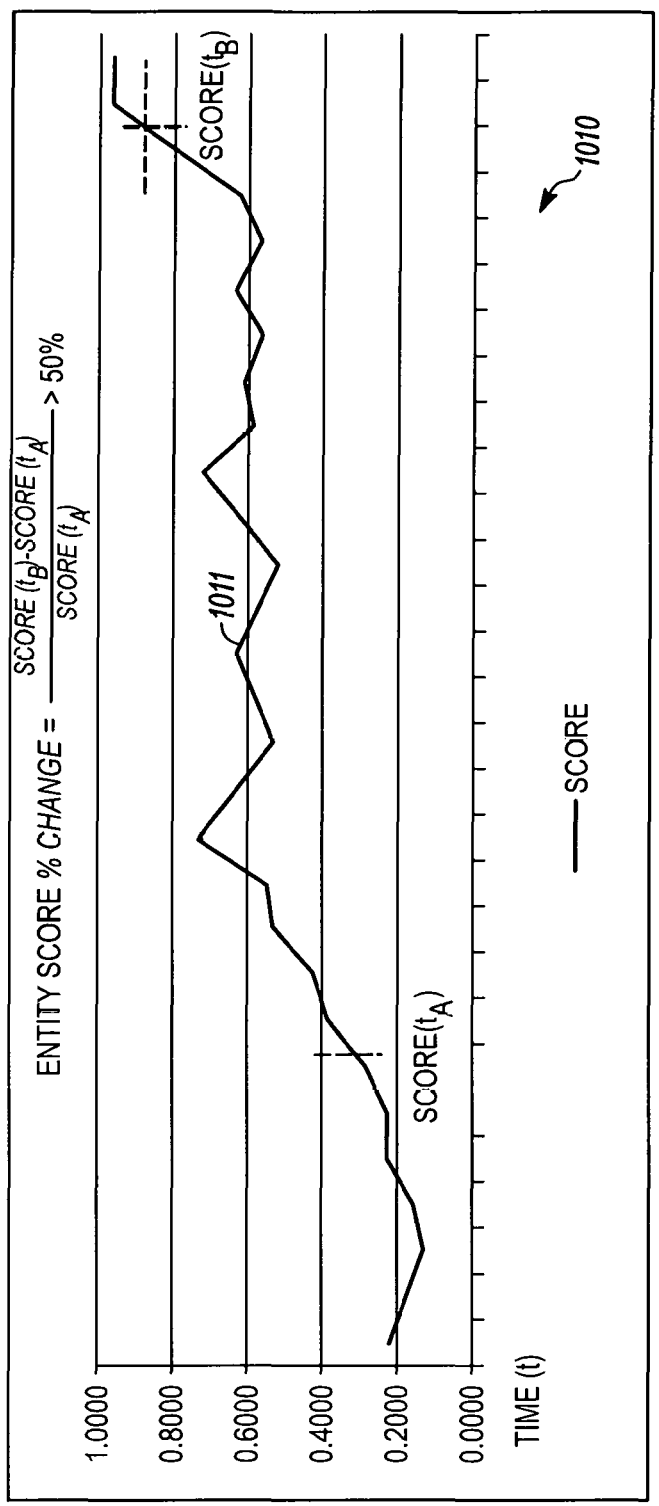

FIG. 10B illustrates schematic view of a predictive fraud model 1010, which can provide an alert within the system of potential fraud. The risk score 1011 for an entity, e.g., a pharmacy, a prescriber, or a patient, (ordinate) is tracked over a time period (abscissa). This fraud predictive model alert is triggered when any entity displays a rate of change of greater than a threshold rate over a certain time period (e.g., month to month, quarter to quarter, six months, or other time period greater than one week). The rate of change can be computed as a percentage, e.g., using (score $(t_A)$− score $(t_B)$)/score $(t_A)$, i.e., the new score minus the old score all divided by the old score. The calculated rate of change can be compared to a rate of change threshold. If the rate of change threshold is exceeded or met, then FWA may be indicated. In an example, the rate of change threshold can be set at 50%. In an example, the rate of change threshold can be set at 60%. In an example, the rate of change threshold can be set at 70%. In an example, the rate of change threshold can be set at 75% or higher in increments of 2 up to 99%. This model 1010 captures those behavior changes by the entity before the changes or rate of change reaches the threshold alert in FIG. 10A above. The model 1010 alert may indicate more of a behavior changing event in that entity. A behavioral change for a member or patient may include traumatic accident or a new illness. A behavioral change for a prescriber may include joining a new, large benefit network. A behavioral change for a pharmacy may include a nearby pharmacy closing and all Rx's and patients shift to this pharmacy. These may be legitimate changes that are reflected in the rate of change in an entity over the time period or may indicate the start of fraud, waste or abuse of the prescription system.

Figure 10C:
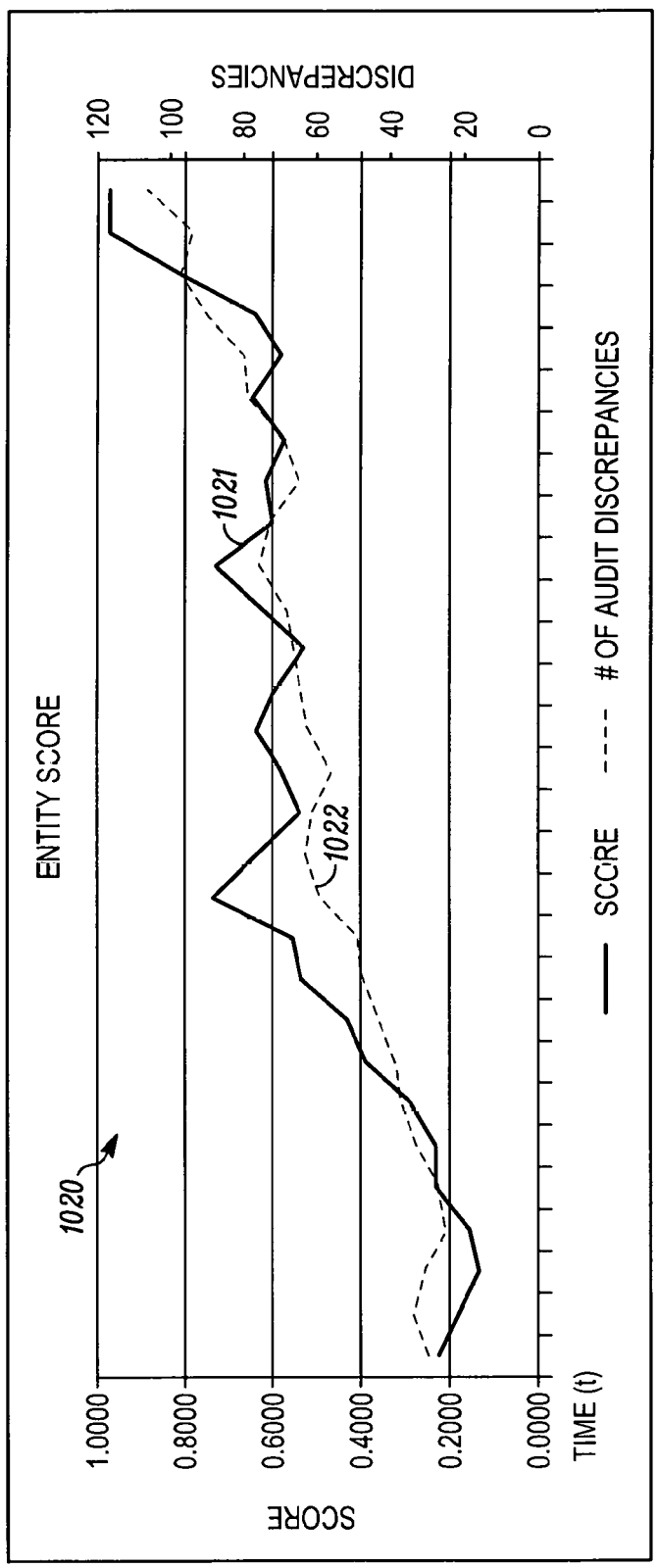

FIG. 10C illustrates schematic view of a predictive fraud model 1020. Like the above examples in FIGS. 10A and 10B, the risk score 1021 for an entity, e.g., a pharmacy, a prescriber, or a patient, (first, left ordinate) is tracked over a time period (abscissa). A number of audit discrepancies 1022 is tracked over the same time period and is graphed versus the second, right ordinate. The predictive fraud model 1020 would trigger an alert when the risk score 1021 is increasing with an increasing number of audit discrepancies 1022 for that entity over time. This data can be input from a fraud waste and abuse audit group device. Audited claims can be claims which have been billed incorrectly. Billing errors by themselves are not indicative of fraud. However, if there are enough of them, they are indicative of a disregard for appropriate billing. Overlaying audit results with an increasing fraud likelihood score provides an indication of potential fraud, waste or abuse within the PBM network.

Figure 10D:
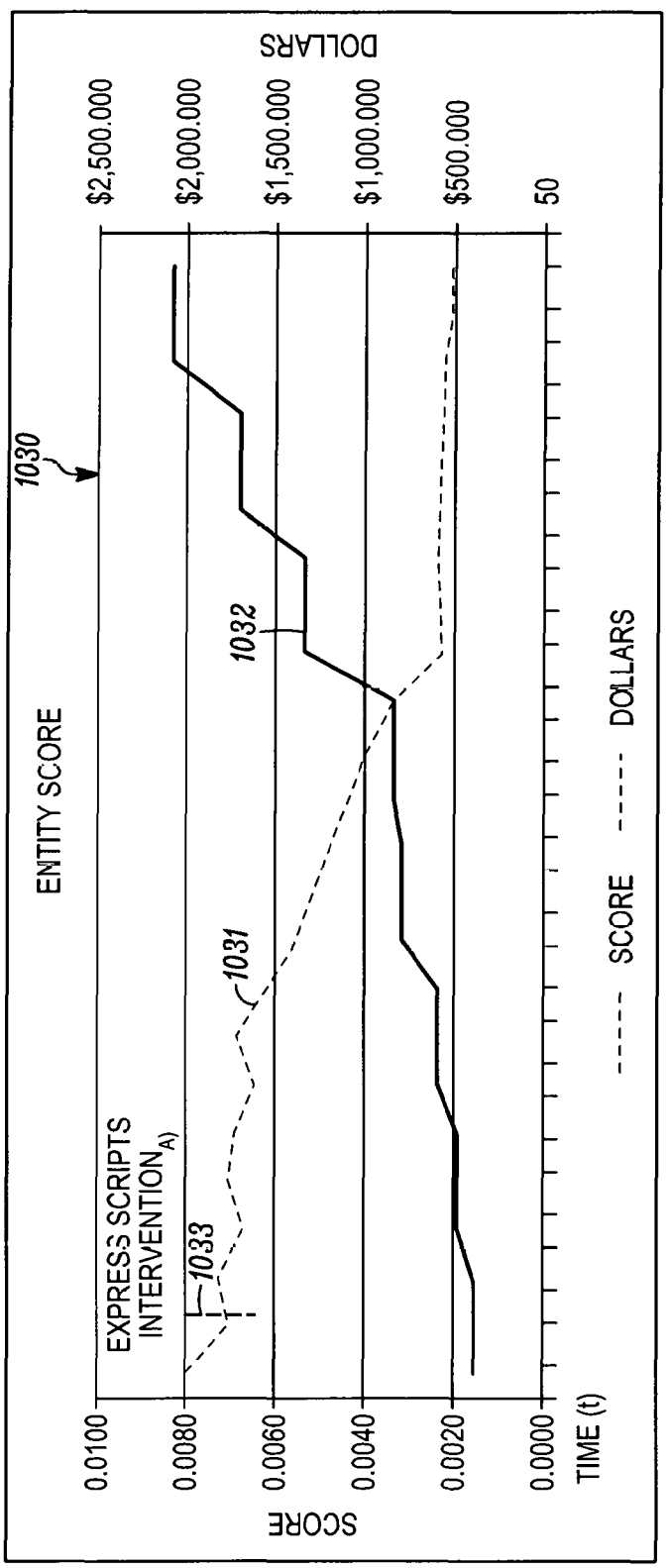

FIG. 10D illustrates schematic view of a predictive fraud model 1030. Like the above examples in FIGS. 10A-10C, the risk score 1031 for an entity, e.g., a pharmacy, a prescriber, or a patient, (ordinate) is tracked over a time period (abscissa). A prescription cost 1032 is tracked over the same time period and is graphed versus the second, right ordinate. The predictive fraud model 0.1030 would trigger an alert when the risk score trigger as a post-intervention model review, which is mainly focused on pharmacy or prescriber fraud. An investigation is started at 1033. The PBM engages the pharmacy network and the various related entities, the models allow us to measure the impacts those engagements have on the entity's behavior. Ideally, the entity would be educated as to the issue of concern and the model would show a pre/post-intervention decrease in risk score and prescription costs would decrease on that entity. However, if the engagement causes a decrease in risk score (line 1031) but an increase in prescription costs (line 1032), that would indicate that the entity has changed their behavior but has altered their behavior in a way possibly to go undetected while still increasing their billing. A trigger may be issued at any of 1033, 1034, 1035 thresholds.

Figure 10E:
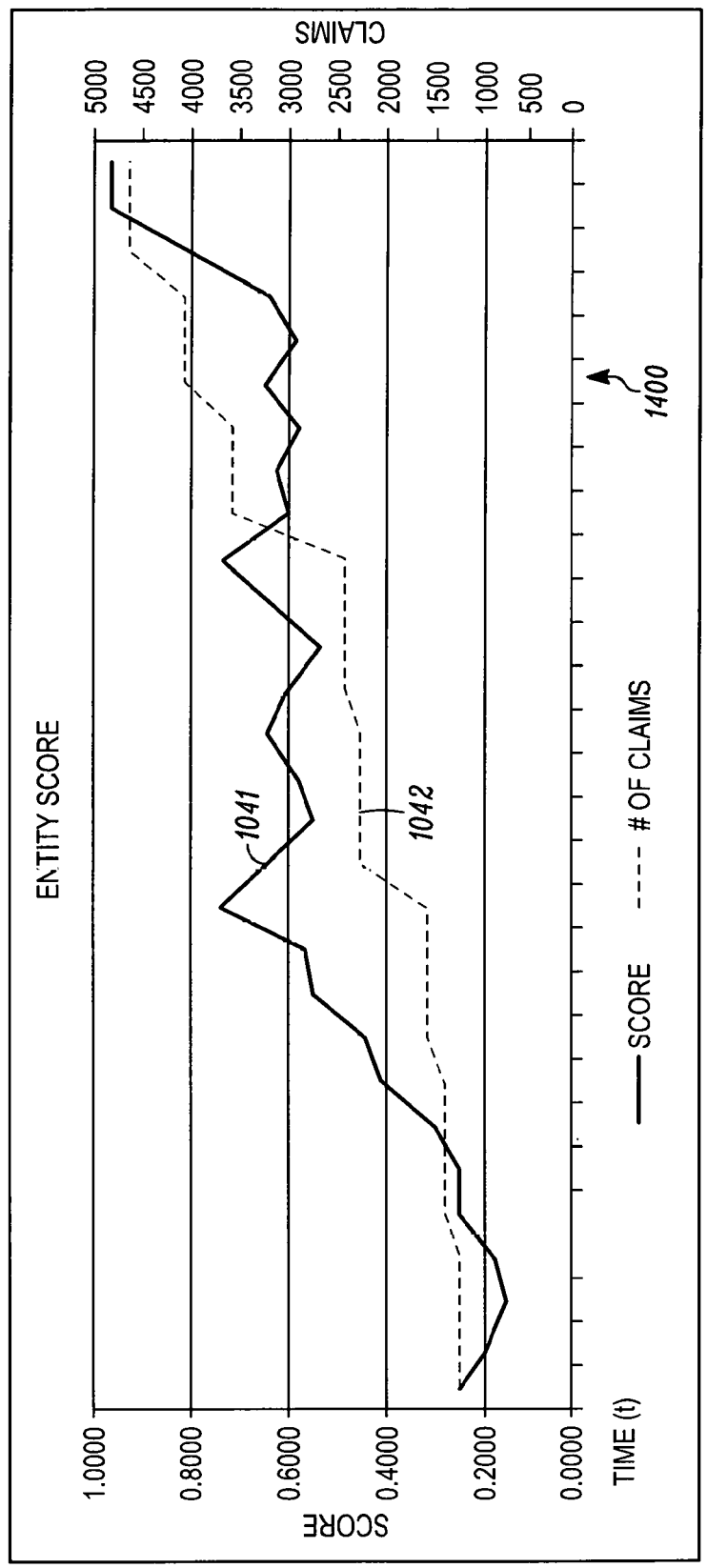

FIG. 10E illustrates schematic view of a predictive fraud model 1040. Like the above examples in FIGS. 10A-10D, the risk score 1041 for an entity, e.g., a pharmacy, a prescriber, or a patient, (ordinate) is tracked over a time period (abscissa). A number of claims 1042 is tracked over the same time period and is graphed versus the second, right ordinate. The predictive fraud model 1040 would trigger an alert based on a sharply increasing risk score and an increase in the number of adjudicated claims over time. An entity in the PBM network should behave relatively stable in a risk score over time with some fluctuations. Additionally, a new entity to the PBM network may show an increase initially but would level out and reach some sort of relative equilibrium in score. Conversely, a fraudulent entity would not level out and would increase in risk score and claims volume as a result of the diversion (member), kick-back prescription writing (prescriber), or false billing (pharmacy) increases, which are all types of fraud.

Figure 11:
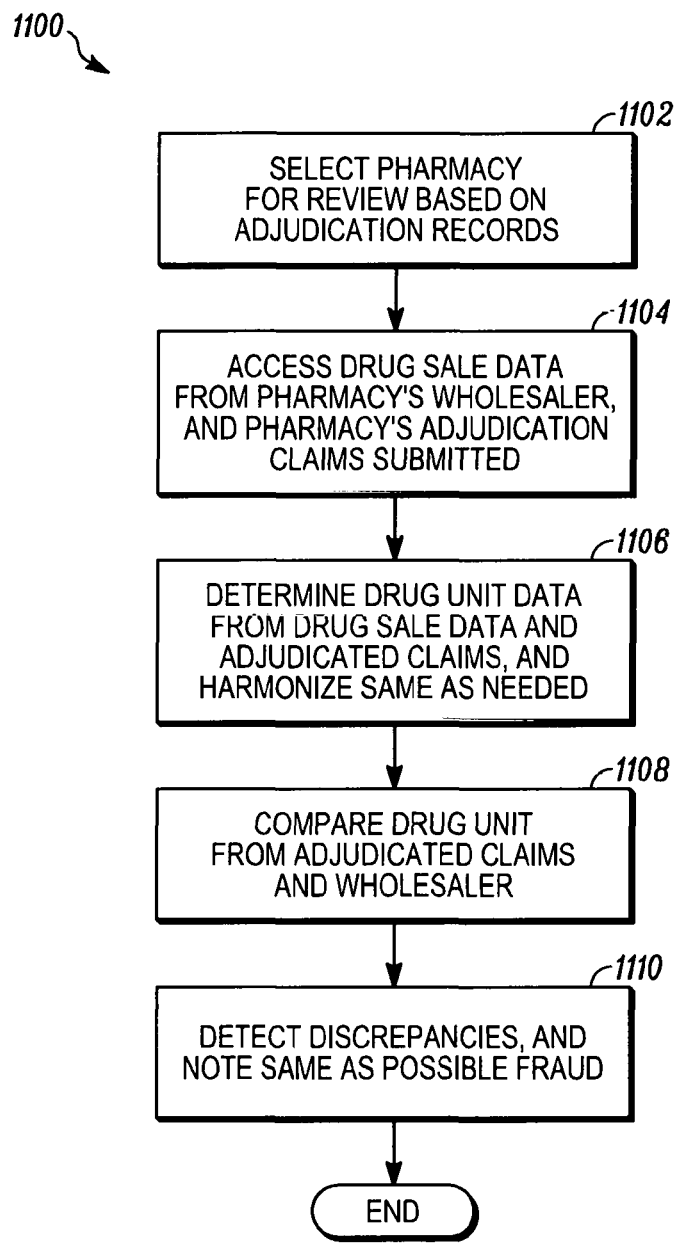
FIG. 11 is an example process flow illustrating methods for purchase evaluation, according to example embodiments.

FIG. 11 illustrates a method 1100 for purchase verification of adjudicated claims, according to an example embodiment. The method 1100 may be performed by the data query device(s) 102, partially by the benefit manager device 106 and partially by the benefit manager device 110, or may be otherwise implemented. This method inputs data into the database. The data types of this data are used to generate the risk score model(s).

At block 1102, a pharmacy is selected for review based on its adjudication data. As discussed above, a pharmacy which submits higher than expected numbers of claims involving expensive drugs, high demand drugs, low reversal rates, etc. may be selected for review.

At block 1104, the drug sale data from the pharmacy's wholesaler is accessed, along with the claims that were submitted by the pharmacy device to the PBM devices for adjudication. The data from the pharmacy's wholesaler may have been received in the form of invoices, electronically via spreadsheet, or in another form. The data regarding claims submitted by the pharmacy to the PBM for adjudication may be stored in an accessible database by the PBM. This data can be used as part of a training data set or used to calculate a pharmacy score, a prescriber score or a patient score.

At block 1106, data regarding the number of units of a prescription drug is determined based on the drug sale data and the adjudicated claims, and in some embodiments, is harmonized. The data regarding the number of units of a prescription drug may be determined based on and/or extracted from the drug sale data and adjudicated pharmacy claims data. Harmonization of the various data regarding the number of units of a prescription drug may also be performed, considering the varying reporting conventions. Such harmonization creates a direct, one-to-one, drug-for-drug, pill-for-pill, dose-for-dose comparison between drugs purchased by the pharmacy and drug claims reimbursed by the PBM. This data can be used as part of a training data set or used to calculate a pharmacy score, a prescriber score or a patient score.

At block 1108, the number of units of a prescription drug in the adjudicated claims is compared with the number of units of a prescription drug sold by the wholesaler. As the number of units of a prescription drug from the adjudicated claims represents the number, type, dose, etc. of the drugs reportedly dispensed by the pharmacy, while the number of units of a prescription drug sold by the wholesalers represents the number, type, dose, etc. of the drugs sold to the pharmacy, a comparison of such data can detect that a pharmacy submitted a claim (and received a reimbursement) for a drug which it never purchased. Thus, at block 1110, discrepancies are detected and noted as possible fraud. The discrepancy data from block 1110 can be used as an input to determining the risk score.

Figure 12:
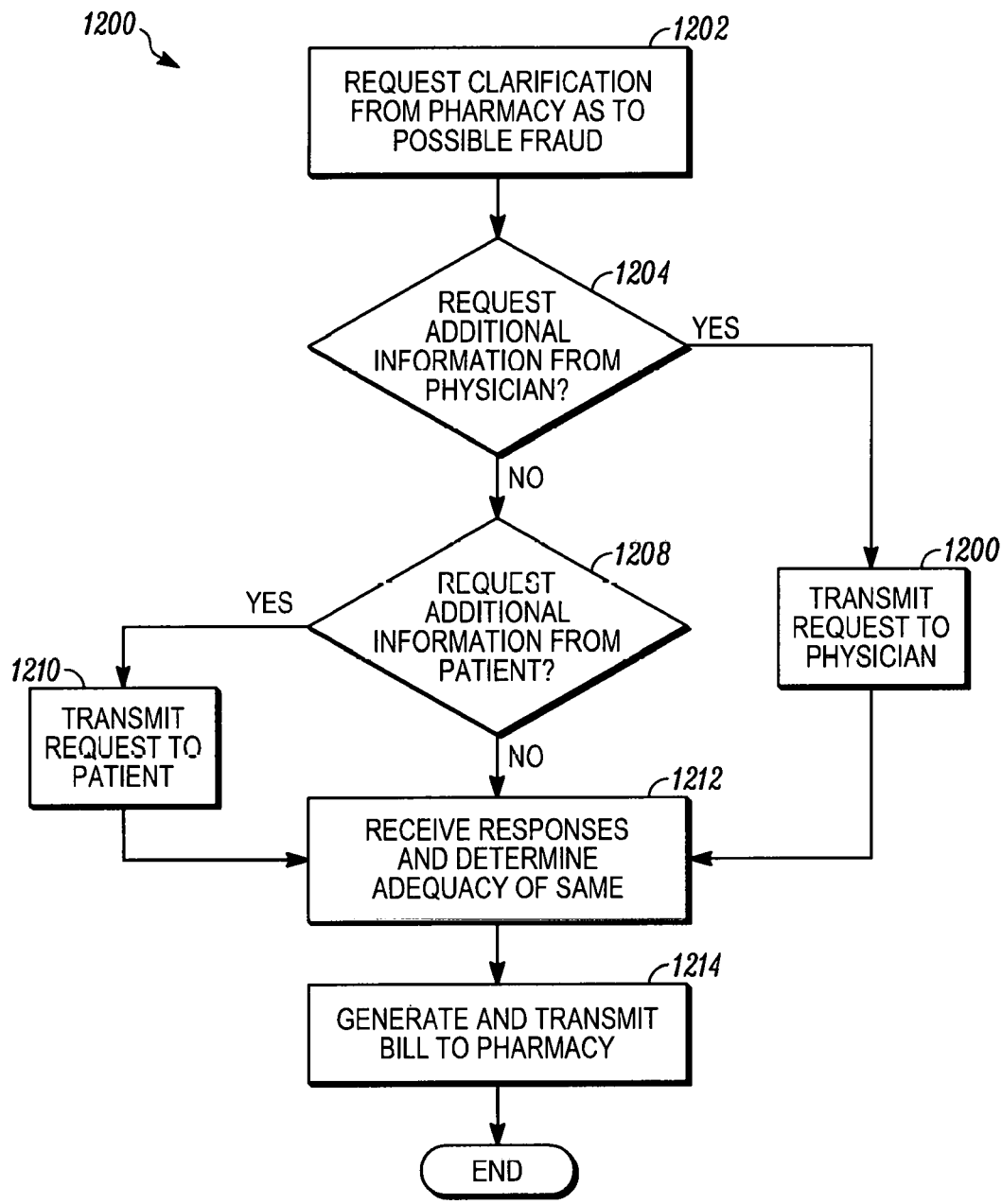
FIG. 12 is an example process flow illustrating a method for investigating fraud, waste or abuse, according to an example embodiment.

FIG. 12 illustrates a method 1200 for investigating possible fraud, according to an example embodiment. The method 1200 may be performed by the data query device(s) 102, partially by the benefit manager device 106 and partially by the benefit manager device 110, or may be otherwise implemented. The method 1200 may be triggered by a risk score that violates any of the rules or thresholds as described herein. The violation may be transmitted to a remote device at which a decision can be made to further investigate the patient, pharmacy or prescriber that is associated with the FWA violation as determined by the risk score.

At block 1202, where a possible fraud, waste or abuse has been detected, a request is transmitted to the pharmacy device for clarification as to the seemingly fraudulent activity. The pharmacy may be asked to explain the detected discrepancies, and/or provide additional data to support the claims it submitted.

At block 1204, a determination is made as to whether to transmit an additional information request to an associated physician. Such a physician may be able to confirm whether an adjudicated claim is legitimate, or was contrived by the pharmacy and/or patient. Where such a transmission is to be made, at block 1206, the request for verification is transmitted to the physician (or physician device).

Similarly, at block 1208, a determination is made as to whether to transmit an additional information request to an associated patient. Such a patient may be able to confirm whether an adjudicated claim is legitimate, or was contrived by the pharmacy and/or physician. Where such a transmission is to be made, at block 1210, the request for verification is transmitted to the patient device.

At block 1212, responses are received, and a determination is made as to whether the responses clarify the circumstances of the possible fraud as being legitimate. This step may be manual or computerized. Where a pharmacy provides additional wholesaler from which it bought drugs, any such additional drug purchases may be investigated via the purchase verification method above.

At block 1214, where a possible fraud has been detected and has not been ruled out, a bill is generated and transmitted to the pharmacy requesting repayment of costs and reimbursement amounts associated with adjudicating the fraudulent claims.

The prescription records may be derived from various data sources. The data sources may have information on these healthcare participants in different forms and different spellings. In addition, some of the data provided by the data sources may be erroneous. The methods and systems may determine from among the information received what is most valuable and likely correct and promote, or highlight, this information. The promoted information may be used for display, analysis, or the like.

Figure 13:
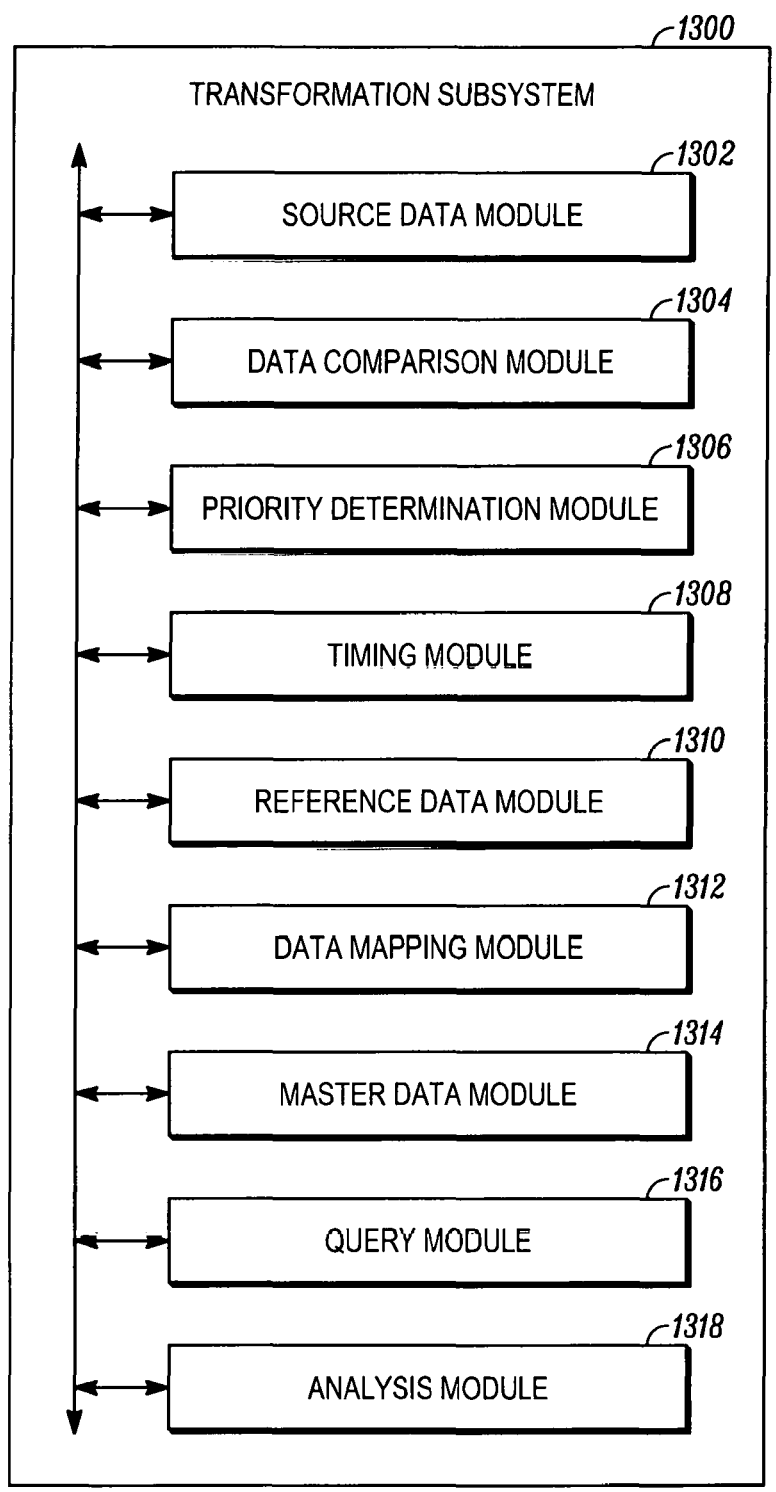
FIG. 13 is a block diagram of an example transformation subsystem that may be deployed within the query device of FIG. 2, the data manager device of FIG. 3, the data analysis device of FIG. 4, or the benefit manager device of FIG. 5, according to an example embodiment.

FIG. 13 illustrates an example transformation subsystem 1300 that may be deployed in the data query device 102, the data manager device 106, the data analysis device 108, the benefit manager device 110, the data supplier device 112, combinations thereof, or otherwise deployed in another system. One or more modules are communicatively coupled and included in the transformation subsystem 202 to enable claims data processing. The modules of the transformation subsystem 202 that may be included are a source data module 1302, a data comparison module 1304, a priority determination module 1306, a timing module 1308, a reference data module 1310, a data mapping module 1312, a master data module 1314, a query module 1316, and an analysis module 1318. Other modules may also be included.

In some embodiments, the modules of the transformation subsystem 202 may be distributed so that some of the modules are deployed in one of the devices 102, 106, 108, 110, 112 and other modules are deployed one or more of the devices 102, 106, 108, 110, 112. In one embodiment, the modules are deployed in memory and executed by a processor coupled to the memory. The functionality contained within the modules 1302-1318 may be combined into a lesser number of modules, further divided among a greater number of modules, or redistributed among existing modules. Other configurations including the functionality of the modules 1302, 1318 may be used.

The source data module 1302 stores the source data 120 received from a data source. The source data module 1302 compares the source data 120 against the master data 122. The source data 120 may be received from a single data source or multiple data sources. Examples of data sources include the benefit manager devices 110 and the data supplier devices 112. Examples of data that the source data module 1302 may store as the source data 120 include the member data 130, the claims data 132, the prescription data 134, the pharmacy data 136, and the data supplier data 138. The source data 120 may include information about a particular healthcare participant (e.g., information about a member of a prescription drug plan), or may include information about multiple healthcare participants (e.g., a prescription drug claim including information about a member of a prescription drug plan, a pharmacy that filled the prescription drug claim for the member, and a prescriber that prescribed the prescription drug of the prescription drug claim).

In some embodiments, the master data 122 used to compare against the source data 120 is in the form of master records. Examples of master records include prescriber records, pharmacy records, and patient records. In general, each master record is associated with a specific healthcare participant (e.g., a person or an entity).

In some embodiments, the source data module 1302 determines that there is no standardized format for the data source. When such a determination has been made, source data 120 that is not in such a format may be transmitted to a device (e.g., the data manager device 106) for manual processing. At manual processing, an operator may determine how to modify or otherwise handle such source data 120. In some embodiments, a device may suggest to the operator the possible changes that may be made (e.g., based on data analytics, past selections, or otherwise). Once manual processing is complete, the device transmits back to the source data module 1302 the standardized format for the data source.

Thereafter, the source data module 1302 may, based on receipt of a transmission or from previously stored information, be able to process nonmatching source data by being able to process it into a standardized format. The standardized format may include, by way of example a standardized spelling format, a standardized capitalization format, a wording appearance format, a numbering appearance format, or the like. The standardizations may be specific to a person or entity, or may be generally applicable across a number of people or entities.

In some embodiments, the source data module 1302 identifies a source data provider associated with the comparison data and determines whether a source data import from the source data provider has previously been performed. When a determination is made that the source data import has previously been performed, the source data module 1302 selects the standardized format and the standardized field splits format associated with the source data provider. In some embodiments, the source data module 1302 receives a source data transformation to correct a portion of the source data and corrects a portion of the source data with the source data transformation to create a source data portion. While the foregoing generally describes that the formatting of a data source is available based on past usage, the formatting of a data source can change such that additional standardization may be used.

In some embodiments, the source data module 1302 defines the transformation by comparing the data attributes included within the received data and the corresponding data attributes included within the master data 122, and identifying differences between the data attributes, and further identifying modifications necessary to transform the received data attribute to the data attribute included within the master data 122. Various additional and/or alternative levels of transformation granularity and/or types of transformation may be equally utilized. Further, while a transformation to a last name of a prescribing healthcare professional may be used for example, related transformations may be applied to other data attributes. Names and familial relationships may be used as components to determine FWA risk scores. Therefore, having a correct name for any entity is useful.

In some embodiments, identifying a transformation to correct the difference between the one or more than one attributes of the received data and the data attribute included in the master data 122 by the source data module 1302 may include accessing transformation data 126 that reflects multiple data transformations in the source data 120 and the master data 122. For example, the source data 120 may include a collection of data that may be unverified and/or uncorrected, including incorrect data, data with errors, etc., as well as data that may be correct. Further, the source data 120 may include various transformations (e.g., as the transformation data 126) to the unverified and/or uncorrected data that may have been made as a result of verifying or correcting the data. The source data 120 may include data received as claims data 132 (e.g., submitted pharmacy claims, or other claims submitted for coverage and/or reimbursement under a healthcare benefit program), professional licensing data received from profession or state licensing or certification agencies, national provider identifier information, DEA information, drug information received from pharmaceutical companies, financial data received from various sources, etc., as well as various additional and/or alternative information. It will be appreciated that much of the source data 120 may include at least the possibility of inaccuracies, or incorrect data. Once data within the source data 120 has been verified and/or corrected, (e.g., based on additional data sources that may provide verification and/or based on transformations to correct the data to a verified form) the data may be stored within the master data 122, which may include verified and/or corrected data and, in some embodiments, may be in the form of master records.

The system 1300 can produce the master data 122, which may include similar data as the source data 120, however the master data 122 may include data that has been verified for correctness, accuracy, and validity. The master data 122 may have been verified by comparing and/or correlating information from various sources, including the member data 130, the claims data 132, the data supplier data 138, as well as verification by internal error correction. Accordingly, the master data 122 may include cleaned member data, cleaned claims data, cleaned provider data, cleaned prescription data, cleaned pharmacy data, or the like, in that the data may be cleaned to remove errors or inaccuracies.

The data can be processed using systems and methods described in U.S. patent application Ser. No. 14/484,176, titled SYSTEMS AND METHODS FOR INTEGRATING DATA, and assigned to the present assignee, which is hereby incorporated by reference for any purpose.

Figure 14:
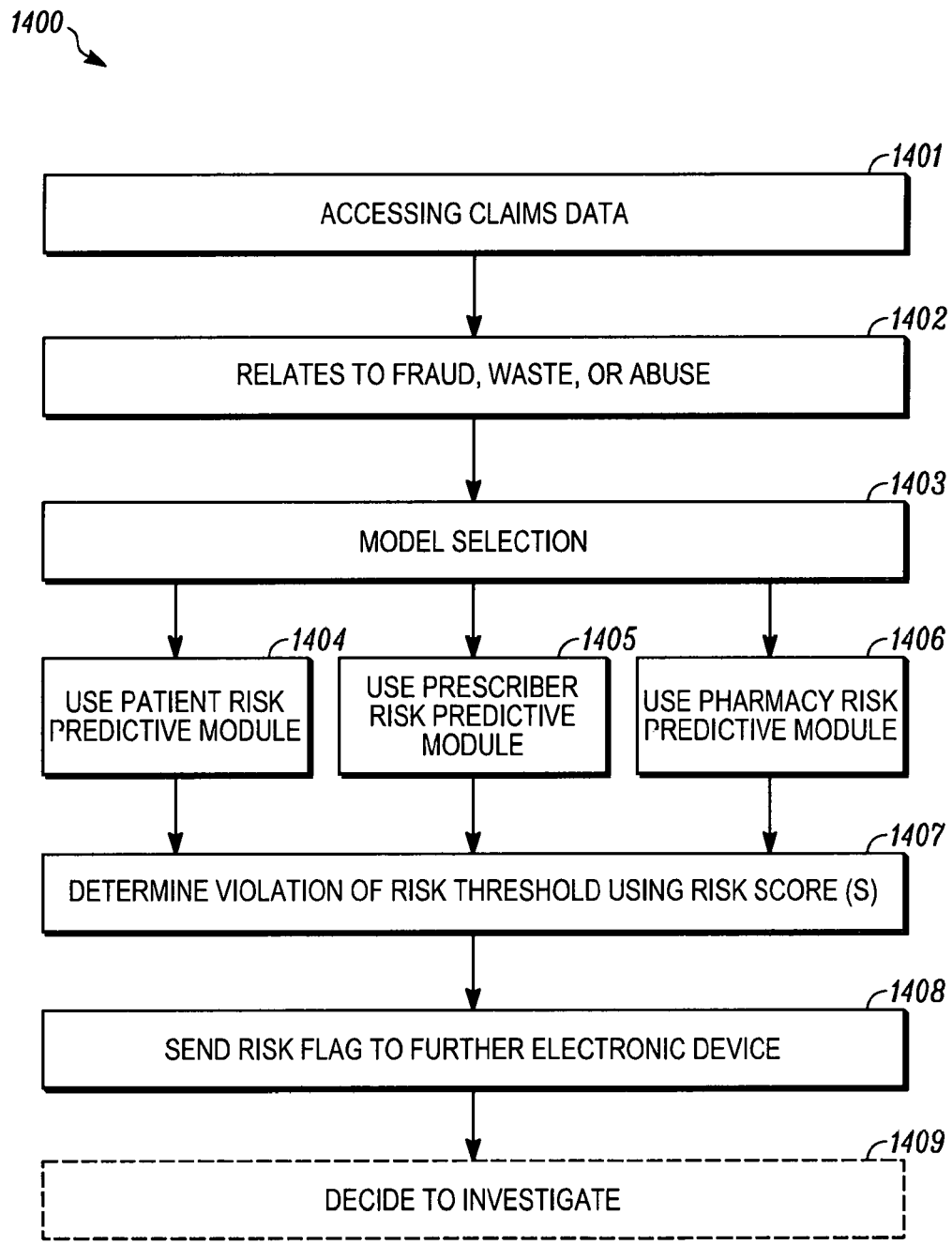
FIG. 14 is an example process flow illustrating a method for investigating fraud, waste or abuse for opioid abuse, according to an example embodiment.

FIG. 14 illustrates a method 1400 for assessing fraud, waste or abuse potential using risk scores.

At 1401, claims data associated with a patient, a prescriber, or a pharmacy is accessed. The data can be stored at any of the databases (e.g., machine accessible storage) or in a memory in any of the devices described herein. A processor, which is executing explicit instructions, may access certain claims data, used to determine a risk score, and not other data, which is not used to determine a risk score.

At 1402, a device, e.g., a processor, determines if the claims data can be used to determine whether the claims data relates to a fraud, waste or abuse determination.

At 1403, a patient risk predictive model, prescriber risk predictive model or a pharmacy risk predictive model from among a plurality of available predictive models is selected based on a type of risk score to be determined.

At 1404, the patient risk predictive model is used on the claims data to calculate, e.g., on the device or the processor, a patient risk score over a first time period.

At 1405, the prescriber predictive model is used on the claims data to calculate, e.g., on the device or the processor, a prescriber risk score over a second time period.

At 1406, the pharmacy predictive model is used on the claims data to calculate, e.g., on the device or on the processor, a pharmacy risk score over a third time period.

At 1407, at least one of the patient risk score, the prescriber risk score, the pharmacy risk score, or a combination thereof is selected to determine violation of a risk threshold. When a risk threshold is violated, e.g., exceeded, then that risk score is flagged in the system.

At 1408, the risk flag is transmitted to a client device when a risk threshold violation by the risk score is determined.

Figure 15:
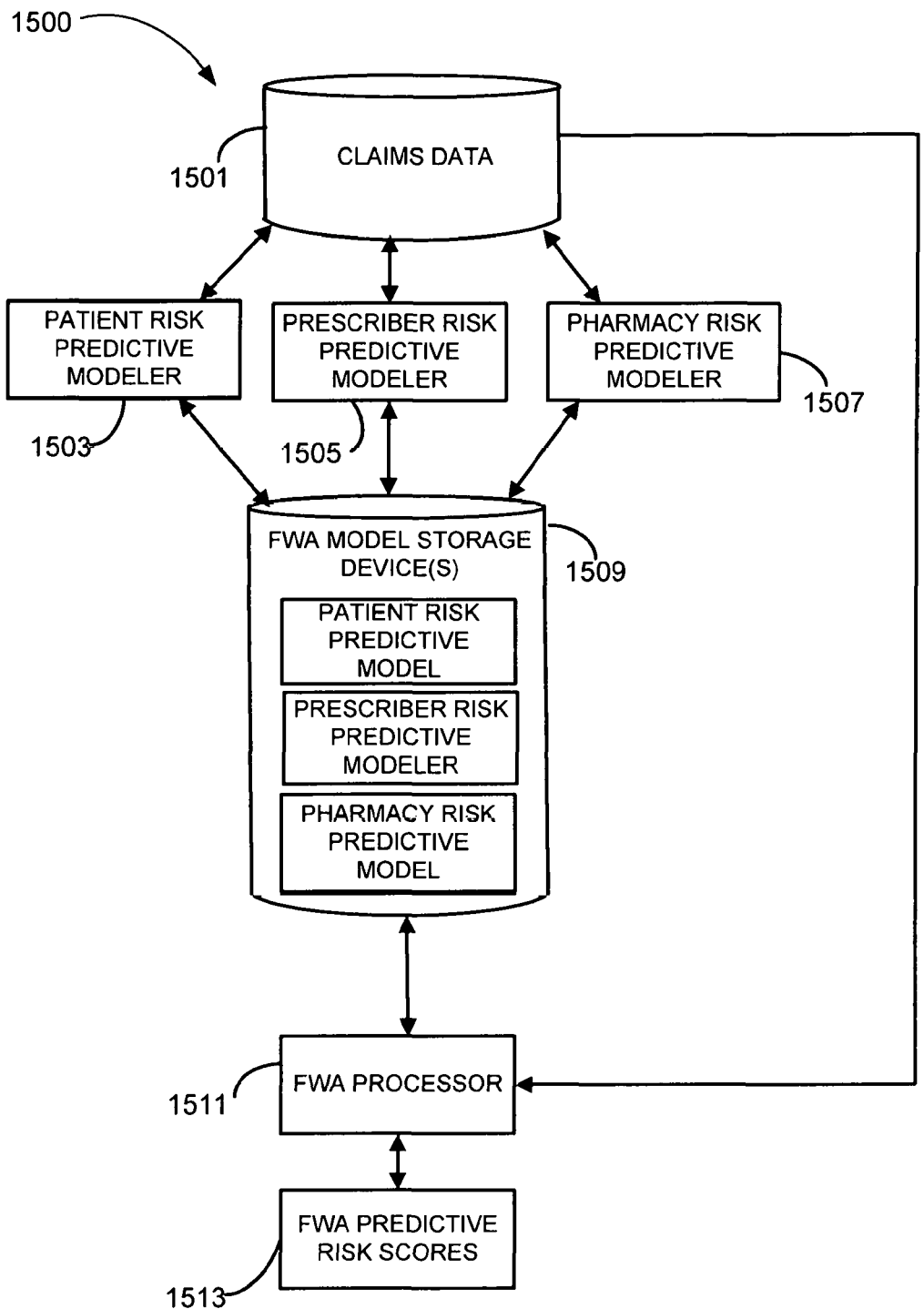
FIG. 15 is a system for determining FWA risk models, according to an example embodiments.

At 1409, an optional step may be performed. The optional step may be making decision is made whether to further investigate the flagged risk score and the associated patient, prescriber or pharmacy. FIG. 15 is a schematic view of a risk score modeling system 1500. A claims database 1501 stores data relating to medical data, e.g., prescription drug data or medical services data. This data can be voluminous, e.g., billions of claims each having tens or hundreds of data types for each claim. The data relating to both valid medical data and fraudulent data medical data are stored in the database. The database for prescription data includes patient data, prescriber data, and pharmacy data. The prescription data can be the raw data relating to a prescription claim submitted for adjudication. The prescription data can include approved prescription data that has an approved status output from the PBM to the pharmacy, rejected prescription claims, and reversed prescription claims. The prescription data can also use other data that is stored by the PBM system that is not used to directly adjudicate the prescription claim. An example of this data includes the number of times a specific pharmacy has accessed the PBM system, the number of times a specific patient has tried to fill a type of a prescription (e.g., an opioid, a narcotic, or other frequently abused drug), and other systemic data types that relate to a particular prescription but not used for adjudicating the submitted particular prescription claim.

The claims database 1501 can include a prescription drug adjudication database that includes additional data besides adjudication results.

The patient risk predictive modeler 1503 accesses the prescription drug adjudication database and discerns a patient risk predictive model using prescription drug data in the database over a first-time period that includes at least one known incident of patient FWA. The first-time period can be months or a year preceding the FWA incident. The selected FWA incident can be a patient FWA incident. The patient risk predictive modeler 1503 identifies the data types in the claims database 1501 that are predictive of FWA. These data types are used as features in the patient FWA predictive mode to be stored in the FWA model storage 1509.

The prescriber risk predictive modeler 1505 accesses the prescription drug adjudication database 1501 and discerns a prescriber risk predictive model using prescription drug data in the database over a second-time period that includes at least one known incident of prescriber FWA. The second-time period can be months or a year preceding the FWA incident. The selected FWA incident can be a prescriber FWA incident. The prescriber risk predictive modeler 1505 identifies the data types in the claims database 1501 that are predictive of FWA by a prescriber. These data types are used as features in the prescriber FWA predictive mode to be stored in the FWA model storage 1509.

The pharmacy risk predictive modeler 1507 accesses the prescription drug adjudication database 1501 and discerns a pharmacy risk predictive model using prescription drug data in the database over a third-time period that includes at least one known incident of pharmacy FWA. The selected FWA incident can be a pharmacy FWA incident. The pharmacy risk predictive modeler 1507 identifies the data types in the claims database 1501 that are predictive of FWA by a pharmacy. These data types are used as features in the pharmacy FWA predictive mode to be stored in the FWA model storage 1509.

The system 1500 can send the patient risk predictive model, the prescriber risk predictive model and the pharmacy risk predictive model for storing in storage 1509 and for use in an FWA processor to apply the models to prescription data to determine a likelihood of fraud waste or abuse of a prescription drug system. The application of the models loaded in the FWA processor can be used on data different than the training data used to develop the models. The difference can be a difference in time or a difference in data. The models are portable and can be applied to different data. In an example embodiment, the FWA processor applies at least one of the patient risk predictive model, the prescriber risk predictive model and the pharmacy risk predictive model to prescription data at least partially outside the first-time period, the second-time period and the third-time period to predict the likelihood of fraud, waste or abuse of the prescription drug system.

Each of the modelers 1503, 1505, 1507 are used to reduce the number or potential features that equals all of the data types in the database 1501 to a reduced set of features. The features may be different for each of the patient model, the prescriber model and the pharmacy model. The number of features may be a third or less of the total number of data types. The number of features may be a tenth of the total number of data types. The number of features may be an order of magnitude or two orders of magnitude less of the total number of data types. The number of features may be a single digit percentage of the total number of data types, e.g., less than ten percent. The features may include values that are calculated from two or more data types.

The FWA processor 1511 can select any of one of the patient risk predictive model, the prescriber risk predictive model and the pharmacy risk predictive model among a plurality of available predictive models based on a type of risk score being determined. The processor loads the selected one of the patient risk predictive model, the prescriber risk predictive model, and the pharmacy risk predictive model to generate FWA predictive risk scores 1513. The processor can apply any of the models over different time period of data in the database 1501. When the patient risk predictive model is loaded in the FWA processor 1511, the FWA processor 1511 uses the patient risk predictive model and the claims data to calculate a patient risk score over a first evaluation time period. When the prescriber risk predictive model is loaded in the FWA processor 1511, the FWA processor 1511 uses the prescriber risk predictive model and the claims data 1501 to calculate a prescriber risk score over a second evaluation time period. When the pharmacy risk predictive model is loaded in the FWA processor 1511, the FWA processor 1511 uses the pharmacy risk predictive model and the claims data 1501 to calculate a pharmacy risk score over a third evaluation time period. The evaluation time periods can be different time periods. In an example, the time periods can be the preceding year, the preceding quarter, or the preceding month.

The processor is to compare the calculated one of the patient risk score, the prescriber risk score, the pharmacy risk score, or a combination thereof to determine violation of a risk threshold and to send a risk flag to a client device when a risk threshold violation by the one risk score is determined. The risk flag can be a graphic indicator that a risk score has exceeded a threshold value or that an unacceptable risk has been determined by the FWA processor.

Figure 16:
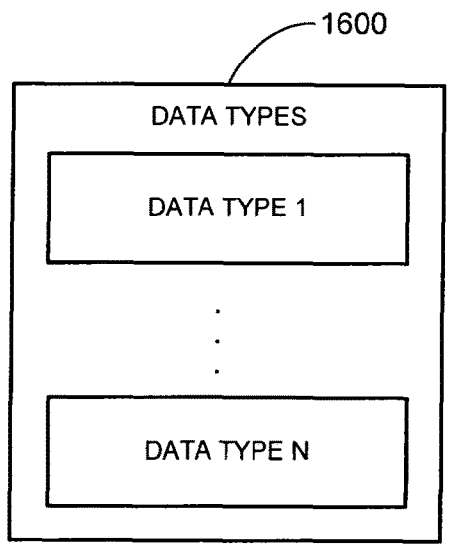
FIG. 16 is a schematic view of data types that can be part of the claims data, according to an example embodiment.

FIG. 16 shows a schematic view of a database 1600, which can be stored in the database 114. The database 1600 includes a plurality of data types, $1601_1, 1601_2, \ldots 1601_{N-1}, 1601_N$ that are each a potential feature in at least one of the FWA models. The modelling described herein will filter the data types to decide which of the data types are indicative of potential FWA. In an example, the data types $1601_1$ and $1601_N$ are included in the model as indicative of FWA; the data types $1601_2$ and $1601_N$ are excluded from the model.

Examples of data types 1601 that become features in the patient model of opioid FWA include benzodiazepine (benzo) consumption, number of unique prescriber and pharmacy combinations per therapy, morphine equivalent dose, opioid claims per pharmacy, refill too soon reject transactions, paid claim amount, sleep claims per pharmacy, number of days between earliest opioid fill and most recent opioid fill, distance traveled for opioids, duplicate therapy, claims, number of unique prescribers for control substances, concomitant opioid and suboxone consumption, brand claims, chain pharmacy usage, control substances, emergency room prescriber usage, night claims, claims where the pharmacy and doctor are not in the same state, number of submitted and then reversed transactions, and the like, Data types that are not used as features in this model include age, prior authorizations, specialty drug claims, maintenance utilization, gender, line of business, name, and the like.

Examples of data types 1601, in another example embodiment, that become features in the patient model of opioid FWA include percent of reversed transactions in the past X days, percentage of control substance claims, percentage of claims at chain pharmacy that are opioids, percentage of claims that are brands, average number of unique doctor/pharmacy combinations per generic code number ("gen") in the past year, number of duplicate therapy claims, percentage of emergency room doctors who are writing for opioids, number of days between first opioid claim and latest opioid claim, average morphine equivalent dose per day, total distance between the pharmacy and doctor for opioids, average number of refill too soon rejects for opioids per doctor, average number of sleep claims per sleep dispensing pharmacy, average dollar value per paid claim, binary flag of whether the member has taken an opioid and a suboxone prescription in the same thirty day window, percentage of claims where the pharmacy and doctor are not in the same state that are opioids, percentage of night claims that are opioids, average number of opioid claims per opioid dispensing pharmacy in past X days, average number of benzodiazepine claims per benzodiazepine writing doctors, binary flag of quarter over quarter increase in number of unique control substance doctors, and the like. This list is not exhaustive of the features that can be used in the patient risk score model for opioids.

The prescriber risk model may include data types 1601 as the features therein, including single source brand claims, distance (prescriber to patient), patient traveling out of state, refill too soon rejects during adjudication, paid claim amount, reversals, morphine equivalent dose, benzodiazepines prescribed, compounded drugs, opioid patient gender, number of pharmacies dispensing control substances, and the like. Other data types may not be part of this model. Examples may include line of business, patient age, prior authorizations, drug utilization review and the like.

Data types 1601 used as the features used in a prescriber FWA risk score for opioids may include a number of unique pharmacies dispensing a prescriber's control substances divided by number of unique pharmacies dispensing all of prescriber's claims (a computed from value from other data values in the database), percentage of opioid patients at a prescriber who are male, average morphine equivalent dose per day over a prescriber, average number of brand claims per member at a prescriber, percentage of claims that are compounds from a prescriber, average number of claims where the prescriber's patients are attempting to skip a prescription drug monitoring program, average number of miles between the patients and a prescriber for controls over the past Y days, prescriber's average paid claim amount, binary flag of whether the prescriber's morphine equivalent dose is increasing quarter over quarter for the past year, prescriber's number of refill too soon rejects for opioid prescriptions divided by the number of unique refill too soon reject opioid members, prescriber's average reversals per member in the past X days, prescriber's number of benzodiazepine prescriptions in the past year, and the like.

Examples of data types 1601, in another example embodiment, that become features in the pharmacy risk score model of opioid FWA include number of days between service and adjudication, high cost brand medications as fills, percentage of doctors claims that are high cost brand medications, whole number billings, benzodiazepines, control substances, compounding, reversals and the like. Examples of data types not used in the pharmacy risk score model include patient gender, number of doctors, pharmacy state, refill rate and the like.

Figure 17:
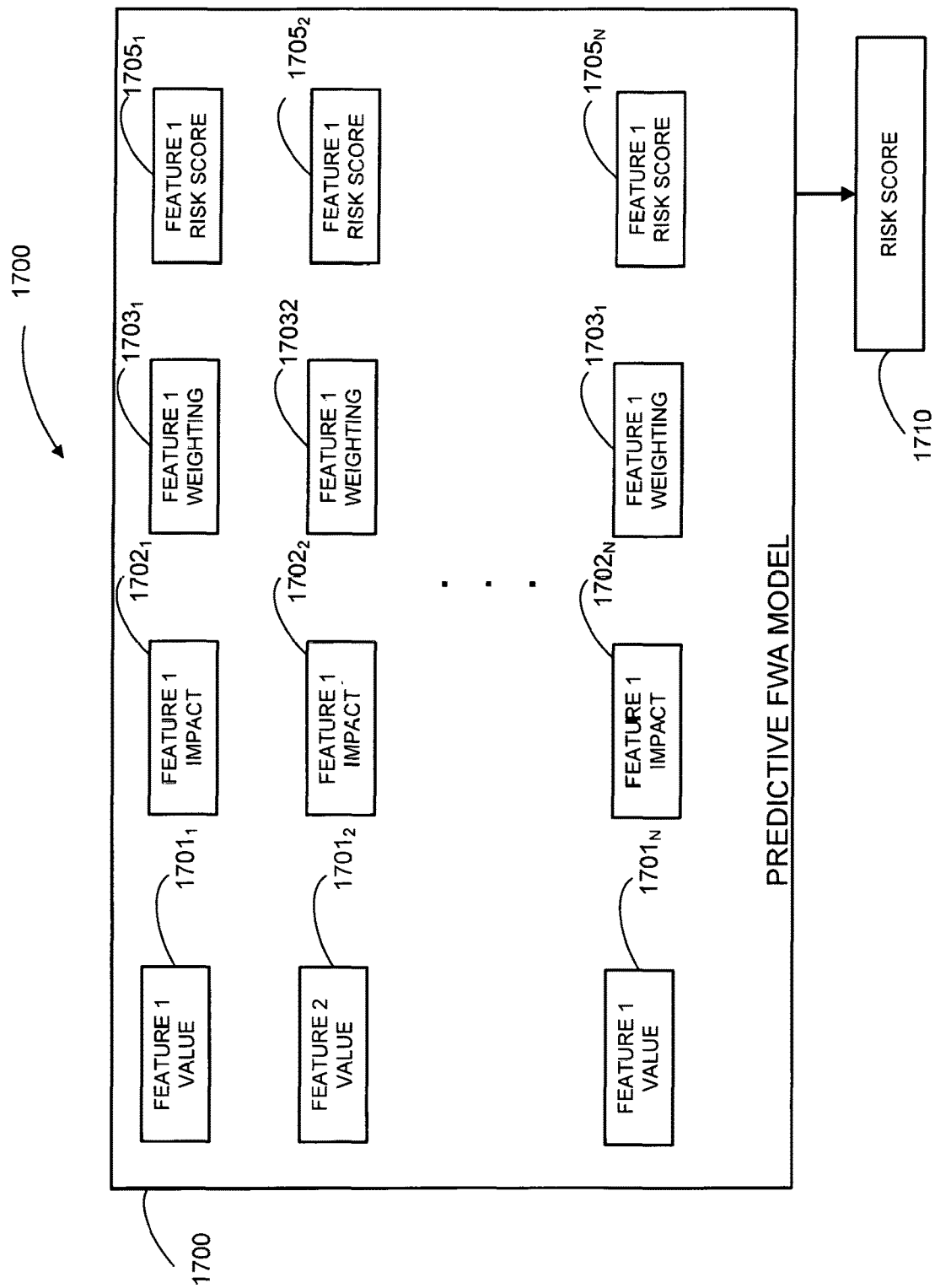
FIG. 17 is a schematic view for determining a predictive model risk score, according to an example embodiment.

FIG. 17 shows a schematic view of a predictive FWA model 1700 that uses a plurality of features values $1701_1$, $1701_2, \ldots 1701_M$. M equals the number of features selected from the number of data types N, where M is less than N in an example embodiment. In an example embodiment, M is at least an order of magnitude less than N. In an example embodiment, M is at less than one-hundredth of N. That is, at most one out of one hundred data types are used as features in the model. The number of data types can range from thousands to millions or more. Such a large number of data types precludes efficient operation of analyzing all of the data in all of the data types. The present methods and systems select only those data types as features that are determined to be indicators of FWA. The feature value $1701_1$ is used in the model and can be numerical value for purposes of computing a score. If the feature value is a binary value or other non-numerical value, then that value is converted to a numerical score for purposes of computing the risk score. The feature value $1701_1$ can be modified using at least one of feature impact $1702_1$ and feature weighting $1702_1$. The feature impact 1702 is a parameter that indicates that the feature value 1701 with a greater variable value has greater risk score. The feature impact values $1702_1$, $1702_2, \ldots 1702_M$ can be different for each of the feature values $1701_1, 1701_2, \ldots 1701_M$, respectively. The inverse can also be true, e.g., a lower feature value results in a higher risk score, which can be set by the feature impact value 1702. The feature impact value 1702 determines how the feature value will be used in the calculation of the risk score. The weighting parameter 1703 provides a fixed weight for the feature values 1701. The weighting value $1703_1$, $1703_2, \ldots 1703_M$ can be different for each of the feature values $1701_1, 1701_2, \ldots 1701_M$, respectively. The weighting factor can make relative rankings of the feature values 1701 for use in the risk score. Some features might be determined to have a greater indication of the likelihood of FWA than others, these features may receive a greater weight parameter 1703 than other features 1701. The weighting parameter 1703 can also be used to normalize the feature values $1701_1$, $1701_2, \ldots 1701_M$ to each other to give more equal weights to features values that have a lower absolute numerical value but have the same predictive capability as another numerical value for another feature (e.g., feature value $1701_2$) that is less than the weighting for the first numerical feature value $1701_1$. Each feature value $1701_1, 1701_2, \ldots 1701_M$ when modified for impact and weighting results in a feature score $1705_1, 1705_2, \ldots 1705_M$. The feature score $1705_1$, $1705_2, \ldots 1705_M$ represent the numerical score that an individual feature contributes to overall risk score 1710 for the present, predictive FWA model 1700. The model 1700 can be any model described herein, e.g., a patient FWA risk model, a patient opioid FWA risk model, a prescriber FWA risk model, a prescriber opioid FWA risk model, a pharmacy FWA risk model, a pharmacy opioid FWA risk model, and the like. The risk score 1710 can be a sum of the features scores $1705_1, 1705_2, \ldots 1705_M$. The risk score 1710 can be another algebraic function of the features scores $1705_1$, $1705_2, \ldots 1705_M$.

The present risk scores can be used to identify drug classes in which there is a greater risk of FWA. The higher the scores in any one of the patient, prescriber, or pharmacy risk score across a time period related to a specific class of drugs may indicate that that type of drug should be reviewed more carefully for possible FWA. This can be flagged in an output from the system, e.g., to a client device 150 or to a display device within the PBM system. The number of risk scores that exceed a threshold and include a drug that is part of a same class can be used to focus FWA investigation efforts. On a normalized basis, a first drug type, e.g., benzo drugs or opioid drugs, may be present in about one-third of the FWA cases. The models can be built to put a greater emphasis on the first drug type, e.g., by increasing the weighting or the feature impact for the features related to the first drug type relative to other drugs. In an example, the weighting for the first drug type can be set at thirty-three times the value of a drug type that has not been part of a FWA incident. Another drug that may need to have a greater emphasis in determining risk scores is gabapentin, which can be a second drug type. On a normalized basis, the second drug type, e.g., gabapentin, may be present in about one-sixth of the FWA cases. The models can be built to put a greater emphasis on the second drug type, e.g., by increasing the weighting or the feature impact for the features related to second drug type relative to other drugs. In an example, the weighting for the second drug type can be set at about sixteen times the value of a drug type that has not been part of a FWA incident. A third drug type, e.g., ADHD medications, can be set at about two times a non-FWA drug type. A fourth drug type, e.g., bupropion, can be set at about three times a non-FWA drug. A fifth drug type, e.g., a muscle relaxant drug, can be set at about eight times a non-FWA drug. The non-FWA drug can be drug type that is least likely to be part of a FWA event. The weight of the non-FWA drug can be set to one times, or the normalization value.

Figure 18:
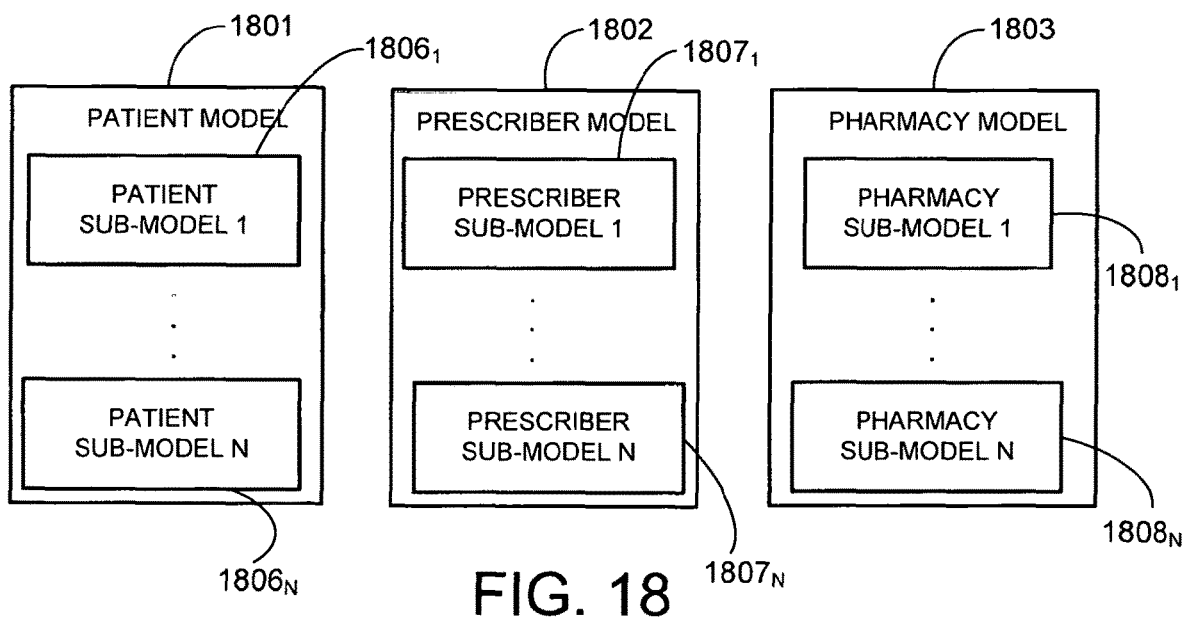
FIG. 18 is a schematic view of model types that can be generated using the methods and systems herein, according to an example embodiment.

FIG. 18 shows a schematic view of the models 1800 that can be derived from known FWA. These models use features that are determined from data that predates the known FWA. The data types that are predictive of the FWA are used as features in the predictive model. The predictive models include, but are not limited to a patient model 1801, a prescriber model 1802, and a pharmacy model 1803. Each of these can be used to calculate a risk score. The models 1801, 1802, and 1803 can also each include sub-models. The sub-models $1806_1, \ldots 1806_N$ are sub-models that are all patient risk models. The patient sub-model $1806_1$ can be directed to evaluate a patient opioid risk score. The patient sub-model $1806_N$ can be directed to evaluate a different patient risk score than the patient opioid risk score. The sub-models $1807_1, \ldots 1807_N$ are sub-models that are all prescriber risk models. The prescriber sub-model $1807_1$ can be directed to evaluate a prescriber opioid risk score. The prescriber sub-model $1807_N$ can be directed to evaluate a different prescriber risk score than the prescriber opioid risk score. The sub-models $1808_1, \ldots 1808_N$ are sub-models that are all pharmacy risk models. The pharmacy sub-model $1807_1$ can be directed to evaluate a pharmacy opioid risk score. The pharmacy sub-model $1807_N$ can be directed to evaluate a different pharmacy risk score than the pharmacy opioid risk score.

The sub-models can be directed to individual pharmacy benefit plans. In en example embodiment, a set of sub-models for each of patient risk model, prescriber risk model, and pharmacy risk model can be determined for each of Medicare, Medicaid, Department of Defense (DOD) plan, commercial health plans. Thus, each of these can have a sub-model specific to the FWA that may occur in each individual plan. Some features may overlap between sub-models for these individual plans. Each plan may have at least one feature that occurs in its plan, e.g., a DOD directed risk sub-models, and not in other plans, e.g., a commercial plan.

In an example, the features used in the models 1801, 1802, 1803 may depend on geographic location, which can be included into the data. Different FWA may be more likely to occur in certain locations. For example, FWA in a first location, e.g., New York City, may involve high-cost, single-source medications, e.g., Abilify or Seroquel. A sub-model 1806, 1807, 1808 for any of the patient risk score model, a pharmacy risk score model and the pharmacy risk score model may be developed that weighs the single source medication more heavily when any of the patient, prescriber, or pharmacy is in New York City. The sub-model may be different between the patient model, the prescriber risk model and the pharmacy risk model. The development of the models described herein may determine that the pharmacy location is not a feature for pharmacy risk score model, but is a feature for the patient and pharmacy risk score models. Moreover, the weighting of the single source medication may be different in each model. In developing the pharmacy model, it may be determined that a pharmacy in a second location, e.g., recently in Florida, phantom pharmacies are a greater risk than in other locations in the United States. A phantom pharmacy is a pharmacy that sets up shop, bills as much as it can for as long as it can and then will disappear. Thus, a location in Florida, based on historical data, may be a feature that weighted more heavily or included at all in a pharmacy FWA risk score model.

The FWA predictive risk models can include a plurality of features, these features can be individual to one of the predictive risk models. Some of the features may overlap, e.g., a location feature may be used across more than one predictive risk model. The pharmacy risk predictive model may include a plurality of features to calculate the risk score. These features can include service and adjudication feature, a high cost brand medications feature, a whole number billing feature, a benzodiazepine feature, a control substance feature, a compounding feature, and a reversals feature. The patient predictive risk model may include a benzodiazepine consumption feature, a therapy feature, a morphine equivalent dose feature, a pharmacy feature, a transactions feature, an amount feature, an opioids feature, a suboxone consumption feature, a chain pharmacy usage feature, an emergency room prescriber usage feature, a reversed transactions feature, and a same state feature. The prescriber predictive risk model may include a service and adjudication feature, a high cost brand medications feature, a compounding feature and a reversals feature. It some example embodiments the reversals feature may be used in more than one predictive risk model. The reversals feature may have different weightings or different feature impact for calculating the risk score for any one of the patient risk score, the prescriber risk score, and the pharmacy risk score.

A sub-model may be directed to predicting the likelihood of opioid FWA. The sub-model may be directed generally to FWA by generating an FWA opioid risk score using a model that crosses over patient, prescriber, and pharmacy features. An opioid predictive model may increase its weights for each opioid related feature relative to other models. The features that relate to opioids may all be selected for inclusion into the opioid sub-model. In an example, attempted opioid prescription fills by a patient may be a feature that has an increased weight or higher feature impact in this example. The number of opioid prescriptions written by a prescriber may be a feature that has an increased weight or higher feature impact in this example. The number of opioid prescriptions written by a prescriber at night may be a feature that has an increased weight or higher feature impact in this example. The number of opioid prescriptions filled by a pharmacy may be a feature that has an increased weight or higher feature impact in this example. The number of opioid prescription reversals at a pharmacy may be a feature that has an increased weight or higher feature impact in this example. These features can be combined in to an opioid FWA model that provides an overall opioid risk score. These features can also be part of a patient model, a prescriber model and/or a pharmacy model.

Figure 19:
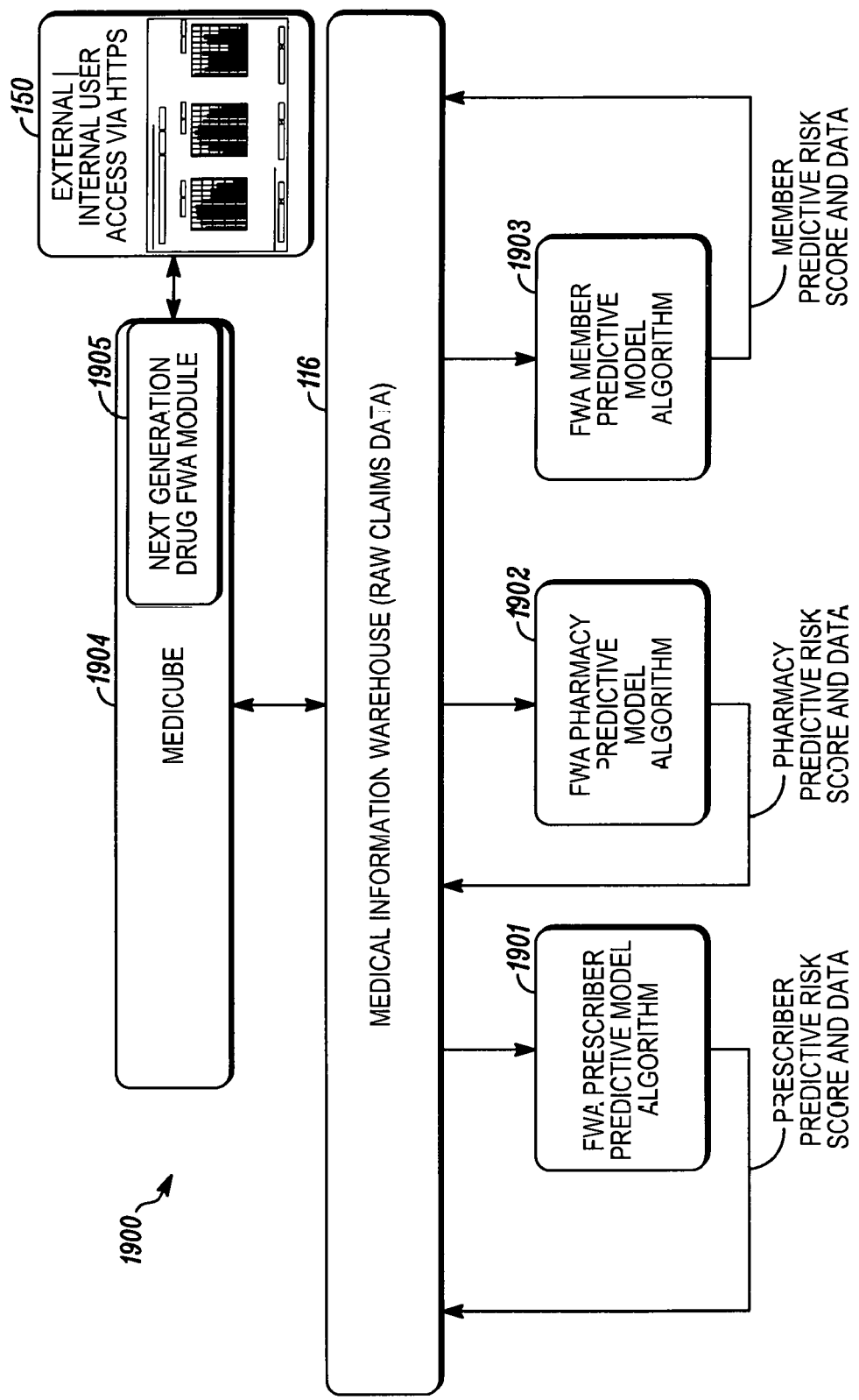
FIG. 19 is a schematic view of a FWA system, according to an example embodiment.

FIG. 19 shows a system 1900 for determining and using FWA risk score models and risk scores produced by the models. A database containing drug related data is stored in a database 116. The FWA prescriber predictive risk model 1901 can be derived from known incidents of FWA as described herein. The prescriber model 1901 can include an algorithm that interprets the data in the database 116 to produce a prescriber risk score. The prescriber model may include the feature impact and weighting as described herein. The FWA pharmacy predictive risk model 1902 can be derived from known incidents of FWA as described herein. The pharmacy model 1902 can include an pharmacy risk algorithm that may include weighting and feature impact as described herein. The pharmacy model 1902 interprets the data in the database 116 to produce a pharmacy risk score. The FWA member predictive risk model 1903 can be derived from known incidents of FWA as described herein. The member can be a patient that is part of a pharmacy benefit plan as provided by a client and managed by a pharmacy benefit manager. The member model 1903 can include a member risk algorithm that may include weighting and feature impact as described herein. The member model 1903 interprets the data in the database 116 to produce a patient risk score. A master device 1904 includes an interface generator as part of the FWA system (including processor circuitry) 1905 that can receive requests from external user devices for reports in the form of graphics related to FWA results from the predictive model results.

The master device 1904 can reconcile the data in the database and activate the models 1901, 1902, and 1903. The master device 1904 can instruct the models to run on a schedule, e.g., every two weeks or more. The master device 1904 can also focus the models on certain members, prescribers or pharmacies. In an example embodiment, the master device 1904 runs the models 1901, 1902, and 1903 on all of the data. The risk score calculations from each of the models 1901, 1902, 1903 can be stored in the database 116. The master device 1904 can access the currently calculated risk scores and the previous risk scores to determine trends in the scores.

The master device 1904 can operate on the data in the database 116, before the models 1901, 1902, 1903 calculate risk scores using the database 116. The master device 1904 can operate to clean the source data and/or creating the master data, which may enable more complete and accurate pulls of claims data to determine the models 1901, 1902, 1903 and compute risk scores. The cleaned data relating to demographics, employer type, practitioners, health, benefits, prescriptions and health claims can be used as features in the models 1901, 1902, 1903. Other data types that can be used as model features can include age, gender, or family. Other data types that can be used as model features can include prescriber (e.g., practitioners) utilized, employer, SIC, and health plan, diagnoses history, prescriptions, drugs, prescribers, count, and amount history, medical claims history, and controlled substance prescribing patterns.

The prescriber model 1901 can use the data types of demographics, specialties, business relationships, health plans, prescribing profile patients, patient demographics, diagnoses, prescribing pattern, drugs, type, variation from standards for each practitioner specialty, patient demographics per practitioner, (e.g., percent practice load by age groups, ratio of practice load or relative practice load), percent of prescriptions linked to each age group, most common diagnoses and procedures for each practitioner specialty, associations with health plans, practitioners, medical groups, PPOs, hospitals, controlled substance prescriptions compared to specialty type adjusted for patient age and gender, health claims history and analysis, and long-term prescribing patterns related to controlled drugs, and procedures as model features.

The pharmacy model 1902 can use data types of analysis of demographics, ownership, locations, pharmacists, prescription profile, practitioners, clients, patients, ownership, pharmacists, locations, profile of controlled substances dispensed by class codes, profile of high-volume practitioners by type of drug, health plans serviced, PPO network relationships, and patient demographics as model features.

The FWA system 1905 can operate to integrate the FWA results and can correlate the risk scores from the models 1901, 1902, 1903 with other data in the database to produce a graphical user interface on the display device 150. The FWA system 1905 can also use the thresholds for FWA risk scores to display when the risk score is nearing or exceeding the threshold. The other data that is related to the computed risk scores can include analysis of health plan, administrator, prescriber, pharmacy, errors, fraud, waste, abuse, misuse, and utilization. The integrator can also relate the risk scores to commercial plans drug send and count; Medicare plan's drug spend and count; Medicaid plan's drug spend and count; controlled drugs by category, spend, and quantity; uncontrolled drugs with high value by drug type, spend, and quantity; selected generic drugs by drug type, spend, quantity; selected patent drugs by drug name, spend, and quantity; average cost per prescription for each drug group type; average age per patient for each drug group type; mode for age of prescribing (the age peak); mine each prescription claim for prescriber/billing org/health plan/address relationships; drug over utilization; and drug under-utilization.

The FWA system 1905 can also generate, format, and present a graphical user interface that shows an analysis health plan, administrator, practitioner, diagnoses, errors, fraud, waste, abuse, misuse, and utilization. A user device can use the graphical user interface to mine each medical claim for diagnoses, procedures and practitioner/billing org/health plan/address relationships and tax ID, NPI, PPO network, and the like; diagnoses profiles by practitioner specialty, and claims demographics; geography, age group, gender, employer and member demographics, practitioner network, benefit plan, practitioners, prescription profile, medical profile, and loss ratio.

The FWA system (i.e., integrator) 1905 can also output raw data, which can be corrected data by the master device 1904. The FWA system 1905 can also calculate and display trends related to the risk scores. For example, the risk scores from the models 1901, 1902, 1903 can be display over time. In an example, each score is calculated on a biweekly basis. The FWA system 1905 can display the past years risk scores, e.g., twenty-six scores on the graphical user interface on device 150.

The FWA system 1905 can also output risk scores modified or filtered by population analysis includes demographics, geographic, employer types, practitioner practice by specialty, health, benefit plan design, prescribing patterns, health claims, and diagnoses. The FWA system 1905 can also output risk scores modified or filtered by demographics that may define numbers and percentages for predefined age-gender groups (e.g., 0-9, 10-17, 18-24, 25-34, 35-44, 45-54, 55-64, 65-74, 75+); diagnoses analysis that enable section of diagnoses metrics in order of relevance to fraud and abuse; utilize ICD-Age-Gender associations, health indicators that includes health scores can be performed based on major indicators of risk, fraud and abuse; waste and over utilization including a number of events identified as waste, over-utilization, frequency for each; restricted drugs analysis; and high-cost drugs analyses.

The FWA system 1905 can also modify or filter the risk scores by health plan member (patient) information including plan benefits, claims history, and provider choices. Examples of further information that can used to modify the display on the graphical user interface can include access plan benefits and co-pay and out-of-pocket expense status; claims history; and provider finder.

In some embodiments, the FWA system 1905 can produce an output for a graphical user interface with risk scores and associations between providers including individual physicians, practice groups, and hospitals. The associations may include current and historical information on contractual arrangements and business relationships of a given provider (e.g., an individual or an organization) with other providers. For example, one elements of the GUI may determinate an association between individual practitioners related to practice groups. In some embodiments, matching may be performed on an address and phone number to among the master data to identify different prescribers at the same physical address and thereby having an association. Such associations may be saved in the master data in the database 116 and, in some embodiments, be referenced as related records.

In an example embodiment, a plurality of data attributes of comparison data and the plurality of data attributes of a master record as stored in database 116 or determined by device 1904 are respectively compared to determine that there is a difference, the comparison data originating from a data source. A relative level of source priority of the data source of the comparison data is determined relative to the data source of a current state version of the master record in accordance with source evaluation criteria. The current state version of the master record is stored in reference data based on a determination that there is a difference and that the source priority of the data source of the comparison data is equal to or greater than the data source of the current state version of the master record. Mapped comparison data is used to update the current state version of the master record based on the determination that there is a difference and that the source significance of the data source of the comparison data is equal to or greater than the data source of the current state version of the master record to create an updated state version of the master record, the mapped comparison data being based on the comparison data.

The device 1904, in an example embodiment, can clean and process claims data are described. A method includes accessing a first source of claims data. The method also includes accessing a second source of claims data. The second source of claims data may be a cleaned version of the first source of claims data. The method may also include receiving additional data. The method used by the device 1904 may also include accessing transformations information that reflects a plurality of data transformations in the first source of data to the second source of data. The method may further include identifying transformations relevant to the additional data.

The device 1904 may also include receiving claims data, and comparing one or more attributes of the claims data to data attributes included within a master data set. The method may also include identifying a difference between the one or more attributes of the claims data and the data attributes included within the master data set. The method may also include identifying a transformation to correct the difference between the one or more attributes of the claims data and the data attributes included within the master data set. The method may further include applying the transformation to the one or more attributes of the data to generate corrected data, and storing the corrected data in the master data set and storing the original/as-is data, corrected data and transformation data in a source data set.

Figure 20:
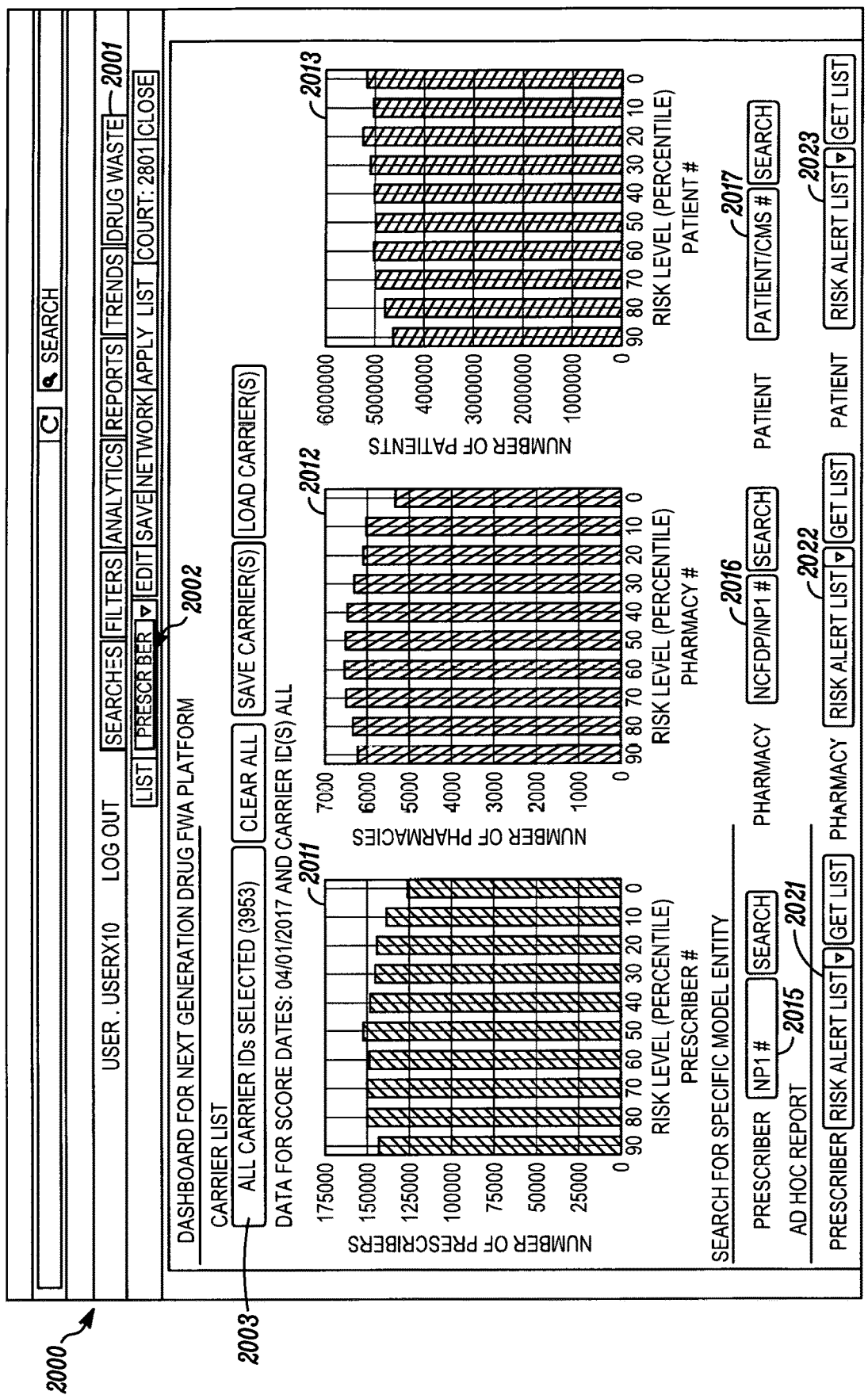
FIG. 20 is a dashboard display for FWA risk scores, according to an example embodiment.

FIG. 20 shows a dashboard 2000 as part of a graphical user interface as described herein. The dashboard 2000 can be on a device, e.g., the client device 150, which uses FWA risk scores. The dashboard is selected from a plurality of options for output by the master device 1904. The dashboard 2000 is selected as a FWA output graphic. Other outputs can include searches, filter, analytics, reports and trends, all based on the data in the database 116. These can be selected at tabs 2001. An input box allows the type of risk score to be selected from the patient, prescriber, or pharmacy risk scores. In dashboard 2000, the prescriber risk score is selected. A prepopulated list is selected at input box 2003. The risk scores for the selected list of carrier IDs, shown in graphic boxes, are graphs 2011, 2012, 2013, which correspond to risk scores from the prescriber model 1901. The graphs are calculated for a set period, here shown as at date, e.g., Apr. 1, 2017. The graph 2011 is a graph of the number of prescribers (on the ordinal) sorted by percentile of risk level (abscissa). The risk scores in the prescriber risk score graph 2011 are calculated using the prescriber model 1901. The graph 2012 is a graph of the number of pharmacies (on the ordinal) sorted by percentile of risk level (abscissa). The risk scores in the pharmacies risk score graph 2012 are calculated using the prescriber model 1902. The graph 2013 is a graph of the number of patients (on the ordinal) sorted by percentile of risk level (abscissa). The risk scores in the patient risk score graph 2013 are calculated using the prescriber model 1903. The dashboard 2000 includes inputs for entity searches. A prescriber search box 2015 allows the input of a prescriber name or identification number to allow the search of a specific prescriber. A pharmacy search box 2016 allows the input of a pharmacy name or pharmacy identification number to allow the search of a specific pharmacy. A patient search box 2017 allows the input of a patient name or patient identification number to allow the search of a specific patient. When the search is performed, then the risk data for that specific search is displayed on the GUI. The dashboard 2000 can also run reports on the risk score data. Report search input boxes 2021, 2022, 2023 allows a selection of a stored report to be run for one of the prescriber risk scores (e.g., a drop down list in prescriber box 2021), the pharmacy risk scores (e.g., a drop down list in pharmacy box 2022) and the patient risk scores (e.g., a drop down list in patient box 2023). In the illustrated example of the dashboard 2000, the risk alert list report is the shown report in each of the prescriber box 2021, the pharmacy box 2022, and the patient box 2023, for selecting a report. If the get report selectable icon is selected the master device 1904 or the integrator 1905 will produce the selected report, e.g., the risk report of the prescriber risk scores, the risk report of the pharmacy risk scores, or the risk report for the patient risk scores. The risk reports can be based on a plurality of risk scores over a time period, e.g., twenty-six risk scores over the past year from the date selected in the dashboard 2000 or the produced the dashboard 2000.

Figure 21:
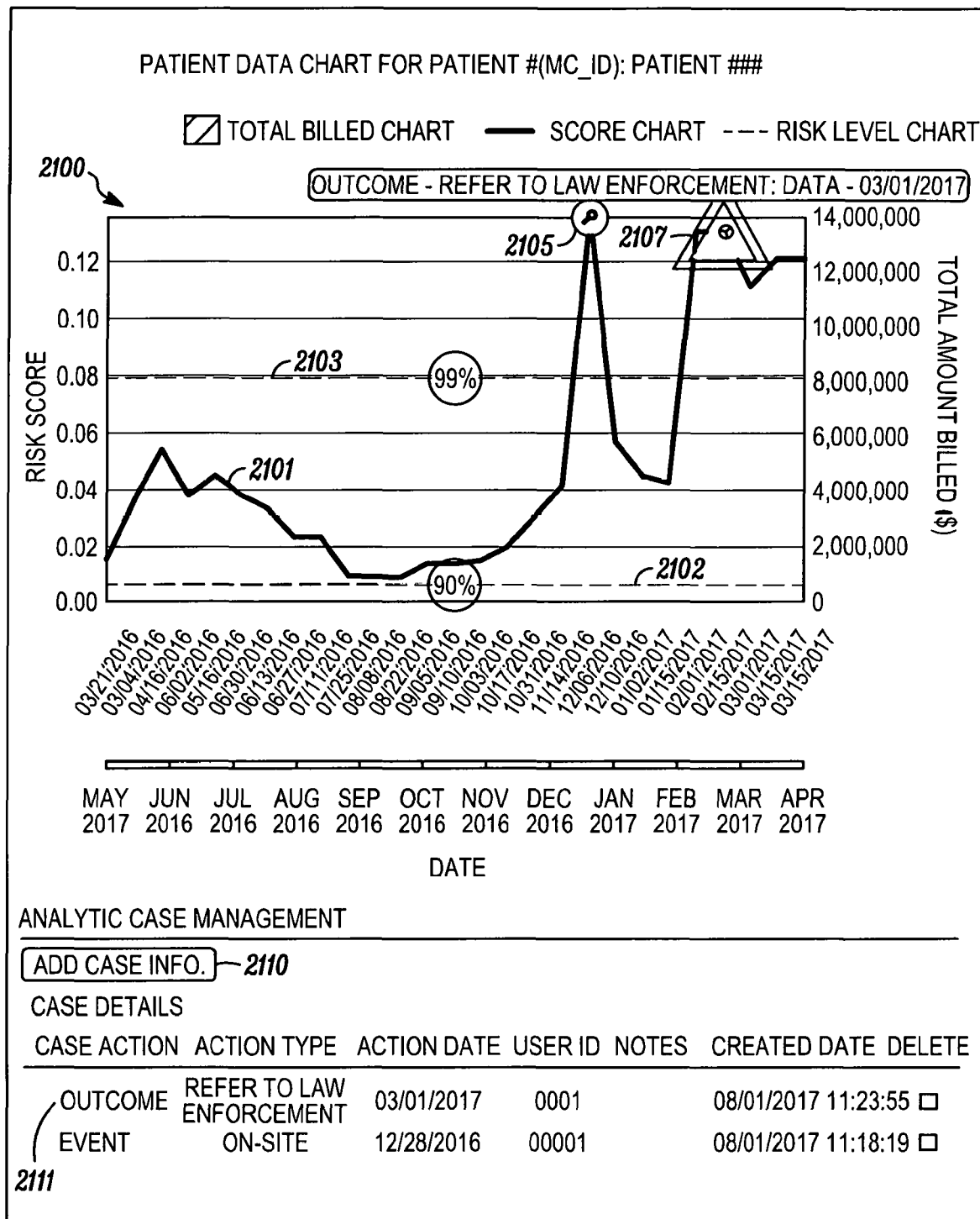
FIG. 21 is a dashboard display for FWA risk scores, according to an example embodiment.

FIG. 21 shows an example of a graphical user interface 2100 for a specific individual that has risk scores, e.g., a pharmacy risk score, a prescriber risk score, or a patient risk score. A patient has been selected for GUI 2100. However, similar graphs as part of the GUI can be generated using the corresponding model and the data time period. The risk scores are plotted against time to show line 2101. The percentile lines of ninety percentile and ninety-ninth percentile 2102, 2103, respectively, are shown to indicate the relative level of the risk versus the other patient risk scores. The lines 2102, 2103 can be threshold risk levels. At a time, the graph of risk score 2101 exceed the line 2103 and peeks at 2105. At the peak 2105, the flags of a serious FWA risk are triggered to indicate that an investigation should begin. This can show an event that occurs based on the application of the model to the data. The patient risk score on plotted line 2101 can be calculated as described herein. The risk score subsequently dips below the ninety-ninth percentile line 2103 after the investigation but does not dip below the ninetieth percentile line 2102. This dip can be the result of the intervention at 2105, e.g., intervention by staff using devices that can communicate electronically with the patient. The risk score again rises to another peak 2107 whereat the investigation that is triggered by the calculated risk scores and possibly with the GUI 2100 is referred to a law enforcement investigation. The peak value 2105 can be indicated with an icon. The law enforcement referral can also be indicated by a law enforcement icon. The GUI 2100 can also graph the total billed amount as the second ordinal on the same graph, e.g., in a different color than or different line type than the risk score. Similar graphical user interfaces can be produced using the prescriber risk scores or the pharmacy risk scores. An analytic case management field 2110 is provided in GUI 2100 to allow the entry and display of additional case information to be added and saved in the database 116. A case details field 2111 is provided in the GUI 2100 to show the events and/or outcomes, these can correspond to the icons added to the graph and provide additional data as to the work done on this patient (or other subject of a similar graph) in view of their risk score.

Figure 22:
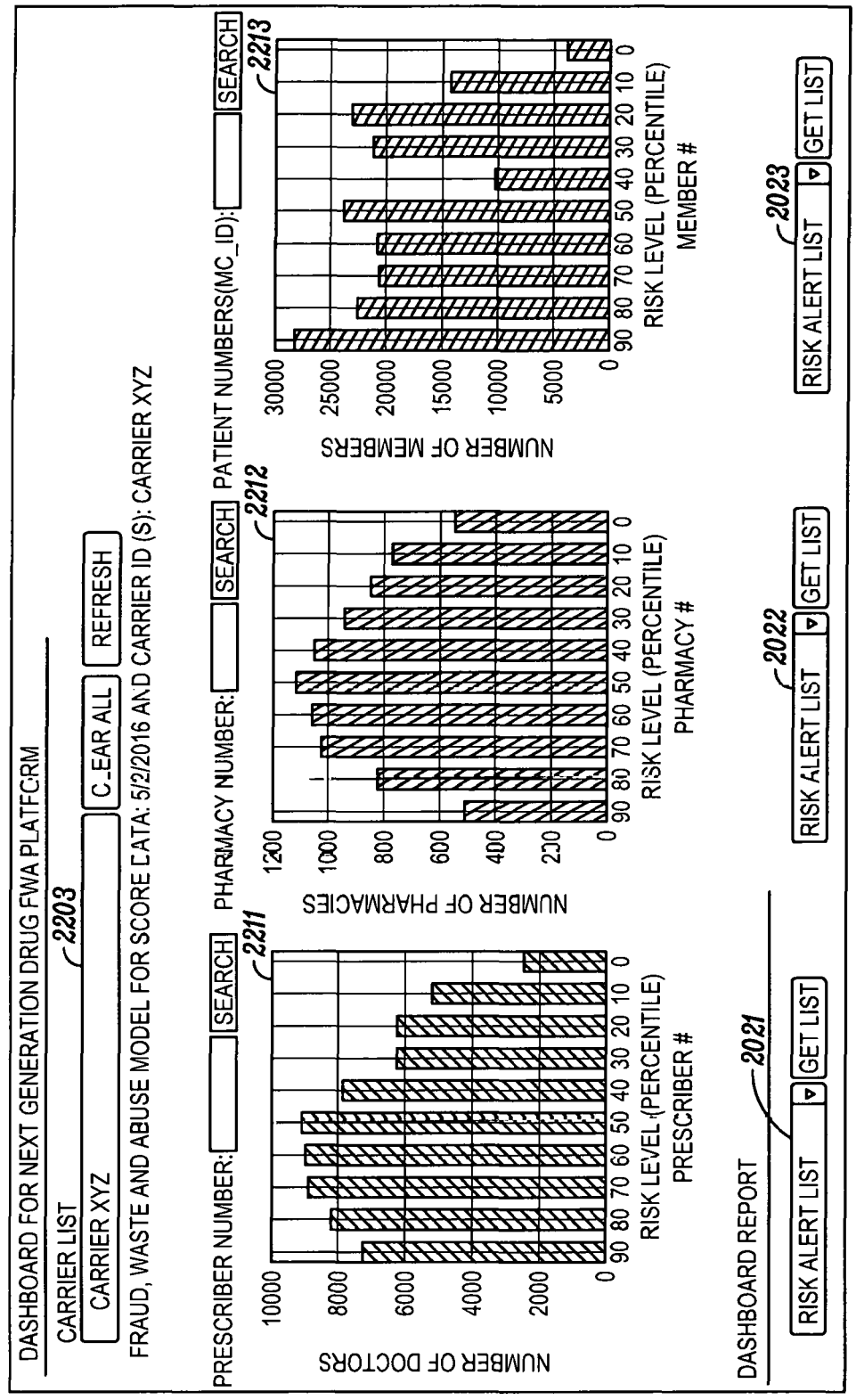
FIG. 22 is a dashboard display for FWA risk scores, according to an example embodiment.

FIG. 22 shows another dashboard 2200 as part of a graphical user interface, that is at least partially generated using the risk scores. The dashboard 2200 is similar dashboard 2000 but is based on different risk scores. A different carrier's list selection box 2203 shows different subjects than the carriers selection 2003, thus different risk score data forms the graphs 2211, 2212, 2213. The difference between graphs 2211, 22112 and graphs 2011, 2012 is the fewer number of prescribers and pharmacies that have are in the higher risk levels. Likewise the there are fewer patients in the higher risk categories in graph 2213 than in graph 2013. The number of available prescribers, pharmacies and patients may be different for any selected carriers list or may be a selected group that has lower risk scores.

FIG. 23 shows a graphical user interface of a report 2300 of the prescribers from dashboard 2000. Here the report 2300 shows the prescribers (which number 7267) with a ninetieth percentile risk score. The name, prescriber NPI number, address, city, state, zip, phone, risk level number of claims and total billed by the prescriber are shown. This data can be pulled from the database 116 by the master device 1904. The GUI with report allows the selection of charting a particular prescriber or return to the dashboard 2000 or 2200.

Figure 24:
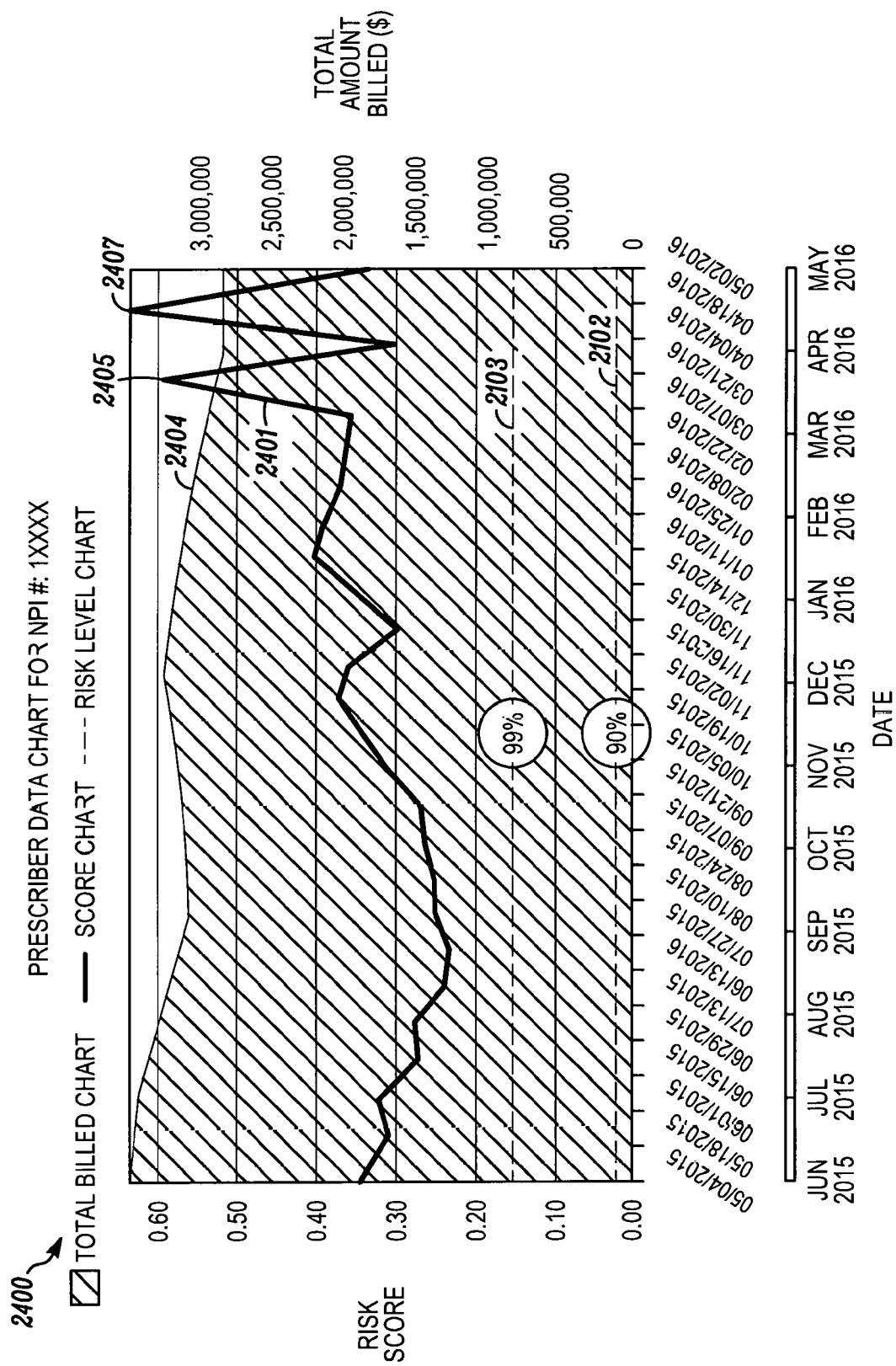
FIG. 24 is a dashboard display for FWA risk scores, according to an example embodiment.
Figure 25:
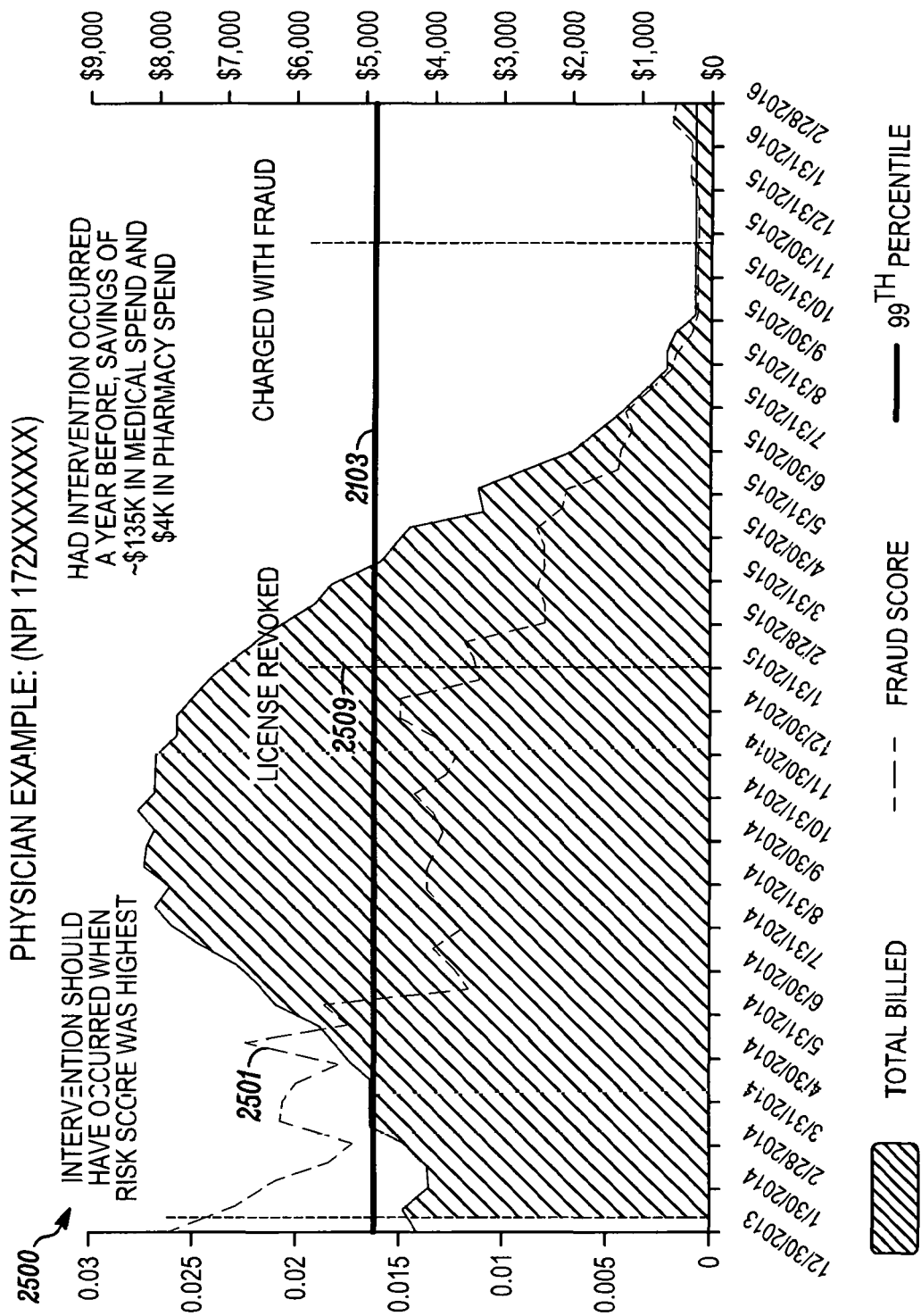
FIG. 25 is a dashboard display for FWA risk scores, according to an example embodiment.

FIG. 24 shows another GUI 2400 with a graph of the risk score 2401 and the total billed 2404 on the same graph 2400 for a selected prescriber from one of the prior GUIs, e.g., the report 2300 with John Doe 1 selected using the chart button. The chart is produced on the GUI 2400, e.g., by applying the prescriber model to the data stored in the system and retrieving additional data over a same time period. The risk level peaks at 2405 and 2407. The risk decreases after each peak, e.g., after an intervention by the system, e.g., requesting additional information from the prescriber system, flagging the prescriber, in-person visits and the like related to reducing FWA. The peaks 2405 and 2407 can also indicate a pattern of increased FWA, e.g., at a certain time of the year or in a pattern of FWA FIG. 25 shows another GUI 2500 that has the risk score 2501 and the amount billed (in thousands). It is desired to have an intervention or further investigation when the risk sore is highest, versus later in time. The earlier that the prescriber is investigated then the amount billed can be reduced and action against the prescriber's license to prescribe pharmaceutical drugs can move from the time 2509 to an earlier time if the investigation based on the earlier computation of the risk score so indicates.

Figure 26:
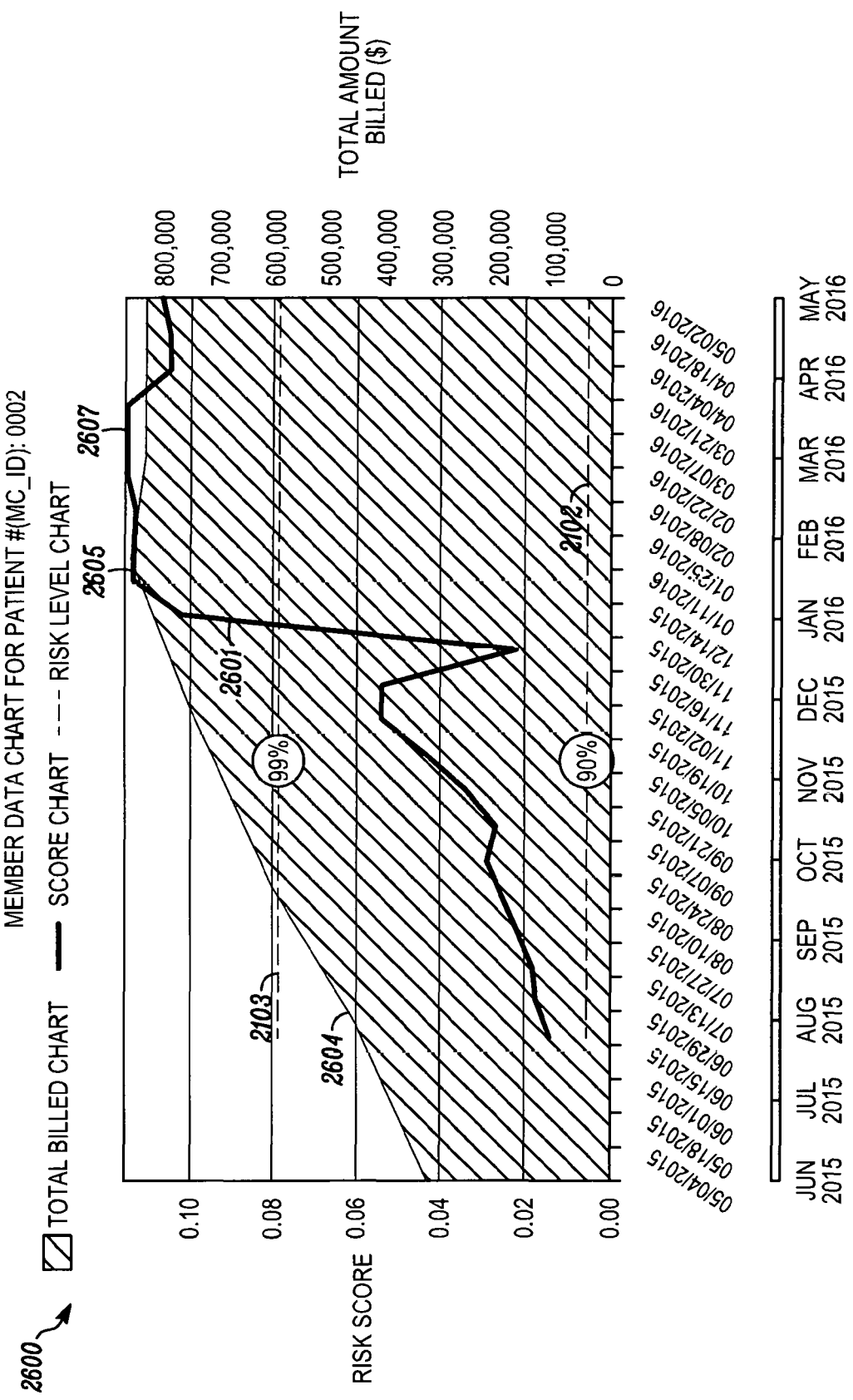
FIG. 26 is a dashboard display for FWA risk scores, according to an example embodiment.

FIG. 26 shows another GUI 2600 with a graph of the risk score 2601 and the total billed 2604 on the same graph 2600 for a selected patient from one of the prior GUIs, e.g., the GUI 2000 or 2200 with Patient Doe selected using a chart button. The chart is produced on the GUI 2600, e.g., by applying the member FWA model to the data stored in the system and retrieving additional data over a same time period (here, total billed). The risk level peaks at 2605 and 2607. The member risk shows a steep increase before the peak 2605 and crosses the threshold 2103. The member can be flagged in the system for intervention at each peak 2605, 2607 or at the steep rise ion risk score, which can indicate FWA of a pharmaceutical drug It is useful that the data used to create the risk score is associated with the correct entity. Thus, the claims data can be corrected or standardized before the model is generated or before the model is applied to the data to produce a risk score.

The claims data being used to deduce the models or on which the models operate can be data having a plurality of plurality of different types. The claims data includes adjudicated data and claims data that is submitted for adjudicated. The claims data includes prescription data that is rejected or reversed under the adjudication process. The claims data relates to patient, prescriber and pharmacies. The claims data that is used to develop a model can include all of the types of data. The data types that indicate or influence the likelihood of prescription or medical fraud, waste or abuse may be different for each of the plurality of models, e.g., the patient predictive risk model, the prescriber predictive risk model and the pharmacy predictive risk model. There can be some overlap in the types of data for each model. However, the models will have at least one different type of data in an example embodiment.

The dashboards and graphic user interfaces described herein can be generated based on the calculated results of possible FWA based on determined models from known FWA events as described herein. The dashboards and graphic user interfaces can be generated by integration of the data by the FWA interface system and displayed remotely on user devices with the protected health data being stored and protected remotely from the user devices.

The present description describes various embodiment for producing statistical models to interrogate a large database, e.g., over a billion prescription claim records, which each have tens to hundreds of different types of data associated with each claim and using the statistical models to further investigate the claims data to use a machine to determine likelihood of fraud, waste and abuse. The database may also store data related to over one million or over 1.3 million prescribers, over eighty million members (patients) and over seventy thousand pharmacies. In the past, identifying pharmacy fraud, waste and abuse meant having technicians and data researchers look at patterns of billing to identify outliers. The manual queries looked at whether a pharmacy dispensing too many of certain kinds of drugs and were the reversal rates for prescription refills too high or too low. However, the much effort was wasted looking at the wrong questions or the wrong data resulting too many false positives or allowing a significant amount of FWA to not be uncovered. The false positives also result in a significant number of rework, when not using the present predictive models. The use of the present systems and methods determines the types of data that should be looked at and establishes a model that is used to look for FWA patterns and likelihood in the data. The present description can provide further improvements in the understanding of what and who to look for when investigating FWA. The presently described systems and methods provide a new scheme that can only be performed in machines, e.g., due to the volume of data and data types. The features for a FWA risk score model can be automatically determined and then used to identify errors or patterns of fraud and abuse. The present description can be used to identify fraud, e.g., intentionally misusing the prescription drug system for monetary gain, or waste and abuse, e.g., intentionally misusing the prescription drug system.

The term "based on" or using, as used herein, reflects an open-ended term that can reflect others elements beyond those explicitly recited.

The phrase "fraud, waste and abuse" refers to excessive, fraudulent, or other nefarious use of the pharmacy drug system or medical system, e.g., attempts or successful fraudulent billing or prescription drug acquisition. Such nefarious actions can be for money or for access to restricted medications. Fraud, waste and abuse can be a type of illegal act involving the obtaining of something of value, either reimbursement in the pharmacy drug benefit plan or non-medical access to drugs, through willful misrepresentation. Fraud, waste and abuse can also include overutilization of services or other practices that, directly or indirectly, result in unnecessary costs to the health care system, including pharmacy benefit plans. In some instances, waste may not be criminally negligent actions, but can be a misuse of resources. In some instances, abuse may include payment for drugs or services when there is no legal entitlement to that payment and the individual or entity has not knowingly and/or intentionally misrepresented facts to obtain payment.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations. The methods described herein do not have to be executed in the order described, or in any particular order. Moreover, various activities described with respect to the methods identified herein can be executed in serial or parallel fashion.

A first example embodiment can use the models to detect a prescription drug fraud, waste or abuse by producing a score in a scoring system. The first embodiment can include a prescription drug adjudication database; a patient risk predictive modeler to access the prescription drug adjudication database and to discern a patient risk predictive model using prescription drug data in the database over a first time period that includes at least one known incident of patient fraud, waste or abuse; a prescriber risk predictive modeler to access the prescription drug adjudication database and to discern a prescriber risk predictive model using prescription drug data in the database over a second time period that includes at least one known incident of prescriber fraud, waste or abuse; a pharmacy risk predictive modeler to access the prescription drug adjudication database and to discern a pharmacy risk predictive model using prescription drug data in the database over a third time period that includes at least one known incident of pharmacy fraud, waste or abuse; and a model storage to receive the patient risk predictive model, the prescriber risk predictive model and the pharmacy risk predictive model for storing and for use in applying the models to prescription data to determine a likelihood of fraud waste or abuse of a prescription drug system.

The system of the first example embodiment can include the patient risk predictive model, the prescriber risk predictive model and the pharmacy risk predictive model being applied to prescription data at least partially outside the first-time period, the second-time period and the third-time period to predict the likelihood of fraud, waste or abuse of the prescription drug system.

The system of the any example can include the patient risk predictive modeler identifying types of data in the prescription data that indicate at least one of fraud, waste, abuse, or a combination thereof by a patient and setting patient risk predictive model features to be the types of data. The types of data indicate at least one of fraud, waste, abuse, or a combination thereof is fewer than all types of data.

The system of any example embodiment includes the patient risk predictive model features being less than one-third of the types of data.

The system of any example embodiment includes the prescriber risk predictive modeler identifying types of data in the prescription data that indicate at least one of fraud, waste, abuse, or a combination thereof by a prescriber and sets prescriber risk predictive model features to be the types of data. The types of data that indicate of at least one of fraud, waste, abuse, or a combination thereof are fewer than all types of data.

The system of any example embodiment includes the prescriber risk predictive model features having less than one-third of the types of data.

The system of any example embodiment includes the pharmacy risk predictive modeler identifying types of data in the prescription data that indicate at least one of fraud, waste, abuse, or a combination thereof by a pharmacy and setting pharmacy risk predictive model features to be the types of data, wherein the types of data indicate of at least one of fraud, waste, abuse, or a combination thereof are fewer than all types of data.

The system of any example embodiment includes the pharmacy risk predictive model features being less than one-third of the types of data.

The system of any example embodiment includes a fraud, waste or abuse processor selecting one of the patient risk predictive model, the prescriber risk predictive model and the pharmacy risk predictive model among a plurality of available predictive models based on a type of risk score being determined. When the patient risk predictive model is loaded in the processor, the processor uses the patient risk predictive model and the claims data to calculate a patient risk score over a first evaluation time period. When the prescriber risk predictive model is loaded in the processor, the processor uses the prescriber risk predictive model and the claims data to calculate a prescriber risk score over a second evaluation time period. When the pharmacy risk predictive model is loaded in the processor, the processor uses the pharmacy risk predictive model and the claims data to calculate a pharmacy risk score over a third evaluation time period. The processor is to compare a calculated one of the patient risk score, the prescriber risk score, the pharmacy risk score, or a combination thereof to determine a violation of a risk threshold and to send a risk flag to a client device when a risk threshold violation by the one risk score is determined.

The system of any example embodiment includes the processor determines the violation of the risk threshold by determining if a rate of change of the risk score over a fourth-time period exceed a rate threshold.

The system of any example embodiment includes the processor determines the violation of the risk threshold by determining if the risk score and an audit discrepancy both increase at a first rate and a second rate over a time period.

The system of any example embodiment includes the pharmacy risk predictive model includes features for calculating the pharmacy risk score of: a number of days between service and adjudication feature, a high cost brand medications as fills feature, a percentage of doctors claims that are high cost brand medications feature, a whole number billing feature, a benzodiazepine feature, a control substance feature, a compounding feature, and reversals feature.

The system of any example embodiment includes the pharmacy risk predictive model does not including a patient gender feature, a number of doctors feature, a pharmacy state feature, or a refill rate feature.

The system of any example embodiment includes the patient risk predictive model being a patient opioid risk predictive model that includes at least one of a benzodiazepine consumption feature, a number of unique prescriber and pharmacy combinations per therapy feature, a morphine equivalent dose feature, an opioid claims per pharmacy feature, a refill too soon reject transactions feature, a paid claim amount feature, a sleep claims per pharmacy feature, a number of days between earliest opioid fill and most recent opioid fill feature, a distance traveled for opioids feature, a duplicate therapy claims feature, a number of unique prescribers for control substances feature, a concomitant opioid and suboxone consumption feature, a brand claims, feature a chain pharmacy usage feature, a control substances feature, an emergency room prescriber usage feature, a night claims feature, a claims where the pharmacy and doctor are not in the same state feature, a number of submitted and then reversed transactions feature, or combinations thereof.

The system of any example embodiment includes patient opioid risk predictive model that does not include an age data type, a prior authorizations data type, a specialty drug claims data type, a maintenance utilization data type, a gender data type, a line of business data type, a name data type, as features.

The system of any example embodiment includes the prescriber risk predictive model being a prescriber opioid risk predictive model that includes at least one of a number of days between service and adjudication feature, a high cost brand medications as fills feature, a percentage of doctors claims that are high cost brand medications feature, a whole number billings feature, a benzodiazepines feature, a control substances feature, a compounding feature, a reversals feature and combinations thereof.

The system of any example embodiment includes the prescriber opioid risk predictive model not including a patient gender data type, a number of doctors data type, a pharmacy state data type, or a refill rate data type.

An example embodiment includes a system for determining drug fraud, waste or abuse scoring. The system can include a data storage device configured for storing a plurality of predictive risk models including an individual risk predictive model, a prescriber predictive model, and a pharmacy risk predictive model, the plurality of predictive risk models being derived from statistically significant script data types in a benefit manager database working backward from known incidents of fraud, waste or abuse; and one of a data query device, a data analysis device, a data manager device, a benefit manager device, and a data supplier device configured for loading one of the plurality of risk models and accessing the benefit manager database. The device is configured to select a patient risk predictive model, prescriber risk predictive model and a pharmacy risk predictive model from the plurality of predictive risk models based on a type of risk score being determined; reduce the statistically significant script data types stored it the data storage device by including only the statistically significant script data types that indicate fraud, waste, or abuse; calculate a patient risk score over a first time period using the patient risk predictive model and claims data in the benefit manager database; calculate a prescriber risk score over a second time period using the prescriber predictive model and the claims data; calculate a pharmacy risk score over a third time period using the pharmacy risk predictive model and the claims data; and determine violation of a risk threshold by at least one of the patient risk score, the prescriber risk score, and the pharmacy risk score.

The system of any example embodiment includes the processor being configured to send a risk flag to a client device when a risk threshold violation by at least one of the patient risk score, the prescriber risk score, and the pharmacy risk score is determined.

The system of any example embodiment includes the processor wirelessly transmitting the risk flag to the client device.

The system of any example embodiment includes the processor being configured to receive a reply from the client device to trigger a fraud, waste or abuse investigation.

The system of any example embodiment includes the processor being configured to determine a violation of a risk threshold includes determining if a rate of change of the risk score over a fourth-time period exceed a rate threshold.

The system of any example embodiment includes the processor being configured to determine the violation of a risk threshold the risk score and audit discrepancies both increase at a first rate and a second rate.

The system of any example embodiment includes the processor being configured to determine a decreasing risk score after a pharmacy benefit manager intervention with an increasing amount of billings after a pharmacy benefit manager intervention.

The system of any example embodiment includes the processor being configured to determine a violation of a risk threshold includes an increasing risk score and an increasing number of prescription drug claims.

The system of any example embodiment includes a viewer loading an application to a client device, wherein the viewer application is configured to provide a graphical user interface to show a risk score flag, the risk score of at least one of a pharmacy, a prescriber, a patient, or combinations thereof, wherein the viewer application is further configured to receive an input to trigger an investigation and send the trigger to a pharmacy benefits manager device.

An example embodiment is directed to a fraud, waste and abuse evaluation system. The system can include a memory storing claims data associated with a patient, a prescriber, or a pharmacy and a patient risk predictive model, a prescriber risk predictive model and a pharmacy risk predictive model; and a processor in operable communication with the memory to determine whether the claims data relates to a fraud, waste or abuse determination and if the claims data relates using a type of the claims data as a feature in a one of the patient risk predictive model, the prescriber risk predictive model and the pharmacy risk predictive model to which the claims data relates, to select the patient risk predictive model, the prescriber risk predictive model and the pharmacy risk predictive model based on a type of risk score being determined, to calculate a patient risk score over a first time period using the patient risk predictive model and the claims data, to calculate a prescriber risk score over a second time period using the prescriber risk predictive model and the claims data, to calculate a pharmacy risk score over a third time period using the pharmacy risk predictive model and the claims data, and to select at least one of the patient risk score, the prescriber risk score, the pharmacy risk score, or a combination thereof to determine violation of a risk threshold.

The system of any example embodiment includes the risk threshold including a numerical risk score threshold.

A prescription drug fraud, waste or abuse scoring system is described and may comprise: a model storage including a patient risk predictive model generated from prescription drug data that predates a first known incident of fraud, waste or abuse, a prescriber risk predictive model generated from prescription drug data that predates a second known incident of fraud, waste or abuse, and a pharmacy risk predictive model generated from prescription drug data that predates a third known incident of fraud, waste or abuse; a fraud, waste or abuse master device that receives a request for a graphical user interface including risk scores calculated from at least one the patient risk predictive model, a prescriber risk predictive model, a pharmacy risk predictive model, and combinations thereof, and a dashboard to display graphical user interface using the risk scores from the master device, the dashboard including graphs of the risk scores and interactive icons to select a next action, the next action including at least one report of the selected risk scores that include additional non-risk score data or graphs of one entity associated with one risk score.

The dashboard may show a graph of risk levels versus the number of entities in each risk level and a selectable icon to show an additional graphical user interface with more specific data related to a selected risk score.

The additional graphical user interface shows a report of all the entities that have a high risk score level that represent the greatest likelihood of fraud, waste or abuse.

In an example embodiment, the additional graphical user interface shows a graph of a selected entity's risk score over time.

In an example embodiment, the additional graphical user interface shows the graph with the selected entity's relationship to a threshold risk level.

In an example embodiment, the additional graphical user interface shows the graph with the selected entity's totaled billed amount over the same time period as the risk scores.

In an example embodiment, the additional graphical user interface shows the graph with actions taken in view of the risk scores.

In an example embodiment, the patient risk predictive model includes a weighting for each feature in the risk model. In an example embodiment, the patient risk model includes a non-opioid feature and an opioid feature that has a greater weighting in the model than the non-opioid feature.

In an example embodiment, the patient risk predictive model, the prescriber risk predictive model and the pharmacy risk predictive model are applied to prescription data over a same time period to produce patient risk scores, prescriber risk scores, and pharmacy risk scores.

The present disclosure can produce the models using selected data types that are less than the entire data types. The models can detect of fraud, waste or abuse of pharmaceuticals at various steps in the pharmaceutical supply chain. Thus, methods and systems for detection and prevention of fraud, waste and abuse in medical settings and pharmaceutical prescribing, dispensing, and use have been described. The underlying health data, e.g., prescription drug claims data, can be used, at least in part, to calculate a risk score for all parties associated with the health data. The risk score can be used to predict the risk that any single party, either alone or in conspiracy with other parties, may be committing any one of fraud, waste or abuse with regard to the healthcare service or products.

The presently described systems and methods can be applied to fraud, waste or abuse detection systems and methods for healthcare. The system may identify those entities within a healthcare managers book of business who are most likely committing some form of fraud, waste and/or abuse (FWA) using a predictive model that is derived from healthcare data that predates a known incidence of FWA. The systems determine the features used to predict FWA from the numerous data types in the database. These features can then be used on present or other data sets and time periods of data to calculate a risk score for FWA. The system uses the model to detect or predict when one or more of the entities (prescribers, pharmacies, patients) is likely involved, directly or indirectly, with FWA. The system can analyze the pharmacy where the prescription claim is submitted, the prescriber who wrote the prescription on the claim, and/or the member who is purportedly taking the prescription on the claim. The systems and methods may rank the entities using risk scores from predictive modeling techniques to provide fraud, waste and abuse risk oversight, which was previously not possible.

A user of a client device can get to the FWA calculated result in a few steps; first the main graphical user interface is provided, then the user of the client device can select at least one of the threat type, a model, a date range, a location and the like, and second, the remote server calculates the threat value, which will launch the appropriate summary window showing the threat value. The summary window in the graphical user interface shows the threat value and then more detail with regard to the threat value can be accessed.

The present specification provides non-abstract improvements to computer technology in analyzing data to generate threat models that may represent fraud, waste or abuse in medical technologies, e.g., pharmaceutical abuse. The model is based on statistically significant types of data that indicate possible fraud, waste or abuse. The model can include specific, distinct models for a patient, a prescriber and a pharmacy. The model can flag a possible FWA instance based on the model. An intervention into the FWA predicted instance can be trigger in the system based on the flag. The intervention can be restriction placed in the system that can only be released when conditions are met. The system can also provide non-abstract GUI that indicates the FWA instance with calculated risk scores preceding the instance and possible post instance along with prior flags or intervention actions. This is an improvement in electronic devices.

Although embodiments of the present invention have been described with reference to specific example embodiments, it will be evident that various modifications and changes may be made to these embodiments without departing from the broader spirit and scope of the embodiments of the invention, Accordingly, the specification and drawings are to be regarded in an illustrative rather than a restrictive sense.

We claim:

1. A data threat evaluation system, comprising:
   a secure data storage device on a server to store a plurality of data types in a master record including a first data subset that relate to a threat and a second data subset that do not relate to the threat;
   a data model structure including:
      a root object query that, when executed, returns a third data subset from the plurality of data types in the master record that predate a known threat, the third data subset including data types in both the first data subset and the second data subset;
      a model schema on the server to extract, from the third data subset, data types of the first data subset that predicate and indicate the threat, the model schema to produce at least an individualized data threat regression model, a script originator data threat regression model, and a script filler data threat regression model using the extracted data types by:
         receiving a set of training data associated with prescriptions filled by a known instance of fraud, waste or abuse (FWA) by a pharmacy, a prescriber or a patient;
         training a predictive modeler comprising a neural network, the training comprising feeding the set of training data into the predictive modeler at a rate corresponding to a known rate of FWA, the neural network configured to apply logistic regression to the set of training data to generate a prediction output;
         after feeding the set of training data into the predictive modeler, verifying the prediction output of the predictive modeler with the known instance of FWA by the pharmacy, the prescriber or the patient of the set of training data; and
         after verifying the prediction output of the predictive modeler, applying the predictive modeler to new data comprising prescription information over a given time period to predict future FWA, the predictive modeler generating risk scores for one or more pharmacies, one or more prescribers, and one or more patients indicative of risk trends;
   a processor on the server for:
      receiving, from a remote client terminal, a request to calculate a threat value based on the new data;
      responsive to receiving the request, loading one of the individualized data threat regression model, the script originator regression model, and the script filler data threat regression model and accessing the data model structure, the individualized data threat regression model generating a first score indicative of a threat by a given individual, the script originator regression model generating a second score indicative of a threat by a given prescriber, and the script filler data threat regression model generating a third score indicative of a threat by a given pharmacy, the processor being configured to apply at least one of the individualized data threat regression model, the script originator regression model and the script filler data threat regression model to the master record in the data storage device to identify potential threats identified as a variable value produced by at least one of the individualized data threat regression model, the script originator regression model and the script filler data threat regression model; and
      communicating, to the remote client terminal, the first, second, and third scores that were generated using sensitive information stored on the master record without exposing the sensitive information to the remote client terminal to maintain data integrity and data security;
   a master record prescription drug database including a plurality of verified data attributes, at least one of the plurality of verified data attributes being cross-checked against at least one of a plurality of various data sources that are deemed correct and current;
   a comparator to produce comparison data relevant to prescription drug claims, medical claims or both provided by the plurality of various data sources that are deemed correct and current, the plurality of various data sources including at least one of a benefit manager database, a data supplier database, a data manager database, and a pharmacy database, a prescription drug adjudication database, the data manager database configured for storing source data received from at least one of a plurality of various data sources, the master record, and reference data, the reference data including a plurality of data attributes that are associated with the plurality of verified data attributes of the master record, wherein the plurality of data attributes of the reference data are not deemed most significant or valuable, the comparator comparing a plurality of data attributes of the comparison data and the plurality of verified data attributes of the master record to determine that there is a difference;
   a database updater to store a current state version of the master record if there is a difference and the relative level of source priority of the data source of the comparison data is equal to or greater than the data source of the current state version of the master record;
   an individualized data threat regression modeler to access the current state version of the master record and to produce an individual risk predictive model using prescription drug data in the current state version of the master record over a first-time period that includes at least one known incident of patient FWA;
   a script originator data threat regression modeler to access current state version of the master record and to discern a script originator risk predictive model using prescription drug data in the current state version of the master record over a second-time period that includes at least one known incident of script originator FWA;
   a script filler data threat regression modeler to access the current state version of the master record and to discern a script filler risk predictive model using prescription drug data in the current state version of the master record over a third-time period that includes at least one known incident of script filler FWA; and a model storage to receive the individual risk predictive model, the script originator risk predictive model and the script filler predictive model for storing and for use in applying the models to prescription data to determine a likelihood of FWA of a modeled system.

2. The system of claim 1, wherein the data model structure configured to determine the known rate of FWA, and wherein the processor is configured to generate an individualized data threat variable value over a first-time segment using the individual data threat regression model and claims data in the master record prescription drug database.

3. The system of claim 2, wherein the processor is configured to generate a script originator data threat variable value over a second-time segment using the script originator regression model and the claims data in the master record prescription drug database, wherein the set of training data comprises opioid FWA consumption, number of unique prescriber and pharmacy combinations per therapy, morphine equivalent dose, opioid claims per pharmacy, refill too soon reject transactions, paid claim amount, sleep claims per pharmacy, number of days between earliest opioid fill, distance traveled for opioids, duplicate therapy claims, number of unique prescribers for control substances, percent of reversed transactions, percentage of control substance claims, percentage of claims at a chain pharmacy that are opioids, percentage of claims that are brands, and average number of unique doctor/pharmacy combinations per generic code number.

4. The system of claim 3, wherein the processor is configured to generate a script filler data threat variable value over a third-time segment using the script filler data threat regression model and the cl aims data in the master record prescription drug database, and wherein the processor is configured to determine that a combination of the individualized data threat variable value, script originator data threat variable value, and the script filler data threat variable value is indicative of FWA corresponding to collusion among one or more of a patient, a prescriber and a pharmacy involved in prescriptions.

5. The system of claim 2, wherein the processor is configured to generate a script originator data threat variable value over a second-time segment using the script originator regression model and the claims data in the master record prescription drug database;

wherein the processor is configured to generate a script filler data threat variable value over a third-time segment using the script filler data threat regression model and the claims data in the master record prescription drug database;

wherein the processor is configured to determine violation of a data threat threshold by at least one of the individualized data threat variable value, the script originator data threat variable value, and the script filler data threat variable value.

6. The system of claim 1, wherein the processor is configured to:

generate a plurality of threat values based on outputs from the individualized data threat regression model, the script originator regression model, and the script filler data threat regression model; and determine a violation of a data threat threshold in response to determining that a rate of change of a data threat variable value from the plurality of threat values of at least one of the individualized data threat regression model, the script originator regression model, and the script filler data threat regression model exceeds a rate threshold.

7. The system of claim 1, wherein the predictive modeler is configured to generate the risk scores based on drug type, wherein a risk score associated with a first type of drug is associated with a first risk score weight, and wherein a risk score associated with a second type of drug is associated with a second risk score weight, and wherein the individualized data threat regression model is a patient individual opioid risk predictive model that includes at least one of a benzodiazepine consumption feature, a number of unique prescriber and pharmacy combinations per therapy feature, a morphine equivalent dose feature, an opioid claims per pharmacy feature, a refill too soon reject transactions feature, a paid claim amount feature, a sleep claims per pharmacy feature, a number of days between earliest opioid fill and most recent opioid fill feature, a distance traveled for opioids feature, a duplicate therapy claims feature, a number of unique prescribers for control substances feature, a concomitant opioid and suboxone consumption feature, a brand claims feature, a chain pharmacy usage feature, a control substances feature, an emergency room prescriber usage feature, a night claims feature, a pharmacy and a doctor not-in-a-same-state feature, a number of submitted and then reversed transactions feature, or combinations thereof.

8. The system of claim 1, wherein the processor is configured to:

generate a plurality of threat values based on outputs from the individualized data threat regression model, the script originator regression model, and the script filler data threat regression model; and determine a violation of a data threat variable value in response to determining that plurality of threat values of at least one of the individualized data threat regression model, the script originator regression model, and the script filler data threat regression model increase at a first rate and audit discrepancies increases at a second rate.

9. A data threat evaluation system, comprising:

a secure data storage device on a server to store a plurality of data types related to medical treatment of a patient;

a data model structure including:

a root object query that, when executed, returns a threat data subset from the data storage device that predate a known threat, the threat data subset;

a model schema on the server to extract, from the threat data subset, data types of the threat data subset that predicate and indicate the threat, the model schema to produce at least a data threat regression model using the extracted data types by:

receiving a set of training data associated with prescriptions filled by a known instance of fraud, waste or abuse (FWA) by a pharmacy, a prescriber or a patient;

training a predictive modeler comprising a neural network, the training comprising feeding the set of training data into the predictive modeler at a rate corresponding to a known rate of FWA, the neural network configured to apply logistic regression to the set of training data to generate a prediction output;

after feeding the set of training data into the predictive modeler, verifying the prediction output of the predictive modeler with the known instance of FWA by the pharmacy, the prescriber or the patient of the set of training data; and after verifying the prediction output of the predictive modeler, applying the predictive modeler to new data comprising prescription information over a given time period to predict future FWA, the predictive modeler generating risk scores for one or more pharmacies, one or more prescribers, and one or more patients indicative of risk trends; and a processor on the server for:
receiving, from a remote client terminal, a request to calculate a threat value based on the new data;
responsive to receiving the request, loading the data threat regression model to apply the data threat regression model to a master record in the data storage device to identify potential threats identified as a variable value, wherein the master record includes a prescription drug database having a plurality of verified data attributes with at least one of a plurality of verified data attributes being cross-checked against at least one of a plurality of various data sources that are deemed correct and current; and
communicating, to the remote client terminal, the identified potential threats that were generated using sensitive information stored on the master record without exposing the sensitive information to the remote client terminal to maintain data integrity and data security.

10. The system of claim 9, further comprising a comparator to produce comparison data relevant to prescription drug cl aims, medical claims or both provided by the plurality of various data sources that are deemed correct and current, the plurality of various data sources including at least one of a benefit manager database, a data supplier database, a data manager database, and a pharmacy database.

11. The system of claim 10, wherein the data storage device includes a prescription drug adjudication database that stores source data received from at least one of a plurality of various data sources, the master record, and reference data, the reference data including a plurality of data attributes that are associated with the plurality of verified data attributes of the master record, and wherein the plurality of data attributes of the reference data are not deemed most significant or valuable, the comparator comparing a plurality of data attributes of the comparison data and the plurality of verified data attributes of the master record to determine that there is a difference.

12. The system of claim 10, further comprising a database updater to store a current state version of the master record if there is a difference and the relative level of source priority of the data source of the comparison data is equal to or greater than the data source of the current state version of the master record.

13. The system of claim 12, wherein the data model structure includes an individualized data threat regression modeler to access the current state version of the master record and to produce an individual risk predictive model using prescription drug data in the current state version of the master record over a first-time period that includes at least one known incident of patient fraud, waste or abuse.

14. The system of claim 12, wherein the data model structure includes a script originator data threat regression modeler to access current state version of the master record and to discern a script originator risk predictive model using prescription drug data in the current state version of the master record over a second-time period that includes at least one known incident of script originator fraud, waste or abuse.

15. The system of claim 12, wherein the data model structure includes a script filler threat regression modeler to access the current state version of the master record and to discern a script filler risk predictive model using prescription drug data in the current state version of the master record over a third-time period that includes at least one known incident of script filler fraud, waste or abuse.

16. The system of claim 9, wherein weights associated with one or more features in the set of training data are based on geographic location, wherein a first weight associated with a first feature in the set of training data is increased in value in response to determining that data corresponding to the first feature corresponds to a first geographical location having known FWA.

17. The system of claim 1 further comprising a viewer application configured to provide an interactive graphical user interface configured to display a threat notification, where the threat notification is from the predictive modeler.

18. The system of claim 1 further comprising a viewer application configured to receive an input to trigger an investigation of FWA.

19. The system of claim 9, wherein the model schema identifies types of data in the threat data subset that indicate at least one of FWA, or a combination thereof by an individual, wherein the types of data indicate at least one of FWA, or a combination thereof are fewer than all types of data.

20. The system of claim 19, where the types of data that indicate at least one of FWA are less than one-third of the types of data.

21. The system of claim 9 further comprising a viewer application configured to provide an interactive graphical user interface configured to display a threat notification, where the threat notification is from the predictive modeler.

22. The system of claim 9 further comprising a viewer application configured to receive an input to trigger an investigation of fraud, waste, or abuse, the viewer application being configured to generate an FWA investigation alert in response to determining that the risk scores exceed a threshold number associated with a drug of a particular class.

23. A non-transitory computer-readable medium comprising non-transitory computer readable instructions that, when executed by one or more processors, configure the one or more processors to perform operations comprising:
storing on a secure data storage device on a server a plurality of data types related to medical treatment;
receiving a set of training data associated with prescriptions filled by a known instance of fraud, waste or abuse (FWA) by a pharmacy, a prescriber or a patient;
training a predictive modeler comprising a neural network stored on the server, the training comprising feeding the set of training data into the predictive modeler at a rate corresponding to a known rate of FWA, the neural network configured to apply logistic regression to the set of training data to generate a prediction output;
after feeding the set of training data to the predictive modeler, verifying the prediction output of the predictive modeler with the known instance of FWA by the pharmacy, the prescriber or the patient of the set of training data;
after verifying the prediction output of the predictive modeler, applying the predictive modeler to new data comprising prescription information over a given time period to predict future FWA, the predictive modeler generating risk scores for one or more pharmacies, one or more prescribers, and one or more patients indicative of risk trends;

receiving, by the server from a remote client terminal, a request to calculate a threat value based on the new data;

responsive to receiving the request, loading the predictive modeler to apply the predictive modeler to a master record in a data storage device to identify potential threats identified as a variable value, wherein the master record includes a prescription drug database having a plurality of verified data attributes with at least one of a plurality of verified data attributes being cross-checked against at least one of a plurality of various data sources that are deemed correct and current; and communicating, to the remote client terminal, the identified potential threats that were generated using sensitive information stored on the master record without exposing the sensitive information to the remote client terminal to maintain data integrity and data security.

* * * * *